United States Patent
Detamore et al.

(10) Patent No.: US 10,722,614 B2
(45) Date of Patent: Jul. 28, 2020

(54) DECELLULARIZED HYALINE CARTILAGE POWDER FOR TISSUE SCAFFOLDS

(71) Applicants: The Children's Mercy Hospital, Kansas City, MO (US); The University of Kansas, Lawrence, KS (US)

(72) Inventors: Michael Detamore, Lawrence, KS (US); Amanda Renth, Lawrence, KS (US); Amanda Sutherland, Lawrence, KS (US); Emily Beck, Lawrence, KS (US); Richard Hopkins, Kansas City, MO (US); Gabriel Converse, Kansas City, MO (US)

(73) Assignees: The University of Kansas, Lawrence, KS (US); The Children's Mercy Hospital, Kansas City, MO (US)

( * ) Notice: Subject to any disclaimer, the term of this patent is extended or adjusted under 35 U.S.C. 154(b) by 313 days.

(21) Appl. No.: 15/024,317

(22) PCT Filed: Sep. 25, 2014

(86) PCT No.: PCT/US2014/057498
§ 371 (c)(1),
(2) Date: Mar. 24, 2016

(87) PCT Pub. No.: WO2015/048317
PCT Pub. Date: Apr. 2, 2015

(65) Prior Publication Data
US 2016/0235892 A1 Aug. 18, 2016

Related U.S. Application Data

(60) Provisional application No. 61/882,397, filed on Sep. 25, 2013.

(51) Int. Cl.
*A61L 27/54* (2006.01)
*A61K 35/32* (2015.01)
(Continued)

(52) U.S. Cl.
CPC ............ *A61L 27/54* (2013.01); *A61K 9/0024* (2013.01); *A61K 35/32* (2013.01); *A61L 27/20* (2013.01);
(Continued)

(58) Field of Classification Search
None
See application file for complete search history.

(56) References Cited

U.S. PATENT DOCUMENTS

| 4,656,137 A | 4/1987 | Balassa |
| 8,017,155 B2 | 9/2011 | Schwendeman et al. |

(Continued)

FOREIGN PATENT DOCUMENTS

| CN | 101890184 B | 7/2013 |
| NO | 2012142569 A2 | 10/2012 |

OTHER PUBLICATIONS

Sawkins et al. "Hydrogels derived from demineralized and decellularized bone extracellular matrix" Acta Biomater Aug. 2013; 9(8); 7865-7873. (Year: 2013).*

(Continued)

*Primary Examiner* — Carlos A Azpuru
*Assistant Examiner* — Casey S Hagopian
(74) *Attorney, Agent, or Firm* — Maschoff Brennan; Jonathan M. Benns

(57) ABSTRACT

The present invention is related to compositions comprising decellularized cartilage tissue powder in the forms of paste, putty, hydrogel, and scaffolds, methods of making compositions, and methods of using these compositions for treating osteochondral defects and full- or partial-thickness cartilage defects.

32 Claims, 35 Drawing Sheets

(51) Int. Cl.
*A61K 9/00* (2006.01)
*A61L 27/36* (2006.01)
*A61L 27/52* (2006.01)
*A61L 27/20* (2006.01)

(52) U.S. Cl.
CPC ....... *A61L 27/3612* (2013.01); *A61L 27/3687* (2013.01); *A61L 27/3691* (2013.01); *A61L 27/52* (2013.01); *A61L 2300/606* (2013.01); *A61L 2300/622* (2013.01); *A61L 2430/02* (2013.01); *A61L 2430/06* (2013.01)

(56) References Cited

U.S. PATENT DOCUMENTS

| | | |
|---|---|---|
| 8,221,500 B2 | 7/2012 | Truncale et al. |
| 8,277,832 B2 | 10/2012 | Detamore et al. |
| 2005/0251268 A1* | 11/2005 | Truncale ............... A61F 2/28 623/23.63 |
| 2011/0033540 A1* | 2/2011 | Daniloff ............... A61K 9/19 424/484 |
| 2011/0070271 A1 | 3/2011 | Truncale et al. |
| 2011/0151011 A1* | 6/2011 | Flynn ............... A61L 27/3604 424/490 |
| 2011/0195107 A1* | 8/2011 | Min ............... A61L 27/3604 424/423 |
| 2011/0212894 A1 | 9/2011 | Athanasiou et al. |

OTHER PUBLICATIONS

Kwon, JS et al., Injectable Extracellular Matrix Hydrogel Developed Using Porcine Articular Cartilage, International Journal of Pharmaceutics. Sep. 15, 2013. vol. 454. No. 1, pp. 183-191.

J Visser et al.; Crosslinkable Hydrogels Derived From Cartilage, Meniscus, and Tendon Tissue; Tissue Engineering: Part A; vol. 00, No. 00, (2015).

Luo et al.; Decellularization of Porcine Articular Cartilage Explants and Their Subsequent Repopulation With Human Chondroprogenitor Cells; Journal of the Mechanical Behavior of Biomedical Materials; vol. 55, pp. 21-31 (2016).

P Crapo et al.; An Overview of Tissue and Whole Organ Decellularization Processes; Biomaterials; 32(12); pp. 3233-3243 (2011).

B Uygun et al.; Organ Reengineering Through Development of Transplantable Recellularized Liver Graft Using Decellularized Liver Matrix; Nature Medicine; vol. 16, No1. 3; pp. 814-821 (2010).

B Elder et al.; Developing an Articular Cartilage Decellularization Process Toward Facet Joint Cartilage Replacement; Neurosurgery; vol. 66, pp. 722-727 (2010).

T Woods et al.; Effectiveness of Three Extraction Techniques in the Development of a Decellularized Bone-Anterior Cruciate Ligament—Bone Graft; Biomaterials; vol. 26; pp. 7339-7349 (2015).

* cited by examiner

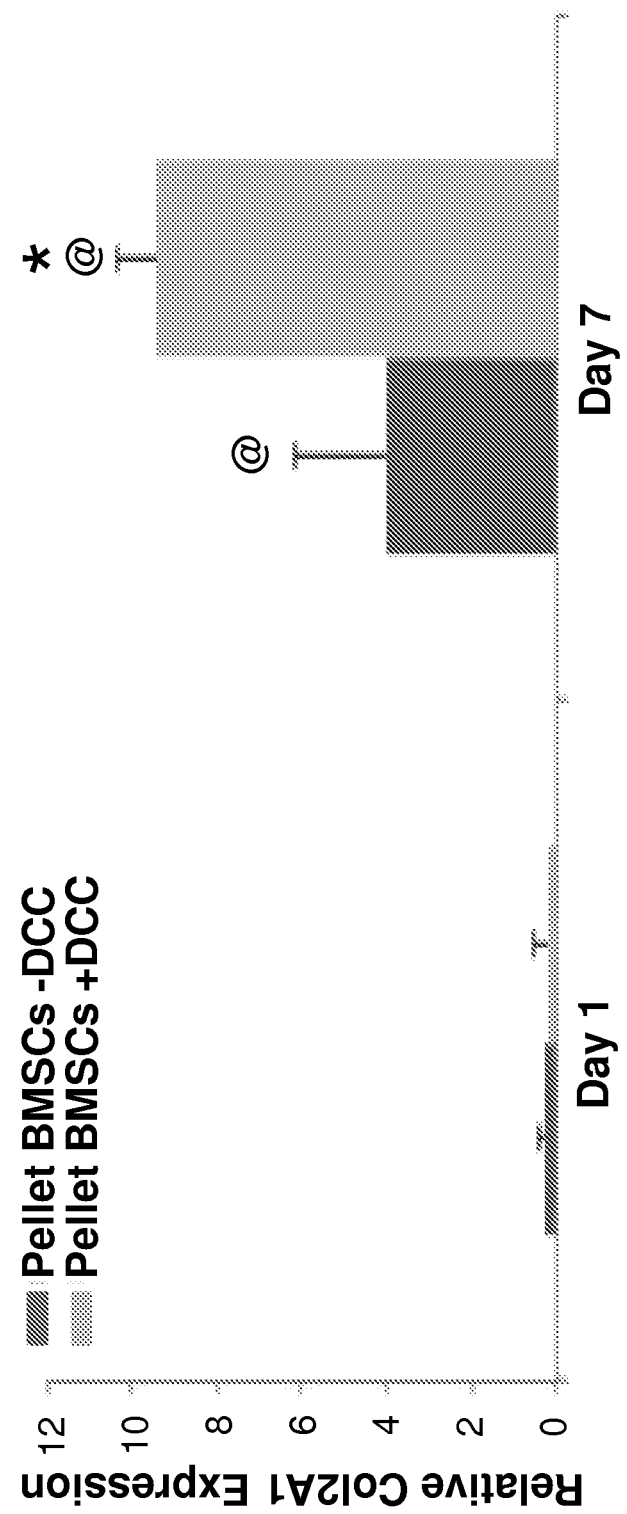

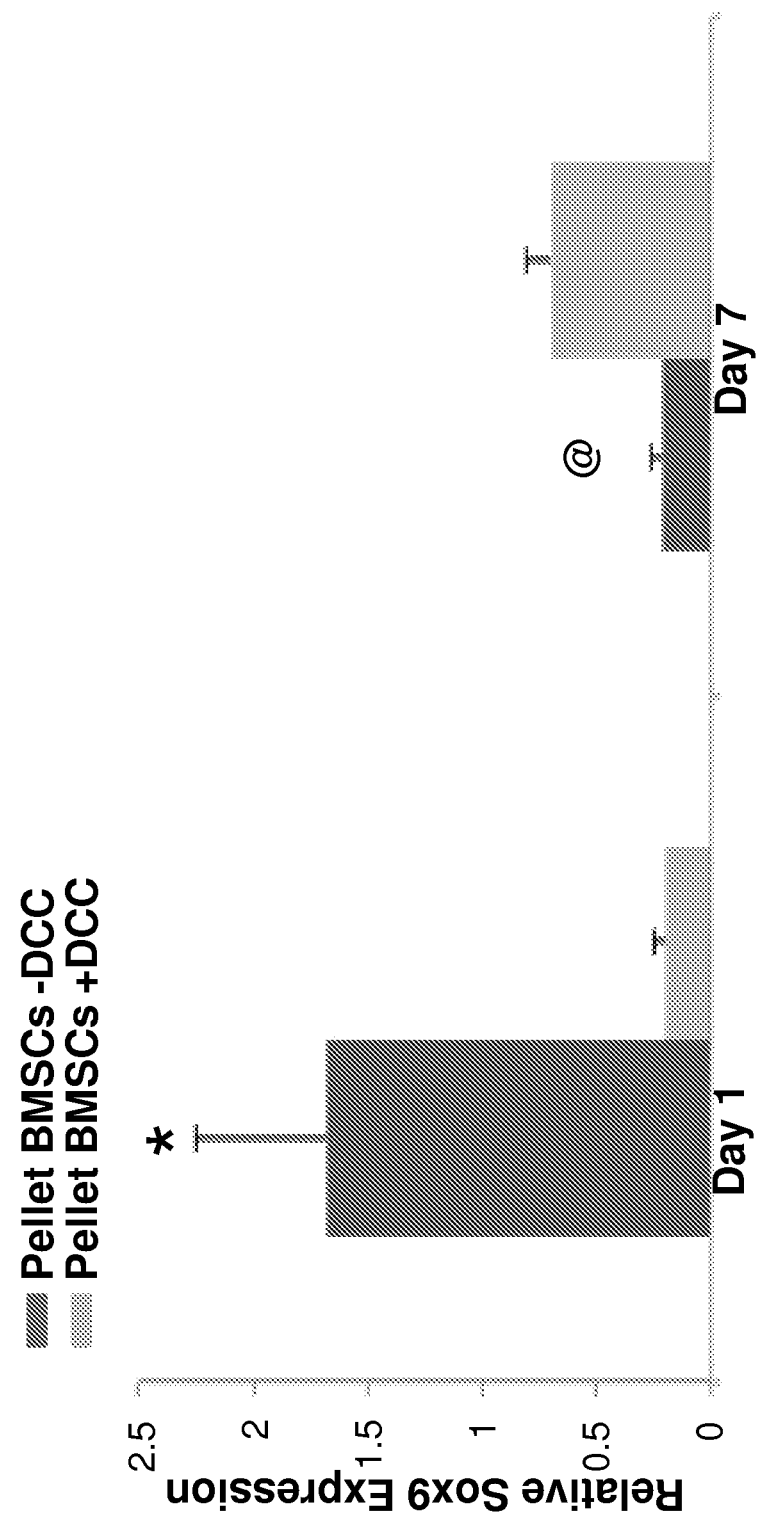

FIG. 4
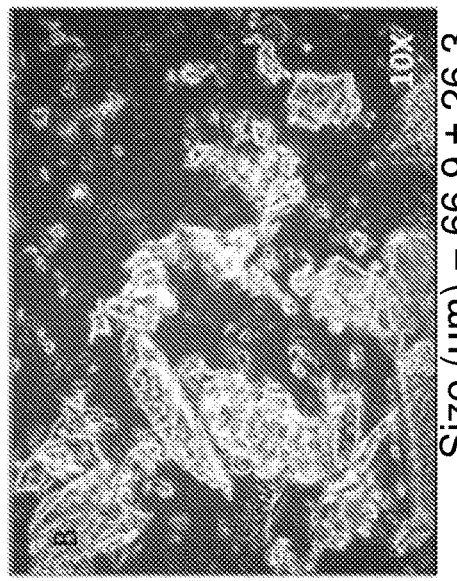
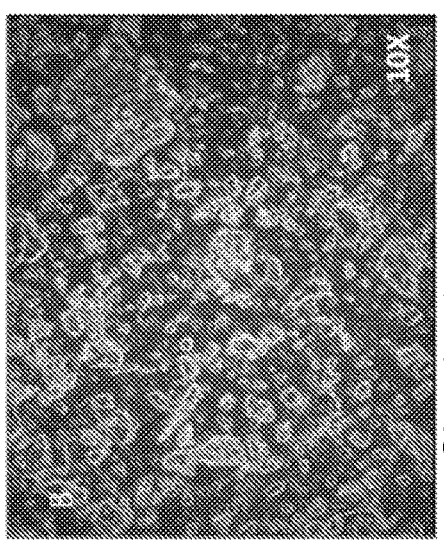
FIG. 5
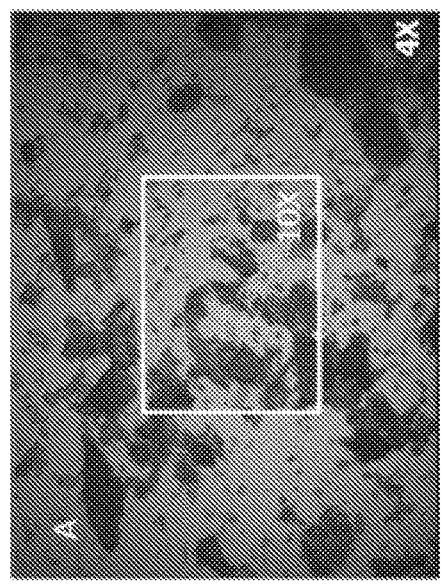
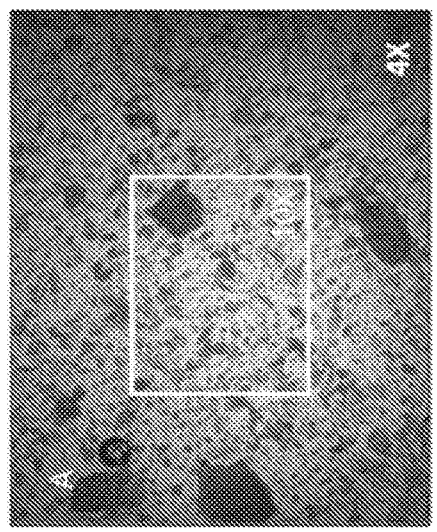

DECELLULARIZED HYALINE CARTILAGE POWDER FOR TISSUE SCAFFOLDS

FIELD OF INVENTION

The present invention relates to compositions having decellularized cartilage tissue powder, as well as methods of making and/or methods of using such decellularized cartilage tissue powder. Such compositions are desirable for treating osteochondral defects as well as full and partial thickness bone and cartilage defects including those caused by traumatic injury or osteoarthritis.

BACKGROUND OF INVENTION

Human articular cartilage is an avascular structure, which has a complex, layered and avascular tri-dimensional structure, with an extracellular matrix (ECM) made by a few highly specialized cells (chondrocytes) that typically divide very slowly. Articular cartilage exhibits a poor intrinsic healing ability due to structural and biologic characteristics, and when injured, it poses significant hurdles to repair strategies. Not only does the defect need to be repopulated with cells, but preferentially with hyaline-like cartilage.

Current cartilage treatment options can be divided into stimulation and replacement strategies. Stimulation techniques or strategies attempt to bring mesenchymal progenitors from the marrow to differentiate and repopulate the defect. Although these techniques have shown good short-term results, the repair tissue eventually fails due to the inferior structural and mechanical qualities of the resulting fibrocartilage. Replacement, on the other hand, tries to fill the defect with a native tissue obtained from nearby healthy locations. Long-term complications, donor site-associated morbidity, and the scarcity of replacement tissue are the major disadvantages of the autologous component of this technique.

New methods to stimulate mesenchymal stem cells and generate a more durable implant can be broadly divided into pre- and post-implantation strategies. In vitro optimization techniques (pre-implantation) involve the use of specific scaffold materials that promote cell survival and induce cell differentiation; growth factors to manipulate cell proliferation, differentiation, ECM production, and cellular hypertrophic terminal differentiation; adjusted culture conditions to mimic the native environment (use of flow stimulation in a bioreactor); and genetically engineered MSCs to express specific targets (ie, transforming growth factor-beta-1 and insulin-like growth factor-1). Scaffolds chosen for effective tissue engineering with respect to cartilage repair can be protein-based (collagen, fibrin, and gelatin), carbohydrate-based (hyaluronan, agarose, alginate, PLLA/PGA, and chitosan), or formed by hydrogels.

Effective tissue engineering has the potential to improve the quality of life of millions of patients and delay or even prevent future medical costs related to cartilage or bone regenerative procedures. Scaffolds possessing the functional and mechanical features resembling those within the human knee joint both during gait and at rest are in a great need. Creating scaffolds having the right mechanical compression, fluid-induced shear stress, and hydrostatic pressure is highly desirable to assist in stimulating the development of more robust cells for implantation.

SUMMARY OF INVENTION

Components found within the extracellular matrix (ECM) have emerged as an essential subset of biomaterials for tissue engineering scaffolds. Collagen, glycosaminoglycans (GAGs), and ECM-based matrices are the main categories of "raw materials" found naturally in the body that can be incorporated into scaffolds. Traditionally, however, cartilage tissue engineering scaffolds have utilized synthetic polymer components to form hydrogels or porous matrices. The present invention provides decellularized cartilage (DCC) fragments or powder as a raw material component to be utilized for scaffolds, such that it provides a microenvironment similar to that of native cartilage tissue. The decellularized cartilage powder described herein provides a platform technology upon which many cartilage, or even bone, tissue engineering scaffolds could be based on. It revolutionizes the field of treating full and partial-thickness cartilage defects caused by traumatic injury and osteoarthritis. This cartilage or bone tissue powder could also be used in tendon, ligament, meniscus, and TMJ regenerative applications. Preferably, the decellularized cartilage (DCC) fragment or powder is a chondroinductive material, meaning that it induces chondrogenesis.

One aspect of the present invention provides a composition comprising decellularized cartilage (DCC) tissue powder having particulates ranging in size from between about 1 nanometers (nm) and about 500 micrometers (µm). In some embodiments, the DCC tissue powder is derived from human or other animal cartilage tissues. In other embodiments, the DCC tissue powder is derived from synthetic cartilage tissues. In some embodiments, the DCC tissue powder comprises particulates ranging in size between about 1 nm and about 500 µm, between about 2 nm and about 450 µm, between about 3 nm and about 400 µm, between about 4 nm and about 350 µm, between about 5 nm and about 300 µm, between about 6 nm and about 250 µm, between about 7 nm and about 200 µm, between about 8 nm and about 150 µm, between about 9 nm and about 100 µm, between about 10 nm and about 50 µm, between about 10 nm and about 40 µm, between about 10 nm and about 30 µm, between about 10 nm and about 20 nm, between about 10 nm and about 10 nm, between about 10 nm and about 900 nm, between about 10 nm and about 800 nm, between about 10 nm and about 700 nm, between about 10 nm and about 600 nm, between about 10 nm and about 500 nm; between about 10 nm and about 300 nm; between about 10 nm and about 200 nm; between about 10 nm and about 100 nm; between about 10 nm and about 50 nm; or any range thereof (e.g. between about 450) nm and about 400 µm, between about 6 nm and about 50 nm, between about 10 nm and about 500 µm, and the like).

The DCC tissue powder as provided herein is soluble, with little to no dsDNA left in the tissue after the decellularization process. Preferably, at least 80% of the dsDNA is removed during the decellularization process. More preferably, the amount of dsDNA that is removed is between about 80% and 99%. In some preferred forms, the amount of dsDNA removed can be optimized for the tissue such that the tissue is in the best form possible for recellularization. In addition to the removal of large amounts of dsDNA, the decellularization process must also focus on the retention of certain proteins that will contribute to the recellularization of the tissue and the chondroinductive effects of the decellularized constructs. For example, retention of high amounts (i.e. at least 70%, more preferably at least 75%, still more preferably at least 80%, even more preferably at least 85%, still more preferably at least 90% and even more preferably at least 95%) of glycosaminoglycans is desired. Accordingly, for the decellularization of cartilage, as described herein, the amount of dsDNA remaining after the decellularization process can be brought to a desirable level, preferably between 80% and 99%. If the chondroinductive effects of a particular tissue are increased by having a residual dsDNA level between 8% and 20%, the present disclosure provides a tunable method to achieve the desired dsDNA level while retaining desirable proteins. Advantageously, using the methods of the present disclosure, any level of dsDNA removal is achievable including 80%, 81%, 82%, 83%, 84%, 85%, 86%, 87%, 88%, 89%, 90%, 91%, 92%, 93%, 94%, 95%, 96%, 97%, 98%, and even 99%. Additionally, ranges incorporating any two of these discrete values are also achievable and contemplated by the present invention. For example, dsDNA removal of 80%-84%, 91%-99%, 86%-87%, and 83%-89% are achievable and a part of the disclosure contained herein. In some preferred forms, there is less than 0.5%, more preferably less than about 0.4%, even more preferably less than about 0.3%, still more preferably less than about 0.2%, even more preferably less than about 0.1%, still more preferably less than about 0.01%, even more preferably less than about 0.005%, still more preferably less than about 0.003%, and most preferably less than about 0.002% dsDNA remaining after the decellularization process. In other preferred forms, there is between 80%-91%, more preferably between 82%-89%, still more preferably between 84%-87%, and most preferably, about 86% dsDNA remaining after the decellularization process.

In preferred forms of the invention, at least about 85% or more glycosaminoglycan content remains in the decellularized cartilage after the decellularization process in comparison to fresh cartilage tissue. The DCC tissue powder as provided, preferably has about 88% or more, 92% or more, 95% or more, 97% or more, 99% or more glycosaminoglycan content retained in comparison to fresh cartilage tissue.

The DCC tissue powder is biologically functional in stimulating bone marrow stem cell responses, which include, but are not limited to, cell attachment, cell differentiation, tissue regeneration, and tissue specific marker gene expression. In one example, the DCC tissue powder stimulates the expression of chondrogenic marker genes, which include Sox9 and Col2A1.

Another aspect of the present invention provides a hyaline cartilage tissue hydrogel, comprising decellularized cartilage powder having particulates ranging in size from between about 1 nanometers and about 500 micrometers, and at least one hydrogel. Preferred particulate sizes are as described above. "Hydrogel", as used herein, refers to a water-soluble cross-linked network of polymer chains. Hydrogels may be prepared from natural polymers that include, but are not limited to, collagen, hyaluronate, chitosan, gelatin, algenate, pectin, carrageenen, chondroiten sulfate, dextran sulfate, polylysine, carboxymethyl chitin, fibrin, dextran, agarose, and pullulan. Hydrogels also may be prepared from synthetic polymers that include, but are not limited to, poly(2-hydroxyethylrnethacrylate (HEMA), polyphazene, poly(ethylene oxide) PEO and its copolymers, polyesters such as PEG (polyethylene glycol)-PLA (polylactic acid)-PEG, PEG-PLGA-PEG, PEG-PCL (polycaprolactone)-PEG, PLA-PEG-PLA, PHB (poly(3-hydroxybutyrate)), P(PF-co-EG) plus or minus acrylate end groups, P(PER/PBO terephthalate), other polymers such as PEG-bis-PLA-acrylate), PEG-g-P(Aam-co-Vamine), PAAm, P(NIPAAm-co-Aac), P(N IPA Am-co-EMA), PVAc/PVA, PNVP, P(MMA-co-HEMA), P(AN-co-allyl sulfonate), P(biscarboxy-phenoxy-phosphazine), P(GEMA-sulfate). Hydrogels may be prepared from both natural and synthetic polymers, examples of which include, but are not limited to, P(PEG-co-peptides), alginate-g-(PEO-PPO-PEO), P(PLGA-co-serine), collagen-acrylate, alginate-acrylate, P(HPMA-g-peptide), P(hema/Matrigel®), and HA-g-NIPAAm. In some embodiments, the hydrogel comprises a polymerized polyalkyleneglycolyl diacrylate. In another embodiment, the hydrogel comprises polyalkyleneglycolyl monoacrylates, including methacrylates. In yet another embodiment, the hydrogel comprises hyaluronic acid, chitosan, agarose, polyvinylacetate, polyvinylpyrrolide, or polyvinylalcohol nanoparticles. In one preferred embodiment, wherein the hydrogel in the hyaline cartilage tissue hydrogel comprises Methacrylated Hyaluronic Acid (MeHA), the resulting cartilage tissue hydrogel has an adjustable yield stress between 0 to 400 Pa depending on the length of solubilization. In a preferred embodiment, the yield stress of hydrogel as provided is at least 100 Pa. In some preferred embodiments, the yield stress of the cartilage tissue hydrogel is between about 100 Pa to about 200 Pa. As such the cartilage tissue hydrogel as provided exhibits excellent ability in molding into desirable three dimensional shapes.

Another aspect of the present invention provides a hyaline cartilage tissue paste comprising slightly solubilized decellularized cartilage powder particulates ranging from between about 10 w/v % and about 90 w/v %, and Methacrylated Hyaluronic Acid (MeHA) ranging from between about 10 w/v % and about 90 w/v %. In some embodiments, the hyaline cartilage tissue paste comprises about 10%, 15%, 20%, 25%, 30%, 35%, 40%, 45%, 50%, 55%, 60%, 65%, 70%, 75%, 80%, 85%, 90% (w/v), or any range thereof, of the slightly solubilized decellularized cartilage powder particulates and conversely, of the MeHA. If the slightly solubilized decellularized cartilage powder particulates are suspended at a high concentration, the particulates can form a composition that is putty-like, and if suspended at a somewhat lower concentration, it can form a composition that is paste-like. Such putties or pastes can conveniently be packed into, for example, holes, gaps, or spaces of any shape in tissues and organs so as to substantially fill such holes, gaps, or spaces. As provided herein, the slightly solubilized decellularized cartilage powder particulates are the solid portion of the solubilized cartilage tissue powder solution, after centrifugation, that remained at the bottom of the centrifuge tube. The solubility in the portion comprising the slightly solubilized decellularized cartilage powder particulates in the present invention may range from about 5% to about 15%, or about 10% to about 20%, or from about 15% to about 25%, or any range thereof, which is adjustable by modifying centrifugation parameters such as speed and duration. In some embodiments, the hyaline cartilage tissue paste comprises about 90%, 85%, 80%, 75%, 70%, 65%, 60%, 55%, 50%, 45%, 40%, 35%, 30%, 25%, 20%, 15%, 10% (w/v), or any range thereof, of the Methacrylated Hyaluronic Acid. In one embodiment, the hyaline cartilage tissue paste further comprises one or more additives selected from the group consisting of carrier, one or more biomaterials for tissue engineering scaffolds, one or more therapeutic agents to enhance tissue regeneration, and combinations thereof. Therapeutic agents are as described herein. In one embodiment, the hyaline cartilage tissue paste comprising MeHA, after exposure to UV light, crosslinks into a hyaline cartilage tissue gel.

Another aspect of the present invention provides polymer microspheres in contact with decellularized cartilage powder, wherein the decellularized cartilage powder includes particulates having sizes as described above. In one embodiment, the microsphere-based scaffolds can be prepared from PLG or PLGA microspheres. However the microspheres can be prepared from substantially any polymer, such as biocompatible, bioerodable, and/or biodegradable polymers. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, poly anhydrides, polyanhydride-co-imides, polyesters, polyorthoesters, polycaprolactones, polyesters, poly anhydrides, polyphosphazenes, poly(phosphoesters), polyester amides, polyester urethanes, polycarbonates, polytrimethylene carbonates, polyglycolide-co-trimethylene carbonates, poly (PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), poly(L-lysine), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), poly(anhydride-co-imides), poly(amides), poly(iminocarbonates), poly(urethanes), poly(organophasphazenes), poly(phosphates), poly(ethylene vinyl acetate) and other acyl substituted cellulose acetates and derivatives thereof, poly(amino acids), poly(acrylates), polyacetals, poly(cyanoacrylates), poly(styrenes), poly(vinyl chloride), poly(vinyl fluoride), polyvinyl imidazole), chlorosulfonated polyolefins, polyethylene oxide, combinations thereof, polymers having monomers thereof, or the like. In certain preferred aspects, the nano-particles include hydroxypropyl cellulose (HPC), N—isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof. A non-limiting method for making nano-particles is described in U.S. Publication 2003/0138490, the entirety of which is incorporated by reference.

In one embodiment, the present invention provides a tissue engineering scaffold comprising polymer microspheres in contact with the decellularized cartilage tissue powder. In some embodiments, the DCC powder is intimately mixed with the microsphere polymers. In other embodiments, the DCC powder is used to coat the microsphere polymers. In yet another embodiment, the decellularized cartilage powder is encapsulated in said microspheres assembling the scaffold. Therefore, the present invention also provides a tissue engineering scaffold comprising microspheres coated with decellularized cartilage powder including particulates ranging in size as described above and preferably from between about 1 nanometers and about 500 micrometers. Alternatively, the present invention provides a tissue engineering scaffold comprising microspheres encapsulated with decellularized cartilage powder including particulates ranging in size as described above and preferably from between about 1 nanometers to about 500 micrometers.

The above scaffolds provided herein may further comprise one or more therapeutic agents that are useful in scaffolds applications. Exemplary therapeutic agents include: anti-proliferative/antimitotic agents including natural products such as *vinca* alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/HI a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (Cortisol, cortisone, fludrocortisone, prednisone, prednisolone, 6α-methylprednisolone, triamcinolone, betamethasone, and dexamethasone), non-steroidal agents (salicylic acid derivatives e.g., aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors; β$_2$ agonists (e.g. salbutamol, terbutaline, clenbuterol, salmeterol, formoterol); steroids such glycocorticosteroids, preferably anti-inflammatory drugs (e.g. Ciclesonide, Mometasone, Flunisolide, Triamcinolone, Beclomethasone, Budesonide, Fluticasone); anticholinergic drugs (e.g. ipratropium, tiotropium, oxitropium); leukotriene antagonists (e.g. zafirlukast, montelukast, pranlukast); xantines (e.g. aminophylline, theobromine, theophylline); Mast cell stabilizers (e.g. cromoglicate, nedocromil); inhibitors of leukotriene synthesis (e.g. azelastina, oxatomide ketotifen); mucolytics (e.g. N-acetylcysteine, carbocysteine); antibiotics, (e.g. Aminoglycosides such as, amikacin, gentamicin, kanamycin, neomycin, netilmicin streptomycin, tobramycin; Carbacephem such as loracarbef, Carbapenems such as ertapenem, imipenem/cilastatin meropenem; Cephalosporins—first generation—such as cefadroxil, cefaxolin, cephalexin; Cephalosporins—second generation—such as cefaclor, cefamandole, defoxitin, cefproxil, cefuroxime; Cephalosporins—third generation—cefixime, cefdinir, ceftaxidime, defotaxime, cefpodoxime, ceftriaxone; Cephalosporins—fourth generation—such as maxipime; Glycopeptides such as vancomycin, teicoplanin; Macrolides such as azithromycin, clarithromycin, Dirithromycin, Erythromycin, troleandomycin; Monobactam such as aztreonam; Penicillins such as Amoxicillin, Ampicillin, Azlocillin, Carbenicillin, Cloxacillin, Dicloxacillin, Flucloxacillin, Mezlocillin, Nafcillin, Penicillin, Piperacillin, Ticarcillin; Polypeptides such as bacitracin, colistin, polymyxin B; Quinolones such as Ciprofloxacin, Enoxacin, Gatifloxacin, Levofloxacin, Lomefloxacin, Moxifloxacin, Norfloxacin, Ofloxacin, Trovafloxacin; Sulfonamides such as Mafenide, Prontosil, Sulfacetamide, Sulfamethizole, Sulfanamide, Sulfasalazine, Sulfisoxazole, Trimethoprim, Trimethoprim-Sulfamethoxazole Co-trimoxazole (TMP-SMX); Tetracyclines such as Demeclocycline, Doxycycline, Minocycline, Oxytetracycline, Tetracycline; Others such as Chloramphenicol, Clindamycin, Ethambutol, Fosfomycin, Furazolidone, Isoniazid, Linezolid, Metronidazole, Nitrofurantoin, Pyrazinamide, Quinupristin/Dalfopristin, Rifampin, Spectinomycin); pain relievers in general such as analgesic and antiinflammatory drugs, including steroids (e.g. hydrocortisone, cortisone acetate, prednisone, prednisolone, methylprednisolone, dexamethasone, betamethasone, triamcino lone, beclometasone, fludrocortisone acetate, deoxycorticosterone acetate, aldosterone); and non-steroid antiinflammatory drugs (e.g. Salicylates such as aspirin, amoxiprin, benorilate, coline magnesium salicylate, diflunisal, faislamine, methyl salicylate, salicyl salicylate); Arylalkanoic acids such as diclofenac, aceclofenac, acematicin, etodolac, indometacin, ketorolac, nabumetone, sulindac tolmetin; 2-Arylpropionic acids (profens) such as ibuprofen, carprofen, fenbufen, fenoprofen, flurbiprofen, ketoprofen, loxoprofen, naproxen, tiaprofenic acid; N-arylanthranilic acids (fenamic acids) such as mefenamic acid, meclofenamic acid, tolfenamic acid; Pyrazolidine derivatives such as phenylbutazone, azapropazone, metamizole, oxyphenbutazone; Oxicams such as piroxicam, meloxicam, tenoxicam; Coxib such as celecoxib, etoricoxib, lumiracoxib, parecoxib, rofecoxib (withdrawn from market), valdecoxib (withdrawn from market); Sulphonanilides such as nimesulide; others such as licofelone, omega-3 fatty acids; cardiovascular drugs such as glycosides (e.g. strophantin, digoxin, digitoxin, proscillaridine A); respiratory drugs; antiasthma agents; bronchodilators (adrenergics: albuterol, bitolterol, epinephrine, fenoterol, formoterol, isoetharine, isoproterenol, metaproterenol, pirbuterol, procaterol, salmeterol, terbutaline); anticancer agents (e.g. cyclophosphamide, doxorubicine, vincristine, methotrexate); alkaloids (i.e. ergot alkaloids) or triptans such as sumatriptan, rizatriptan, naratriptan, zolmitriptan, eletriptan and almotriptan, than can be used against migraine; drugs (i.e. sulfonylurea) used against diabetes and related dysfunctions (e.g. metformin, chlorpropamide, glibenclamide, glicliazide, glimepiride, tolazamide, acarbose, pioglitazone, nateglinide, sitagliptin); sedative and hypnotic drugs (e.g. Barbiturates such as secobarbital, pentobarbital, amobarbital; uncategorized sedatives such as eszopiclone, ramelteon, methaqualone, ethchlorvynol, chloral hydrate, meprobamate, glutethimide, methyprylon); psychic energizers; appetite inhibitors (e.g. amphetamine); antiarthritis drugs (NSAIDs); antimalaria drugs (e.g. quinine, quinidine, mefloquine, halofantrine, primaquine, cloroquine, amodiaquine); antiepileptic drugs and anticonvulsant drugs such as Barbiturates, (e.g. Barbexaclone, Metharbital, Methylphenobarbital, Phenobarbital, Primidone), Succinimides (e.g. Ethosuximide, Mesuximide, Phensuximide), Benzodiazepines, Carboxamides (e.g. Carbamazepine, Oxcarbazepine, Rufinamide) Fatty acid derivatives (e.g. Valpromide, Valnoctamide); Carboxilyc acids (e.g. Valproic acid, Tiagabine); Gaba analogs (e.g. Gabapentin, Pregabalin, Progabide, Vigabatrin); Topiramate, Ureas (e.g. Phenacemide, Pheneturide), Carbamates (e.g. emylcamate Felbamate, Meprobamate); Pyrrolidines (e.g. Levetiracetam Nefiracetam, Seletracetam); Sulfa drugs (e.g. Acetazolamide, Ethoxzolamide, Sultiame, Zonisamide) Beclamide; Paraldehyde, Potassium bromide; antithrombotic drugs such as Vitamin K antagonist (e.g. Acenocoumarol, Dicumarol, Phenprocoumon, Phenindione, Warfarin); Platelet aggregation inhibitors (e.g. antithrombin III, Bemiparin, Deltaparin, Danaparoid, Enoxaparin, Heparin, Nadroparin, Pamaparin, Reviparin, Tinzaparin); Other platelet aggregation inhibitors (e.g. Abciximab, Acetylsalicylic acid, Aloxiprin, Ditazole, Clopidogrel, Dipyridamole, Epoprostenol, Eptifibatide, Indobufen, Prasugrel, Ticlopidine, Tirofiban, Treprostinil, Trifusal); Enzymes (e.g. Alteplase, Ancrod, Anistreplase, Fibrinolysin, Streptokinase, Tenecteplase, Urokinase); Direct thrombin inhibitors (e.g. Argatroban, Bivalirudin. Lepirudin, Melagatran, Ximelagratan); other antithrombotics (e.g. Dabigatran, Defibrotide, Dermatan sulfate, Fondaparinux, Rivaroxaban); antihypertensive drugs such as Diuretics (e.g. Bumetanide, Furosemide, Torsemide, Chlortalidone, Hy dchloro thiazide, Chlorothiazide, Indapamide, metolaxone, Amiloride, Triamterene); Antiadrenergics (e.g. atenolol, metoprolol, oxprenolol, pindolol, propranolol, doxazosin, prazosin, teraxosin, labetalol); Calcium channel blockers (e.g. Amlodipine, felodipine, dsradipine, nifedipine, nimodipine, diltiazem, verapamil); Ace inhibitors (e.g. captopril, enalapril, fosinopril, lisinopril, perindopril, quinapril, ramipril, benzapril); Angiotensin II receptor antagonists (e.g. candesartan, irbesartan, losartan, telmisartan, valsartan); Aldosterone antagonist such as spironolactone; centrally acting adrenergic drugs (e.g. clonidine, guanabenz, methyldopa); antiarrhythmic drug of Class I that interfere with the sodium channel (e.g. quinidine, procainamide, disodyramide, lidocaine, mexiletine, tocamide, phenyloin, encamide, flecamide, moricizine, propafenone), Class II that are beta blockers (e.g. esmolol, propranolol, metoprolol); Class III that affect potassium efflux (e.g. amiodarone, azimilide, bretylium, clorilium, dofetilide, tedisamil, ibutilide, sematilide, sotalol); Class IV that affect the AV node (e.g. verapamil, diltiazem); Class V unknown mechanisms (e.g. adenoide, digoxin); antioxidant drugs such as Vitamin A, vitamin C, vitamin E, Coenzime Q1O, melanonin, carotenoid terpenoids, non-carotenoid terpenoids, flavonoid polyphenolic; antidepressants (e.g. mirtazapine, trazodone); antipsychotic drugs (e.g. fluphenazine, haloperidol, thiotixene, trifluoroperazine, loxapine, perphenazine, clozapine, quetiapine, risperidone, olanzapine); anxyolitics (Benzodiazepines such as diazepam, clonazepam, alprazolam, temazepam, chlordiazepoxide, flunitrazepam, lorazepam, clorazepam; Imidaxopyridines such as Zolpidem, alpidem; Pyrazolopyrimidines such as zaleplon); antiemetic drugs such as Serotonine receptor antagonists (dolasetron, granisetron, ondansetron), dopamine antagonists (domperidone, droperidol, haloperidol, chlorpromazine, promethazine, metoclopramide) antihystamines (cyclizine, diphenydramine, dimenhydrinate, meclizine, promethazine, hydroxyzine); antiinfectives; antihystamines (e.g. mepyramine, antazoline, diphenhydramine, carbinoxamine, doxylamine, clemastine, dimethydrinate, cyclizine, chlorcyclizine, hydroxyzine, meclizine, promethazine, cyprotheptadine, azatidine, ketotifen, acrivastina, loratadine, terfenadine, cetrizidinem, azelastine, levocabastine, olopatadine, levocetrizine, desloratadine, fexofenadine, cromoglicate nedocromil, thiperamide, impromidine); antifungus (e.g. Nystatin, amphotericin B, natamycin, rimocidin, filipin, pimaricin, miconazole, ketoconazole, clotrimazole, econazole, mebendazole, bifonazole, oxiconazole, sertaconazole, sulconazole, tiaconazole, fluconazole, itraconazole, posaconazole, voriconazole, terbinafine, amorolfine, butenafine, anidulafungin, caspofungin, flucytosine, griseofulvin, fluocinonide) and antiviral drugs such as Anti-herpesvirus agents (e.g. Aciclovir, Cidofovir, Docosanol, Famciclovir, Fomivirsen, Foscarnet, Ganciclovir, Idoxuridine, Penciclovir, Trifluridine, Tromantadine, Valaciclovir, Valganciclovir, Vidarabine); Anti-influenza agents (Amantadine, Oseltamivir, Peramivir, Rimantadine, Zanamivir); Antiretroviral drugs (abacavir, didanosine, emtricitabine, lamivudine, stavudine, tenofovir, zalcitabine, zidovudine, adeforvir, tenofovir, efavirenz, delavirdine, nevirapine, amprenavir, atazanavir, darunavir, fosamprenavir, indinavir, lopinavir, nelfinavir, ritonavir, saquinavir, tipranavir); other antiviral agents (Enfuvirtide, Fomivirsen, Imiquimod, Inosine, Interferon, Podophyllotoxin, Ribavirin, Viramidine); drugs against neurological dysfunctions such as Parkinson's disease (e.g. dopamine agonists, L-dopa, Carbidopa, benzerazide, bromocriptine, pergolide, pramipexole, ropinipole, apomorphine, lisuride); drugs for the treatment of alcoholism (e.g. antabuse, naltrexone, vivitrol), and other addiction forms; vasodilators for the treatment of erectile dysfunction (e.g. Sildenafil, vardenafil, tadalafil), muscle relaxants (e.g. benzodiazepines, methocarbamol, baclofen, carisoprodol, chlorzoxazone, cyclobenzaprine, dantrolene, metaxalone, orphenadrine, tizanidine); muscle contractors; opioids; stimulating drugs (e.g. amphetamine, cocaina, caffeine, nicotine); tranquillizers; antibiotics such as macrolides; aminoglycosides; fluoroquinolones and β-lactames; vaccines; cytokines; growth factors; hormones including birth-control drugs; sympathomimetic drugs (e.g. amphetamine, benzylpiperazine, cathinone, chlorphentermine, clobenzolex, cocaine, cyclopentamine, ephedrine, fenfluramine, methylone, methylphenidate, Pemoline, phendimetrazine, phentermine, phenylephrine, propylhexedrine, pseudoephedrine, sibutramine, symephrine); diuretics; lipid regulator agents; antiandrogen agents (e.g. bicalutamide, cyproterone, flutamide, nilutamide); antiparasitics; blood thinners (e.g. warfarin); neoplastic drugs; antineoplastic drugs (e.g. chlorambucil, chloromethine, cyclophosphamide, melphalan, carmustine, fotemustine, lomustine, carboplatin, busulfan, dacarbazine, procarbazine, thioTEPA, uramustine, mechloretamine, methotrexate, cladribine, clofarabine, fludarabine, mercaptopurine, fluorouracil, vinblastine, vincristine, daunorubicin, epirubicin, bleomycin, hydroxyurea, alemtuzumar, cetuximab, aminolevulinic acid, altretamine, amsacrine, anagrelide, pentostatin, tretinoin); hypoglicaemics; nutritive and integrator agents; growth integrators; antienteric drugs; vaccines; antibodies; diagnosis and radio-opaque agents; or mixtures of the above mentioned drugs (e.g. combinations for the treatment of asthma containing steroids and β-agonists); or any other biologically active agent such as nucleic acids, DNA, RNA, siRNA, polypeptides, antibodies, and the like. Growth factors and adhesion peptides can also be useful for tissue development within a subject and can be included in or with the microspheres.

Another aspect of the present invention provides a method of preparing decellularized cartilage powder. The general method comprises the steps of (a) pulverizing cartilage tissue to produce cartilage tissue fragments; (b) decellularizing the cartilage tissue fragments to produce decellularized cartilage (DCC) tissue fragments; and (c) grinding and more preferably cryogrinding the DCC tissue fragments to produce DCC tissue powder. The DCC tissue powder made using this method as provided includes particulates preferably ranging in size from between about 1 nanometers and about 500 micrometers, however, other sizes as described above are also produceable. Further the resultant DCC tissue powder preferably has no more than about 1-20%, more preferably 1-16%, and still more preferably 1-14% of dsDNA left, but retains about 85% or more glycosaminoglycan content in comparison to fresh cartilage tissue prior to or without decellularization. The resultant DCC tissue powder also stimulates bone marrow stem cell responses including, but not limited to, cell attachment, cell differentiation, tissue regeneration, and tissue specific marker gene expression. In one example, the DCC tissue powder stimulates the expression of chondrogenic marker genes, which include Sox9 and Col2A1. Preferably, the DCC tissue powder is a chondroinductive material, meaning that it induces chondrogenesis.

To produce the DCC, fresh bovine knee joints were obtained from a local abattoir within 24 hours of sacrifice. Articular cartilage was excised, washed with phosphate buffered saline, cryopreserved for storage until use, and later pulverized to form tissue fragments. It is understood that cryopreservation is for storage purposes only as the excised tissue could be immediately pulverized prior to use or cryopreservation. The step of pulverization is for an initial fragmentation of the cartilage tissue to facilitate decellularization by decreasing diffusion distances and allowing better penetration by the decellularization solutions. Any conventional method capable of breaking the cartilage tissue into fragments or coarse powder can be used for pulverization. Pulverization can reduce the excised tissue into fragments of varying sizes, including all of the sizes described herein, depending on the desired use or particular application of the fragments or powder. Further, the pulverization can be accomplished using any conventional pulverizing or fragmenting apparatus that accomplishes the goal of reducing the size of the excised tissue. Preferably, the step of decellularization further comprises a step of confining or consolidating the cartilage tissue fragments, such that the fragmented tissue can be placed in a container to allow the subsequent decellularization process. In one embodiment, the tissue fragment may be confined within a dialysis tubing with both ends of the tubing sealed, thereby forming a tissue packet. In another embodiment, the tissue fragments may be consolidated in a centrifuge tube. Centrifugation between steps consolidates the tissue fragments at the bottom of the tube, whereas the various solutions used for each step would be separated and removed.

After pulverization, the resulting cartilage fragments are preferably decellularized using conventional decellularization methods. Preferred decellularization methods and solutions are described in U.S. application Ser. Nos. 12/483,196 and 12/813,487, the teachings and content of which are hereby incorporated in their entireties. In preferred forms, decellularization was accomplished by subjecting the cartilage fragments to reciprocating osmotic shock, followed by detergent (Triton X-100, 0.05% v/v; sodium-lauroyl sarcosine, 1.0% v/v) and enzymatic (Benzonase®; 0.0625 KU/ml) washes to remove cellular material. Organic extraction was performed using ion exchange resins.

After decellularization, tissue was analyzed in fresh, cryopreserved, and decellularized states to quantify double stranded DNA content fluorometrically and GAG content colorimetrically. In addition, native and DCC samples were analyzed for chemical composition changes using Transmission FTIR with the KBr pellet method. Following DCC characterization, $2\times10^6$ rBMSCs at passage 4 (P4) were pelleted alone or with DCC fragments in 15 mL centrifuge tubes and cultured in standard chondrogenic medium with no growth factors for 7 days. Pellets (n=3) were harvested at Day 1 and Day 7 for gene expression analysis by reverse transcriptase polymerase chain reaction (PCR) with collagen II (COL2A1), aggrecan (Acan), and SRY-box9 (Sox9) primers and glyceraldehyde-3 phosphate dehydrogenase (GAPDH) as an endogenous control. Statistical analyses were performed using a single factor analysis of variance (ANOVA) in IBM SPSS 21.0 software (SPSS, Inc., Chicago, IL), followed by a Tukey's honestly significant difference post hoc test when significance was detected below the p=0.05 value.

Another aspect of the present invention provides a method of preparing hyaline cartilage tissue paste comprising the steps of (a) solubilizing decellularized cartilage tissue powder, preferably in an acidic solvent to make a solubilized decellularized cartilage (SDCC) solution; (b) incubating the SDCC solution with a protease; (c) separating the supernatant containing solubilized particulates from the solids containing slightly solubilized particulates by centrifuging the SDCC solution and collecting the solids; (d) mixing between about 10% to 90% w/v methacrylated hyaluronic acid (MeHA) with between about 10% to 90% w/v solids containing slightly solubilized particulates to form a paste. The DCC tissue powder used in this method preferably includes a majority of the particulates formed ranging in size from between about 1 nanometers and about 500 micrometers, with other sizes being as described herein. The resultant paste has a yield stress adjustable between about 0 Pa to about 400 Pa, by adjusting the length of the solubilization of the DCC powder. Preferably the yield stress of the paste before crosslinking, and preferably photocrosslinking, is between about 100 pa to about 200 pa. The step of incubating the SDCC solution in the general method may further comprise the step of adjusting the SDCC solution at the end of incubation to physiological pH and osmolality using bases or acids.

Another aspect of the present invention provides a method of preparing hyaline cartilage tissue gel using the supernatant portion of the SDCC after centrifugation. The method comprises the steps of (a) solubilizing decellularized cartilage tissue powder to make solubilized decellularized cartilage (SDCC) solution; (b) incubating SDCC solution with a protease; (c) separating supernatant containing solubilized particulates and solids containing slightly solubilized particulates by centrifuging the SDCC solution and collecting the solids; (d) mixing methacrylated hyaluronic acid (MeHA) of between about 10 w/v % and about 90 w/v % to between about 10 w/v % and about 90 w/v % of solids containing slightly solubilized DCC particulates to form a paste; (e) molding the paste in a three dimensional shape and crosslinking the mixture, preferably using a photoinitiator and UV light exposure, to form a hyaline cartilage tissue gel. In this method, the DCC tissue powder used preferably includes a majority of the formed particulates ranging in size from between about 1 nanometers and about 500 micrometers, and the resultant hyaline cartilage tissue gel has mechanical compression, fluid-induced shear stress, and hydrostatic pressure characteristics resembling these same characteristics in typical physiological conditions of cartilage tissue. The step of incubating the SDCC solution in this method may further comprise the step of adjusting the SDCC solution at the end of incubation to physiological pH and osmolality using bases or acids. In this method, cross-linking may be effected by physical, chemical, and/or photo cross-linking. Physical cross-linking occurs due to ionic linkages, hydrogen bonding, van der Waals forces, or other physical forces. Chemical cross-linking occurs due to formation of covalent linkages using chemical initiators. Photo cross-linking, also termed photopolymerization, of hydrogels may occur by exposure to ultraviolet and/or visible light, either in the presence or absence of a photo initiator. In addition, hydrogels may be formulated as temperature sensitive compounds comprising polymers which can go through a phase transition from solution to a gel triggered by a very small change of temperature near the lower critical solution temperature (LCST). For example, the temperature sensitive hydrogel are liquid at about ambient room temperature (about 20° C.) and transition to become a solid (gel) at about body temperature (about 37° C.). Any polymers may be used to prepare temperature sensitive hydrogels as long as it possesses the necessary properties to support the hydrogel. Examples of such polymers include, but are not limited to, N-isopropyl acrylamide polymer, ethylhydroxyethylcellulose and its derivatives, poly(ethylene glycol)/poly (D,L-lactic acid-co-glycolic acid) block co-polymers and analogs, and poly(etheylene oxide-b-propylene oxide-b-ethylene oxide). In one embodiment, the crosslinking is effected by exposing the mold to UV light.

The present invention further provides an alternative method of preparing hyaline cartilage tissue hydrogel, which comprises the steps of (a) solubilizing decellularized cartilage tissue powder to make solubilized decellularized cartilage (SDCC) solution; (b) incubating the SDCC solution with a protease; (c) separating the supernatant containing solubilized particulates and solids containing slightly solubilized particulates by centrifuging the SDCC solution and collecting the supernatant; (d) methacrylating the solubilized particulates in the supernatant by mixing the supernatant with glycidyl methacrylate, triethylamine, and tetrabutyl ammonium bromide to make MeSDCC solution; (e) obtaining dry methacrylated SDCC powder by precipitating the MeSDCC solution and subsequent lyophilization; (f) mixing the dry methacrylated SDCC powder with a photoinitiator solution and placing the mixture in a three dimensional mold, and (g) exposing the mold to UV light to form hyaline cartilage tissue hydrogel. As provided above, cross-linking can be carried out in various alternative ways, all of which are incorporated herein. In one preferred method, the mixture containing methacrylated SDCC powder is cross-linked using UV light. The DCC tissue powder used in this method preferably includes a majority of the formed particulates ranging in size from between about 1 nanometers and about 500 micrometers; and the resultant hyaline cartilage tissue hydrogel has mechanical compression, fluid-induced shear stress, and hydrostatic pressure resembling those found under physiological conditions of cartilage tissue. The step of incubating the SDCC solution in the general method may further comprise the step of adjusting the SDCC solution at the end of incubation to physiological pH and osmolality using bases or acids.

A further aspect of the present invention provides a method for coating microspheres with decellularized cartilage powder, and the method generally comprises the steps of: (a) solubilizing decellularized cartilage tissue powder to make solubilized decellularized cartilage (SDCC) solution; (b) suspending microspheres in solution for lyophilization; (c) assembling scaffolds by flowing lyophilized microsphere suspension into a three dimensional mold; (d) contacting the scaffolds with the SDCC solution for a time sufficient for the decellularized cartilage powder to attach to the microspheres forming the scaffolds; and (e) removing the scaffolds for lyophilization. The DCC tissue powder used in this method preferably includes a majority of the formed particulates ranging in size from between about 1 nanometers and about 500 micrometers. The general method may further comprise a step of fabricating microspheres before step (b). The methods of making the scaffolds from the microspheres may include the use of a solvent or solvent system (i.e., media or media system) that is compatible with the particular polymer of the microsphere, which polymers have been described above and incorporated herein. The solvent or solvent system selected to mold the microspheres together are described herein. Examples of some solvents can include hexane, benzene, toluene, diethyl ether, chloroform, ethyl acetate, 1,4-dioxane, tetrahydrofuran, dichloromethane, acetone, acetonitrile, dimethylformamide, dimethyl sulfoxide, acetic acid, n-butanol, 2-butanol, 3-butanol, t-butyl alcohol, carbon tetrachloride, chlorobenzene, isopropanol, n-propanol, ethanol, methanol, formic acid, water, cyclohexane, 1,2-dichloroethane, diethyl ether, diethylene glycol, diglyme, dimethyl ether, dioxane, ethylene glycol, glycerin, heptane, hexamethylphosphoramide, hesamethylphosphorous triamide, hexane, nitromethane, pentane, petroleum ether, propanol, pyridine, o-xylene, m-xylene, p-xylene, and the like. Carbon dioxide can also be used as a solvent or media to meld the microspheres together. Additionally, solvents known to be useful with particular polymers can be used or combined with the solvents described herein.

Yet another aspect of the present invention provides a method for encapsulating decellularized cartilage powder in a microsphere polymer, which comprises the steps of: (a) solubilizing decellularized cartilage tissue powder to make solubilized decellularized cartilage (SDCC) solution; (b) providing an encapsulating solution containing the SDCC and microsphere polymer, wherein the microsphere polymer is insoluble in the encapsulating solution, and (c) fabricating microspheres encapsulating decellularized cartilage tissue powder. The method of fabricating microspheres is known in the art, for example, the Precision Particle Fabrication technique (Berkland, C., K. Kim, et al. (2001). "Fabrication of PLG microspheres with precisely controlled and monodisperse size distributions." J Control Release 73(1): 59-74). The DCC tissue powder used in this method preferably includes the majority of the formed particulates ranging in size from between about 1 nanometers and about 500 micrometers. In one embodiment, the encapsulating solution step (b) comprises between about 10 w/v % and about 90 w/v % SDCC and between about 10 w/v % and about 90 w/v % microsphere polymer. Suitable microsphere polymers have been described above and are incorporated herein. In one embodiment, the microsphere polymer is PLGA.

Still another aspect of the present invention provides a method of treating an osteochondral defect, which method comprises the step of contacting an osteochondral defect with a composition comprising decellularized cartilage (DCC) tissue powder, wherein the DCC tissue powder preferably includes the majority of the formed particulates ranging in size from between about 1 nanometers and about 500 micrometers with preferred sizes being as described herein. Osteochondral defects are joint disorders in which lesions form in the articular cartilage and the underlying subchondral bone. Osteochondral defects are common in humans, as well as in other animals including horses. Osteochondral defects most commonly affect knee, and other joints such as in children. As provided in this method, said osteochondral defects include those that occur, whether caused by traumatic injury or osteoarthritis, in knees, ankles, elbows, patellas, vertebrae, femoral heads, glenoids of the scapula, and growth plates, which may be treated by repairing cartilage. The cartilage related composition for cartilage repairing in this method is selected from the group consisting of decellularized cartilage (DCC) tissue powder paste, putty, gel, hydrogel, and scaffolds. Such compositions can conveniently be placed into, for example, holes, gaps, or spaces of any shape in tissues and organs so as to substantially fill such holes, gaps, or spaces. In one embodiment, such holes, or gaps or spaces, are cartilage lesions in various osteochondral defects. In the present method of treating osteochondral defects, the compositions used and the methods of making these compositions have been described in detail and are incorporated herein.

Yet another aspect of the present invention provides a method of treating full and partial thickness cartilage defects comprising the step of contacting said defects with a composition comprising decellularized cartilage tissue powder, wherein the DCC tissue powder preferably includes the majority of the formed particulates ranging in size from between about 1 nanometers and about 500 micrometers, with preferred sizes being described herein. Preferred compositions include those described herein.

In humans, when articular cartilage fails to heal spontaneously, it leads to partial-thickness cartilage lesions that have fissures less than 1.5 cm in diameter. The exposed cell surfaces in the lesion cannot support cell adhesion, cell migration or fibrin clot attachment. When the fissures extend down to subchondral bone and have diameter greater than 1.5 cm, it is often categorized as full-thickness cartilage lesions. Full or partial thickness cartilage defects can affect any cartilaginous structure including the knee, elbow, wrist, ankle, shoulder and hip joints. Therefore, the method of treating partial-thickness cartilage lesions includes treating any cartilage defect including those selected from the group of knee, elbow, wrist, ankle, shoulder and hip joints. The cartilage-related composition for cartilage repairing in this method is selected from the group consisting of decellularized cartilage (DCC) tissue powder paste, putty, hydrogel, and scaffolds. Such compositions can conveniently be placed into, for example, holes, gaps, or spaces of any shape or thickness in tissues and organs so as to substantially fill such holes, gaps, or spaces. In one embodiment, such holes, or gaps or spaces, are cartilage lesions in various full and partial thickness cartilage defects. In the present method of treating osteochondral defects, the compositions used and the methods of making these compositions have been described in detail and are incorporated herein.

Other aspects and iterations of the invention are described in more detail below.

DEFINITIONS

Cartilage is usually found in close association with bone in the body. It is a type of connective tissue which is tough, semi-transparent, elastic and flexible. Hyaline cartilage is semi-transparent and is extremely strong, but very flexible and elastic. Hyaline cartilage consists of living cells, chondrocytes. Hyaline cartilage occurs in the trachea, the larynx, the tip of the nose, in the connection between the ribs and the breastbone and also the ends of bone where they form joints.

"Cartilage tissue fragments", as used herein, refers to cartilage tissue coarse powder, an initial fragmentation of the cartilage tissue obtained from pulverizing raw cartilage tissue material. Cartilage tissue fragments have decreased diffusion distances required for the decellularization solutions.

"Decellularization", for purposes of the present invention, refers to the process of removing cells and/or cellular debris from a tissue. In a preferred embodiment the decellularization process prepares tissue, such that it is available to accept new cells into its biological scaffold.

"Osteochondral" or "osteochondral defects", as used herein, refers to joint disorders in which lesions form in the articular cartilage and the underlying subchondral bone. Osteochondral defects are common in human, as well as in other animals including horses. Osteochondral defects most commonly affect knee, and other joints including such joints in children. As provided in this method, said osteochondral defects include those that occur, whether caused by traumatic injury or osteoarthritis, in any cartilage-based structure including knees, ankles, elbows, patellas, vertebrae, femoral heads, jaw, glenoids of the scapula, and growth plates.

"DCC", as used herein, refers to decellularized cartilage tissue. Based on the context, DCC may be used to further refer non-solubilized decellularized cartilage tissue powder.

"DCC tissue fragment", as used herein, refers to the cartilage tissue fragments after being pulverized and going through the decellularization process.

"SDCC" or "solubilized decellularized cartilage tissue powder", or "solubilized decellularized cartilage tissue particulates", or "solubilized decellularized cartilage tissue", as used herein, refers to DCC that has been solublilized wherein the DCC, prior to solublilization, had particulates ranging in size as described herein but preferably having the majority of formed particulates ranging in size from 1 nm to 500 µm, and obtained after initial pulverization, decellularization and any other grinding including cryogrinding of the raw cartilage tissue.

"SDCC solution", as used herein, refers to the solution comprising solubilized decellularized cartilage tissue powder.

"Powderized DCC", or "powderized decellularized cartilage tissue", as used herein, refers to cartilage tissues in a powder form, obtained after initial pulverization, decellularization and grinding or cryogrinding of the raw cartilage tissue.

"Slightly solubilized DCC", or "slightly solubilized decellularized cartilage", or "slightly solubilized decellularized cartilage powder" refers to the particulates in the solid portion of the solubilized cartilage tissue powder solution, after centrifugation, which remained at the bottom of the centrifuge tube. The solubility in the portion comprising the slightly solubilized decellularized cartilage powder particulates in the present invention may range from about 5% to about 15%, or about 10% to about 20%, or from about 15% to about 25%, or any range thereof, which is adjustable by modifying the solubilization period.

"Tissue packet", as used herein, refers to the dialysis tubing containing tissue fragments with both ends of the tubing sealed to confine the content therein.

"Debridement", as used herein, refers to processes by which dead, contaminated or adherent tissue or foreign materials are removed from a tissue. One type of debridement is an enzymatic debridement.

"Enzyme treatment", as used herein, refers to the addition of an enzyme to a solution or treatment of a material, such as tissue, with an enzyme.

"Detergent Wash or rinse", as used herein, refers to the washing, soaking, or rinsing of a tissue or solution with a detergent. The detergent can be any type of detergent including, but not limited to, nonionic detergents, anionic, zwitterionic, detergents for the use of cell lysis, and combinations thereof.

"Solvent Extraction", as used herein, refers to the separation of materials of different chemical types and solubilities by selective solvent action. Some materials are separated more easily in one solvent than by another, hence there is a preferential extractive action. This process can be used to refine products, chemicals, etc.

"Osmotic Shock" as used herein, is a sudden change in the solute concentration around a cell causing rapid change in the movement of water across the cell membrane. This is possible under conditions of high concentrations of salts, substrates, or any solute in the supernatant causing water to be drawn out of the cells via osmosis. This process disrupts cell membranes and inhibits the transport of substrates and cofactors into the cell, thus, "shocking" and disrupting them, and resulting in easier removal of cells and cell debris.

"Organic Extraction" or "Organic Solvent Extraction", for purposes of the present invention, refers to the "solvent extraction" described above, wherein said solvent is of organic nature.

"Digestion", as used herein, refers to a chemical digestion. This also includes an enzymatic digestion.

For purposes of the present invention, a "lower level" or "reduced" amount is in comparison to a tissue not decellularized according to the methods of the present invention. Preferably, the characteristic or property of the tissue decellularized in accordance with methods of the present invention is at least 10% lower or reduced by at least 10%. Conversely, a "higher level" or "increased" amount is in comparison to a tissue not decellularized according to the methods of the present invention. Preferably, the characteristic or property of the tissue decellularized in accordance with the methods of the present invention is at least 10% higher or increased by at least 10%. Tissues not decellularized according to the methods of the present invention include, but are not limited to, cryopreserved tissues, biomechanical tissues, and other types of scaffolds used for bioengineering or tissue engineering in the prior art.

Additionally, for the purposes of the present invention, all references to omega or Σ decell or decellularization process refer to the decell processes in accordance with the present invention.

BRIEF DESCRIPTION OF THE FIGURES

FIGS. 3A and 3B illustrate PCR results showing relative gene expression (Col2A1 gene, 3A; Sox9 gene, 3B) increase in rBMSC (rat bone marrow stem cell) pellet culture samples with and without DCC treatment;

FIG. 4 illustrates the light microscopy images of decellularized porcine cartilage at (A) 4× and (B) 10× midway through cryogrinding with an average particle size of 66.9 µm;

FIG. 5 illustrates the light microscopy images of decellularized porcine cartilage at (A) 4× and (B) 10× through cryogrinding cycles with an average particle size of 38.9 µm;

FIG. 12 B illustrates the samples forming different gel formations.

DETAILED DESCRIPTION OF THE PREFERRED EMBODIMENTS

Figure 1:
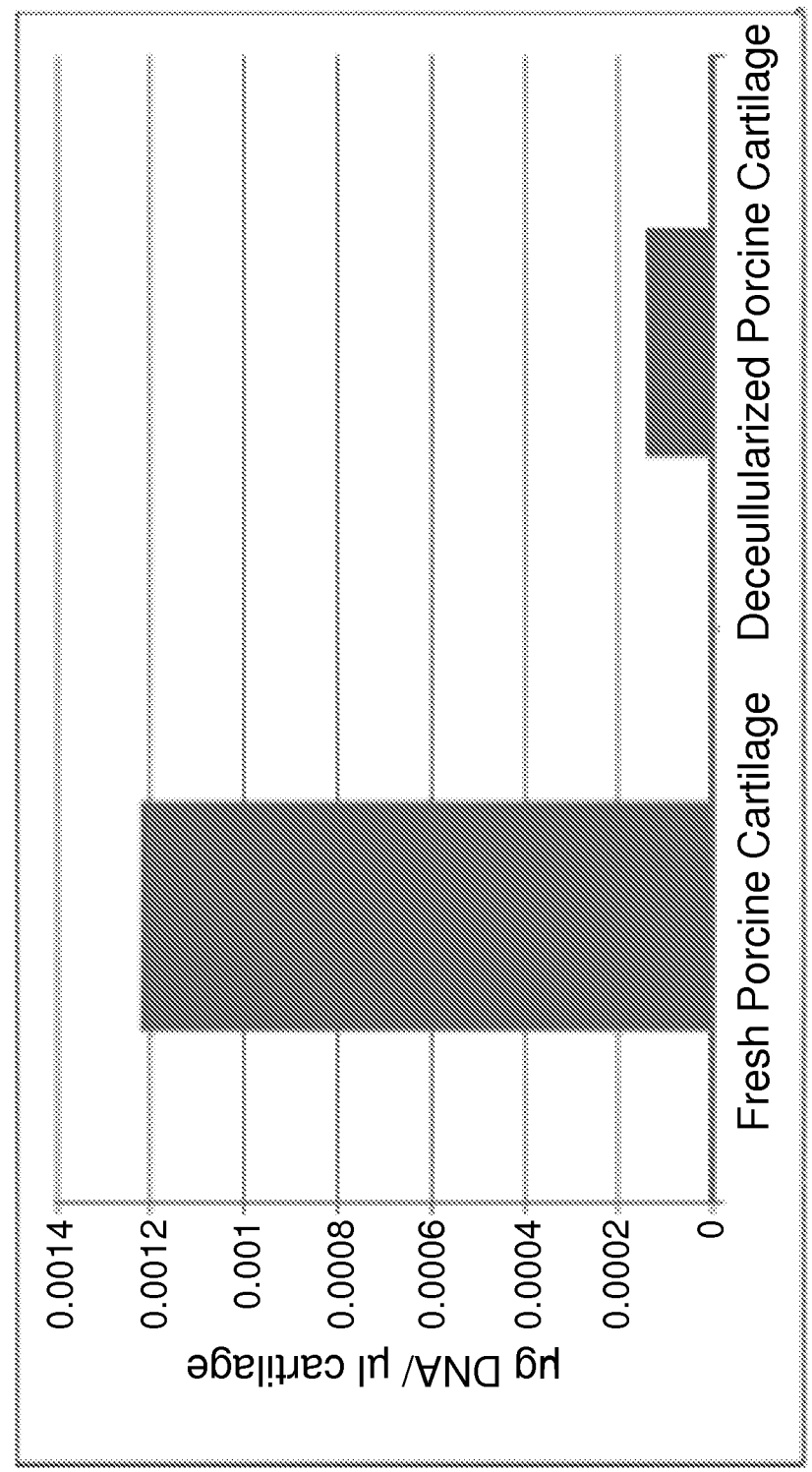
FIG. 1 illustrates the picogreen data showing a decrease in the amount of double stranded DNA from the native to the decellularized porcine cartilage.

The following examples are representative of preferred embodiments of the present invention. It is understood that nothing herein should be taken as a limitation upon the overall invention.

EXAMPLE 1

This example illustrates one embodiment of the cartilage tissue decellularization process of the present invention.

Materials and Methods

Solutions Used:

a. Triton X®-100 (Triton): 0.05% (v/v) Triton X®-100 solution a 1:2000 dilution derived from 100% Triton X®-100 detergent (Sigma T8787) in ddH$_2$O. For 2 L use 1 mL 100% Triton-X®, 1999 mL ddH$_2$O. In general, a graduated cylinder was filled with deionized water and placed on a stir plate. A magnetic stir bar was added. The Triton-X was then added and the stir plate was turned on and the speed increased until the Triton-X began to mix with the water. The mixing was continued until the Triton-X was dissolved. The solution was transferred to a beaker containing the remaining amount of deionzed water and placed on a stir plate. A magnetic stir bar was added and the two solutions were mixed until they were combined. The beaker was transferred to a laminar flow hood before being sterile filtered.

b. N-lauroylsarcosine Sodium Salt Solution (NLS): 1% NLS Solution a 1:20 dilution derived from 20% Sodium Laureth Sulfate (Sigma—L7414) in ddH$_2$O. For 2 L use 100 mL 20% NLS, 1900 mL ddH$_2$O. In general, the N-lauroyl sarcosine is added to deionized water in a beaker and mixed using a stir plate and magnetic stir bar.

c. 2×-Hypertonic Salt Solution (HSS): 1.8% (w/v) NaCl (Fisher- BP358-1), 12.5% (w/v)n or about 683 mM D-Mannitol (Sigma- M9647), 2.3 mM MgCl$_2$ (Sigma-M2643), 500 mM KCl (Sigma P4504) in water. In general, the NaCl, MgCl$_2$ and KCl are weighed out and added to 0.9% saline before being mixed using a stir plate and magnetic stir bar until the salts were dissolved. Next, the mannitol was added and stirred until dissolved. The final volume of HSS after the addition of mannitol will be greater than initial volume of the salt/saline mixture.

d. 3× Saline Mannitol Solution (SMS): 2.7% (w/v) NaCl (Fisher- BP358-1), 12.5% or about 683 mM D-Mannitol (Sigma- M9647). In general, the NaCl and mannitol are weighed out and added to 0.9% saline before being mixed using a stir plate and magnetic stir bar until the salts are dissolved.

e. RNA—DNA Enzyme Extraction Buffer (BENZ): 12.5 KU of Benzonase® (Sigma- E1014) per 200 mL ddH$_2$O, 8 mM MgCl$_2$ (Sigma- M2643), pH to 8.0 using diluted NH$_4$OH (~100 μL needed of 1M solution). For 400 mL use 400 mL ddH$_2$O, 1 vial Benzonase® (25 KU), 650 mg MgCl2 (Sigma- M2643).

f. Organic Solvent Extraction Buffer (EtOH): 2:5 dilution of ethyl alcohol 200 proof (Sigma- 459836) in ddH$_2$O- 40% v/v solution. For 2 L use 800 mL ethanol, 1200 mL ddH$_2$O. In general, the ethanol is measured out into a graduated cylinder and poured into a beaker before adding the deionized water and being stirred using a magnetic stir bar.

Bovine articular cartilage was harvested. An initial fragmentation of the cartilage tissue was conducted to facilitate decellularization by decreasing diffusion distances and allowing better penetration by the decellularization solutions. The fragmented tissue was placed in a container to allow the subsequent decellularization process. In one embodiment, the tissue fragments were confined within a dialysis tubing with both ends of the tubing sealed, thereby forming a tissue packet. In another embodiment, the tissue fragments were consolidated in a centrifuge tube. Centrifugation between steps consolidated the tissue fragment at the bottom of the tube, whereas the various solutions used for each step would be separated and removed.

On Day One of processing, the detergent and osmotic shock sequences were performed. The pre-prepared tissue packets were placed in 250 mL flasks filled with 200 mL HSS with one tissue packet in each jar. The flasks containing HSS and the tissue packet were left under gentle agitation at 70 RPM overnight at 21° C.

On Day Two of processing, the tissue packets were transferred to wide mouth jars and washed/incubated in deionized water at 40-220 RPM at a temperature of 21° C. for about 1 hour. At the end of 1 hour, the tissue packets were transferred to a wide mouth jar containing Triton-X for washing/incubating at 40-220 RPM at a temperature of 21° C. for about 3 hours. The packets were then rinsed with ddH2O before being washed/incubated with ddH2O at 40-220 RPM and 21° C. for 10 minutes before being washed/incubated with HSS a second time at 40-220 RPM and 21° C. for 2 hours. After the second HSS wash/incubation, the packets were washed/incubated with ddH2O at 40-220 RPM and 21° C. for 1 hour. The packets were then washed/incubated with Triton-X for 3 hours at 40-220 RPM and 21° C. Each wash or rinse was conducted in a new sterile 250 mL flask and the transfer was completed under a sterile laminar flow hood. Next, a RNA-DNA enzyme extraction was performed. A flask containing sterilized BENZ at a pH of 8.0-9.5, preferably 8.5, was used for the extraction and the tissue packets were transferred into the BENZ solution, and shaken on a rocker plate at 40-220 RPM at 37° C. overnight.

On Day Three, the tissue packets were transferred to wide mouth jars having deionized water for washing/incubating at 40-220 RPM at 21° C. for about an hour. The tissue packets were then placed in NLS solution on a rocker plate and were incubated overnight at 40-220 RPM at 21° C.

On Day Four of Processing, an organic extraction was performed. The tissue packets were rinsed once for 2 hours in deionized water at 40-220 RPM at 21° C. Next, an extraction was completed using ethyl alcohol. For the extraction, the tissue packets were rinsed/incubated for 30 minutes with EtOH at 40-220 RPM at 21° C. After the extraction, an ion exchange detergent residual extraction for dual chamber was set up using 5 g of each type of the organic exchange resin beads. The beads were soaked in EtOH for 5 minutes and then quickly rinsed in deionized water. The beads were then aseptically added to a wide mouth jar flask filled with deionized water. The tissue packets were then aseptically transferred to the jars having the beads, and the jars were incubated overnight at 40-220 RPM at 21° C.

On Day Five of Processing, a Mannitol wash or soak was performed. The wash or soak was carried out for those tissue packets which were not immediately being placed into the post-decellularization storage solution for immediate use. For those tissue packets placed in the wash or soak, they were washed or soaked for 2 hours in SMS on a rocker plate at 40-220 RPM at 21° C. After 2 hours, the tissue packets were placed in 50 mL conical tubes containing Cryomedia before being frozen at −80° C.

Results and Conclusions

The decellularization process produced cartilage tissue powders that are less calcified, with little to no dsDNA left in the tissue, having about 90% of glycosaminoglycan content retained, having better biomechanical properties than cartilage tissue that was cryopreserved or decellularized using a different method other than that of the present invention.

EXAMPLE 2

This example illustrates the methods of making decellularized cartilage tissue powder, and the characterization thereof.

Materials and Methods

Animals

All animal procedures were carried out under protocols approved by the Institutional Animal Care and Use Committee and animals received humane care in compliance with the *Guide for Care and Use of Laboratory Animals* (NIH Publication #85-23). Fresh bovine knee joints were obtained from a local abattoir within 24 hours of sacrifice. Articular cartilage was excised, washed with phosphate buffered saline, cryopreserved for storage until use.

Tissue Pulverization

The cryopreserved cartilage tissue was first pulverized into a coarse powder, or fragments, to decrease diffusion distances required for the decellularization solutions.

Decellularization

A decellularization technique previously developed was used in this study to remove cellular and nuclear material, thereby reducing potential antigenicity. The tissue fragments were then loaded into dialysis tubing for confinement during processing. Briefly, decellularization was accomplished by subjecting the cartilage fragments to reciprocating osmotic shock, followed by detergent (Triton X-100, 0.05% v/v; sodium-lauroyl sarcosine, 1.0% v/v) and enzymatic (Benzonase®; 0.0625 KU/ml) washes to remove cellular material. Organic extraction was performed using ion exchange resins. Following the above processing, the tissue was frozen in a cryoprotectant at −80° C. Tissue was then analyzed at fresh, cryopreserved, and decellularized states for characterization and further processing, such as, cryogrinding.

DNA Content Analysis Using Picogreen

The PicoGreen® dsDNA Quantitation Reagent (Molecular Probes, Inc., Eugene, Oreg.) was supplied as a 1 mL concentrated dye solution in anhydrous dimethylsulfoxide (DMSO). A 2× working solution of the PicoGreen® Reagent was prepared on the day of experiment by making a 1:200 dilution of the concentrated dye solution in 1×TE (10 mM Tris-HCl, 1 mM EDTA, pH 7.5). The protocol is available on the world wide web at: topac.com/picogreen.html, which is incorporated herein in its entirety.

GAG Content Analysis in Decellularized Tissue Using DMMB Assay

Tissue was analyzed at fresh, cryopreserved, and decellularized states to quantify double stranded DNA content fluorometrically using Di-methyl methylene blue (DMMB) assay. DMMB solution (40 mM NaCl; 40 mM Glycine; 46☐M DMMB) and PBE buffer (100 mM $Na_2HPO_4$; 5 mM EDTA) were prepared accordingly. Next 200 µl of DMMB to 50 µl of standard or sample in PBE, was added and mixed well, and the absorbance at 525 nm was read before Calculating samples using a standard curve.

PCR Analysis for Gene Expression in rBMSC Treated with DCC rBMSCs (rat bone marrow stem cell) at passage 4 (P4) were pelleted alone or with DCC fragments in 15 mL centrifuge tubes and cultured in standard chondrogenic medium with no growth factors for 7 days. Pellets (n=3) were harvested at Day 1 and Day 7 for gene expression analysis by reverse transcriptase polymerase chain reaction (PCR).

Powderization of Decellularized Tissue

The cryopreserved and decellularized cartilage was ground using a freezer mill (i.e., cryogrinding) into heterogeneous particles ranging in size from 20 nanometers to 50 micrometers with the majority of the particles being less than 20 micrometers. The decellularized material was solubilized in HCl and pepsin to create a decellularized cartilage solution that can be brought back to physiological pH by adding NaOH and 10×PBS.

The decellularized cartilage solution was then processed to result in decellularized cartilage powder for use in tissue engineering scaffolds.

Statistical Analysis

All statistical analyses were performed using a single factor analysis of variance (ANOVA) in IBM SPSS 21.0 software (SPSS, Inc., Chicago, Ill.), followed by a Tukey's honestly significant difference post hoc test (R. Lowry, available on the World Wide Web at: vassarstats.net/textbook/ch14pt2.html) when significance was detected below the p=0.05 value. Serially-measured continuous variables were analyzed by mixed-models repeated measures analysis of variance (ANOVA). Fixed model effects included time, treatment and the treatment by time interaction and the random effect was subject under the treatment. Variables measured at only a single point during the study were analyzed using a general linear model ANOVA. For all ANOVA analyses, the appropriate correlation matrix was chosen based on the smallest Akaike's Information Criteria and post-hoc mean comparisons were made using Bonferroni multiple significance tests. Categorical variables were evaluated using the Pearson chi squared analysis and are presented as median±range. Data are presented as mean±standard error (continuous variables) or median±range (categorical variables) and statistical significance was set at P<0.05.

Results and Conclusions

Bovine articular cartilage was harvested, fragmented and decellularized and examined for DNA content, GAG content, and chemical composition. Then, the DCC tissue pieces were placed in pellet culture to determine their influence on rat bone marrow stem cell (rBMSC) gene expression. Rather than examining DCC as freeze dried scaffolds and ECM matrices, the rBMSC response to particulates of tissue was examined. The decellularized cartilage particulates allow composite formulations with polymers and to produce polymeric scaffolds and suspension or emulsion compositions for direct application to cartilage defects.

Decellularized Tissue Powder Characterization

Double stranded DNA content fresh, cryopreserved and decellularized bovine cartilage tissue powder were each quantified fluorometrically (for example, using Picogreen) and GAG (glycosaminoglycan) content colorimetrically (DMMB assay, Blyscan). DNA content differed between fresh, cryopreserved, and decellularized tissue powder groups with 0.224±0.134, 0.132±0.069, and 0.0029±0.0016 µg RNA/mg hydrated tissue, respectively. DNA content was significantly reduced (p<0.005) between fresh and decellularized bovine cartilage tissue powder by 98.9%. GAG content remained similar throughout all groups with mean values of 2.353±0.088, 2.267±0.146, and 2.066±0.099 µg GAG/mg hydrated tissue, respectively. However, there was a significant reduction in GAG content from fresh to decellularized bovine tissue powder (p<0.01), although over 87% of native GAGs remained after decellularization.

Figure 2:
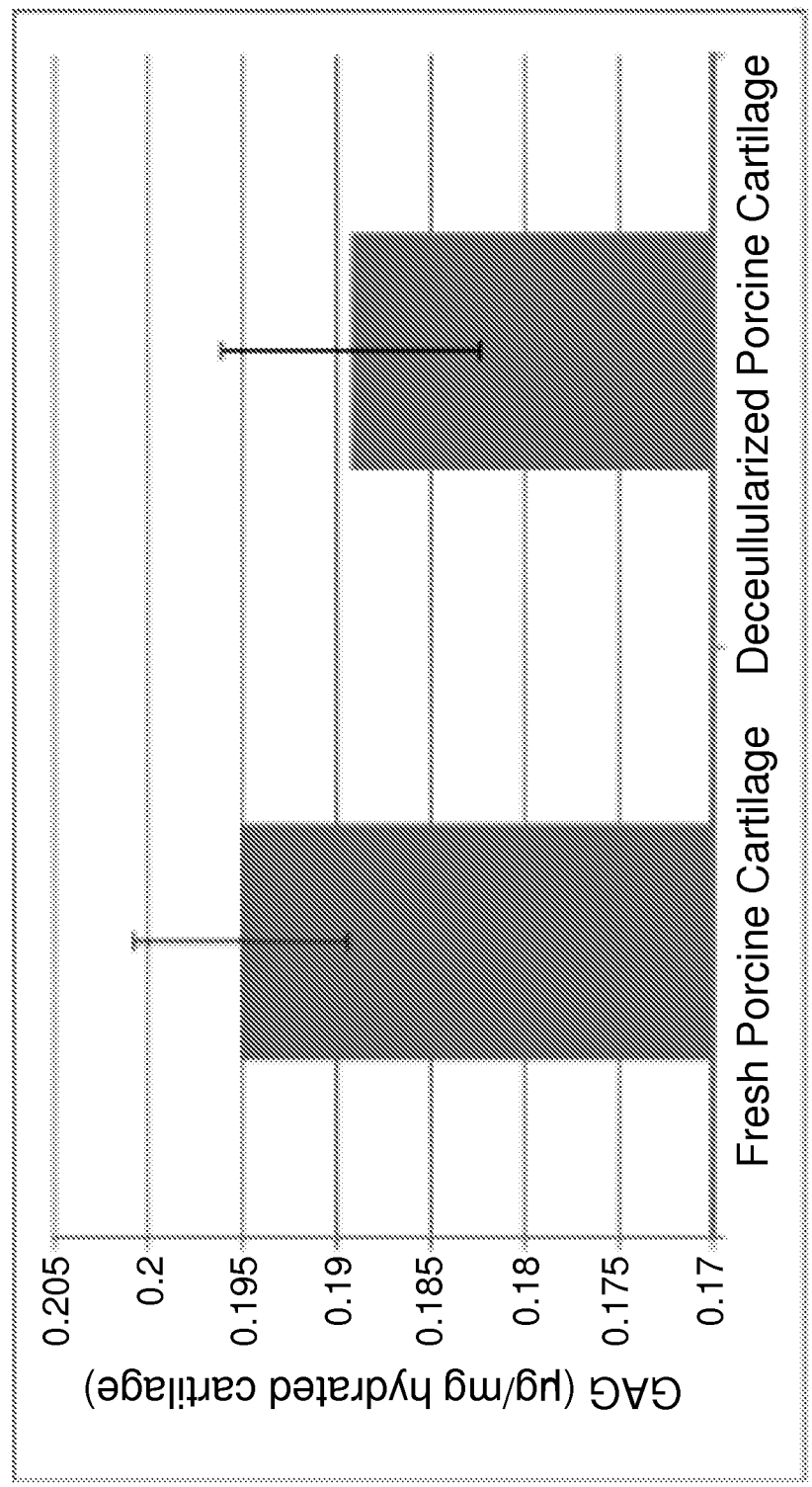
FIG. 2 illustrates the DMMB assay (Di-methyl methylene blue) data showing the GAG (glycosaminoglycans) content retention after decellularization in porcine cartilage.

Similar characterization was also conducted using porcine cartilage tissue after fragmentation, decellularization and powderization. FIG. 1 presents the picogreen data confirming an 89% decrease in the amount of double stranded DNA from the native to the decellularized porcine cartilage powder. FIG. 2 presents the DMMB assay results confirming that GAG content retention in decellularized porcine cartilage powder was greater than 90%.

In addition, native and DCC powder samples were analyzed for chemical composition changes using Transmission FTIR with the KBr pellet method. Transmission FTIR confirmed that no chemical composition change occurred during the decellularization process.

DCC Tissue Powder and their Influence on Rat Bone Marrow Stem Cell (rBMSC) Gene Expression Following DCC powder characterization, $2\times10^6$ rBMSCs at passage 4 (P4) were pelleted alone or with DCC fragments in 15 mL centrifuge tubes and cultured in standard chondrogenic medium with no growth factors for 7 days. Pellets (n=3) were harvested at Day 1 and Day 7 for gene expression analysis by reverse transcriptase polymerase chain reaction (PCR). Collagen II (COL2A1), Aggrecan (Acan), and SRY-box9 (Sox9) primers and glyceraldehyde-3 phosphate dehydrogenase (GAPDH) as an endogenous control were used to exam the expression level of these genes in the pellet culture samples. FIG. 3 demonstrated the relative gene expression of Col2A1 and Sox9 for pellet culture samples with and without DCC powder. Gene expression analysis of the pellet cultures with and without DCC revealed that Col2A1 expression was increased nearly two-fold at Day 7 with the addition of DCC to pellet culture (p<0.03) In addition, Sox 9 expression nearly tripled at Day 7 with the incorporation of DCC powder when compared to the control at the same time point. The increased gene expression revealed the ability of DCC powder to upregulate the chondrogenic markers Sox9 and Col2A1 in rBMSCs.

This pellet culture study will be repeated with greater sample sizes and additional chondrogenic markers. These cartilage tissue powders can be combined into 3D scaffolds for further function and structure characterization.

Through the characterization analysis, DCC powder has been shown to be useful for finding a true chondroinductive material that can provide microenvironmental cues and signaling to promote stem cell differentiation.

Characterization of the Powderized Decellularized Cartilage

Figure 6:
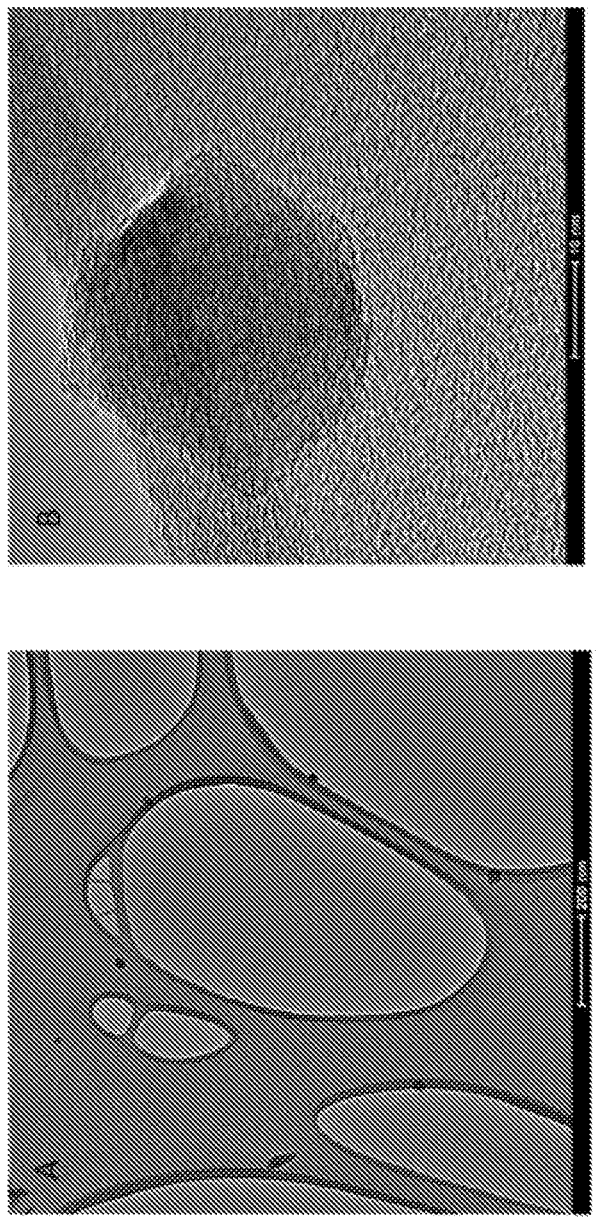
FIG. 6 illustrates a TEM image of ground decellualarized bovine cartilage having particle size of 20 nm after cryo-grinding cycles.

The cryopreserved and decellularized cartilage was ground using a freezer mill into heterogeneous particles. FIG. 4 presents light microscopy images showing the average particles size of 66.9 µm (micrometers) in decellularized porcine cartilage post cryogrinding. FIG. 5 presents light microscopy images showing the average particles size of 38.9 μm (micrometers) in decellularized porcine cartilage post cryogrinding. FIG. 6 presents the TEM (Transmission Electron Microscopy) images of ground decellularized bovine cartilage having 20 nm particles after cryogrinding cycles.

In one observation, the decellularized material, after cryogrinding, had heterogeneous particles ranging in size from 20 nanometers to 50 micrometers with the majority of the particles being less than 20 micrometers.

EXAMPLE 3

This example illustrates the use of the powderized decellularized cartilage and the characterization of the resulting paste, or gel, or hydrogel composite.

The ground (or powderized) decellularized tissue was solubilized in 0.1M HCl at a concentration of 10 mg DCC per 1 mL HCl. Pepsin was then added at a concentration of 1 mg/mL. The powderized DCC was digested in this solution for 1 day to 2 days, which length can be adjusted to give desirable rheological properties, i.e, the longer the solubilization period for the powderized DCC, as provided herein, the higher the yield stress from the resultant solution. After the digestion period, the solution containing the powderized DCC (SDCC) was brought back to physiological pH by adding 1M NaOH ($\frac{1}{10}^{th}$ of the original solution volume) and then back to osmolarity by adding 10×PBS ($\frac{1}{10}^{th}$ of the final neutralized volume). All steps for making SDCC were performed at room temperature at 21° C. The SDCC was then centrifuged at 10,000 RCF for about three minutes and the supernatant (the solubilized portion) and the slightly solubilized decellularized cartilage (SDCC) particulates were separated, with each of the two portions applicable for different approaches in making SDCC hydrogels.

SDCC Particle Based Cartilage Paste/Gel/Hydrogels

Decellularized cartilage powder can be processed to produce various cartilage hydrogels useful for tissue engineering. The present invention provides two non-limiting exemplary approaches for making hydrogels using solubilized DCC powder. After the solubilized DCC (SDCC) solution was prepared using the method as provided, the SDCC solution was first centrifuged at 10,000 RCF for about three minutes to separate the supernatant (the solubilized portion) and the slightly solubilized decellularized cartilage (SDCC) particulates that remained not fully solubilized at the bottom of the centrifuge tube. In the first approach, the "slightly solubilized" particles at the bottom of the tube are obtained and combined with methacrylated hyaluronic acid (MeHA), without photocrosslinking, to form a paste-like material that is easily injected/molded into a defect and which can be, if desired, crosslinked; or photocrosslinked, to form a gel (also called hydrogel). In the second approach, the solubilized portion is obtained and is reacted with glycidyl methacrylate to form methacrylated SDCC. This methacrylated SDCC can then be crosslinked or photocrosslinked into a hydrogel.

The following provides further details regarding the making and characterization of the various SDCC hydrogels provided in the present invention.

Figure 7:
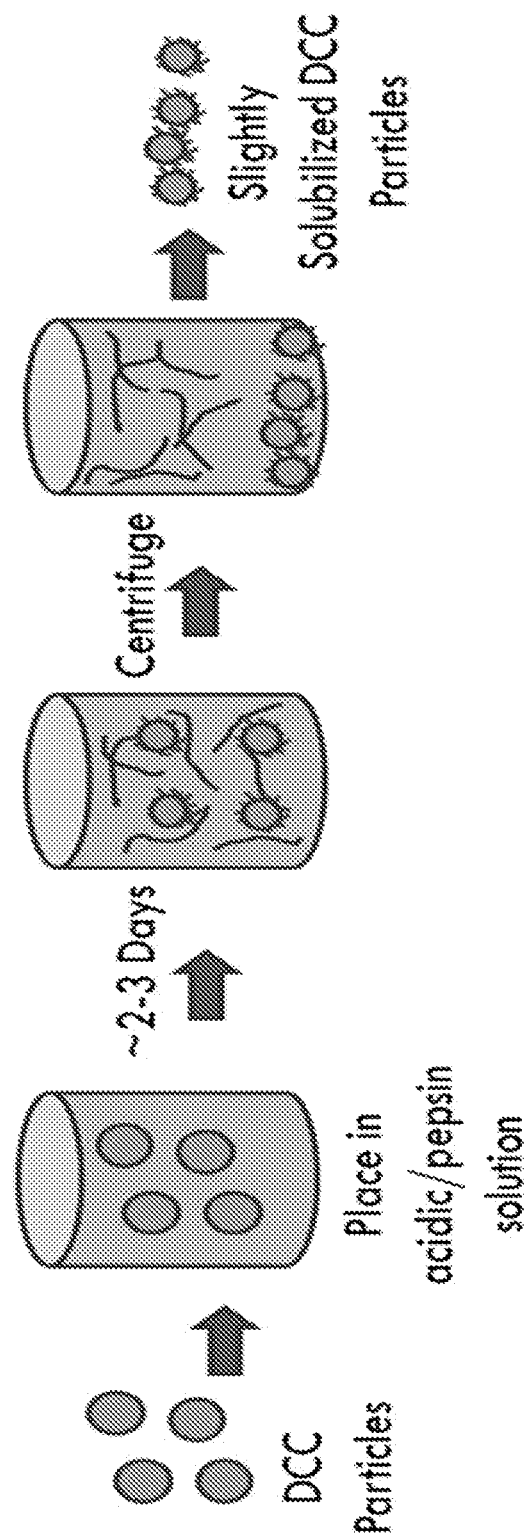
FIG. 7 illustrates the process of obtaining slightly solubilized DCC particles

SDCC Particulate/MeHA Composite Paste and Gel—the Use of the Slightly Solubilized Particles After solubilizing and centrifuging the powderized DCC solution, the supernatant (the solubilized portion) was removed while the SDCC particulates (the slightly solubilized particles at the bottom of the centrifuge tube) were retained for subsequent processing (FIG. 7). The SDCC particulates were then frozen and lyophilized for two days.

The slightly solubilized particles obtained after centrifuging can be combined with Methacrylated Hyaluronic Acid (MeHA) to create DCC:MeHA paste or gel at different ratios.

To make a paste, a desired concentration of SDCC particulate was weighed and mixed with MeHA.

To make a gel (also called hydrogel), for example, a gel comprising 15% w/v SDCC particulates and 15% w/v MeHA, after weighing out a desired concentration of SDCC particulate, 15% w/v MeHA was prepared in 1×PBS containing 0.05% (w/v) Irgacure photoinitiator. The MeHA and SDCC particulates mixture containing photoinitiator was placed in a 2 mm thick mold between glass slides and exposed to 312 nm UV light (Spectrolinker XL-1000; Spectronics Corp., Lincoln, Nebr.) for 15 min on each side, and an overall 30% w/v gel was formed.

Characterization of SDCC Particulate/MeHA Composite

1. Evaluating Yield Stress of SDCC Particulate/MeHA Paste Composite:

A yield stress is desirable for injectable/moldable materials so they do not flow after being placed in the defect. Traditional hydrogels have Newtonian fluid behavior and are prone to leaking from the defect site prior to crosslinking. Therefore a desirable yield stress of the hydrogel solution prior to crosslinking is an important characterization of the hydrogel.

The SDCC particulate MeHA composite gels as provided herein combined a traditional hydrogel material (MeHA) with SDCC particulates to create a "paste-like" material prior to photocrosslinking. The paste-like material is desirable because it can easily be molded into a defect and will not flow from the defect. Not only does adding SDCC particulates give the gels a yield stress, but they also surprisingly give cells sites of attachment without the need for incorporating cell adhesive peptides.

The testing of the presence of yield stress of the hydrogels was carried out using the methods described as following. Before photocrosslinking, the shear stress and viscosity of the samples (n=3) were measured over a shear rate sweep of 0.01-100 s$^{-1}$ using an AR-G2 rheometer (TA Instruments, Delaware) equipped with a 20 mm diameter plate at 37° C. The yield stresses of solutions exhibiting Herschel-Bulkley (H-B) characteristics were calculated by fitting the data using a 3 parameter fitting technique to the H-B equation (Eq. 1), where τ is the shear stress, $τ_0$ is the yield stress, k is the consistency index, γ is the shear rate, and n is the power law index.

$$\tau = \tau_0 + k(\gamma)^n \qquad \text{(Eq. 1)}$$

Figure 8:
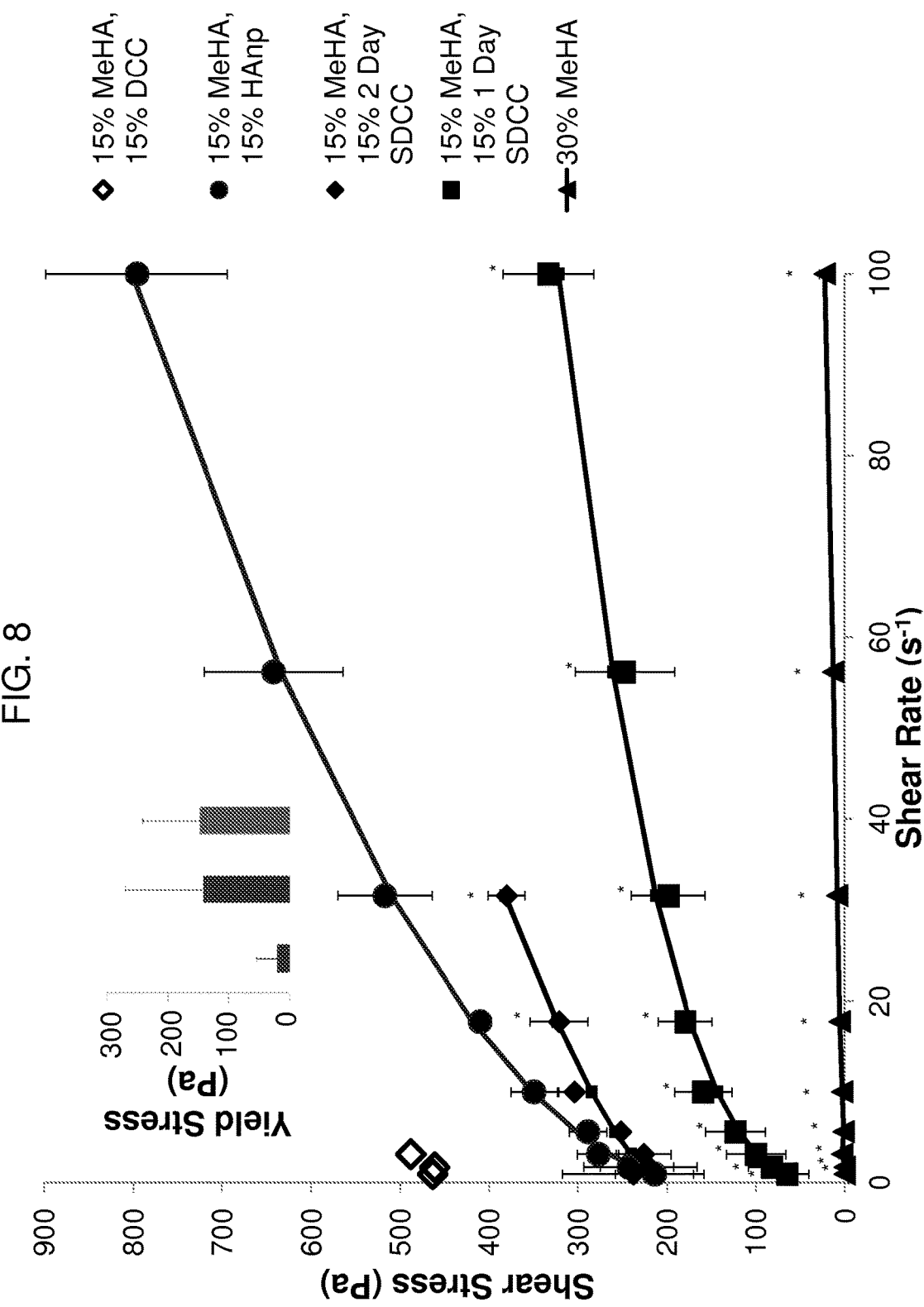
FIG. 8 illustrates the shear thinning profiles of SDCC particulate solutions (n=3). The data are means plus or minus standard deviation. "*" indicates significance from HAnp incorporated gels.
Figure 9:
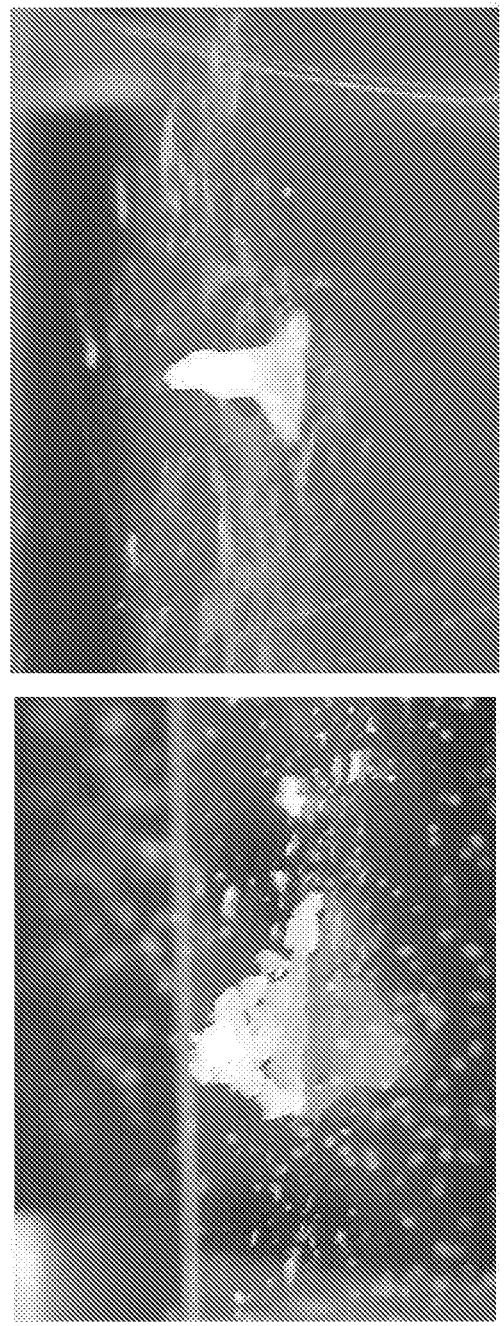
FIG. 9 illustrates the difference of the DCC observed before and after solubilization.
Figure 10:
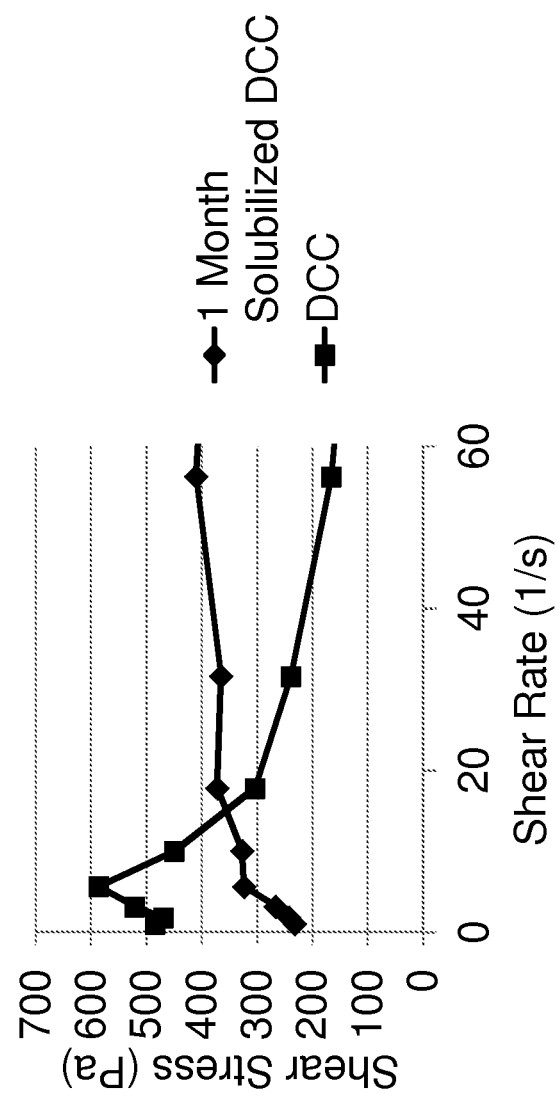
FIG. 10 illustrates the shear thinning profiles of 15% w/v solubilized DCC particles in comparison to non-solubilized DCC particles.

FIG. 8 illustrates the Shear Thinning profiles of SDCC particulate solutions obtained from the above said testing. In this testing, four gel samples and a control were applied and compared: (1) 15% MeHA:15% DCC, (2) 15% MeHA:15% HAnp, (3) 15% MeHA:15% 2 Day SDCC, (4) 15% MeHA:15% 1 Day SDCC, and (5) 30% MeHA as a control. HAnp is a gel system different from MeHA with confirmed yield stress. As shown in FIG. 8, the yield stress of particles solubilized for two days is comparable to the yield stress of the HAnp. The yield stress of particles solubilized for two days is higher than that of particles solubilized for one day only. Solubilized DCC particles have shear thinning behavior and exhibit yield stress compared to MeHA alone. DCC (non-solubilized DCC) particles alone are unable to be tested on the rheometer at shear rates above 5 s$^{-1}$, making evaluation of yield stress impossible. However, as shown in FIG. 9, the visual differences between the DCC and SDCC particulate gels are apparent that the SDCC particulate gels exhibit a paste-like quality with yield stress, the DCC gels crumble and are difficult to mold into a desired shape. FIG. 10 further presents the shear thinning profiles of 15% w/v SDCC in comparison to non-solubilized DCC. As shown in FIG. 8, the 15% w/v SDCC exhibits shear thinning behavior and has a yield stress before photocrosslinking, whereas 15% w/v DCC without solubilizing does not share those characterizations.

2. Mechanical Testing of SDCC Particulate/MeHA Gel after Photocrosslinking:

The photocrosslinked SDCC Particulate/MeHA hydrogel comprising 15% MeHA:15% SDCC (w/v) were compressed using a RSA-III dynamic mechanical analyzer (TA Instruments) at a rate of 0.005 mm/s until mechanical failure and the elastic modulus was calculated as the slope under the linear portion of the stress-strain curve. Several different gel compositions were tested as controls, which included 15% MeHA, 30% MeHA, and 15% MeHA:15% DCC. It was shown that 15% MeHA:15% SDCC gels had higher compressive moduli than the 15% MeHA gels, suggesting incorporating SDCC does not hinder mechanical performance.

3. Swelling of SDCC Particulate/MeHA Gel after Photocrosslinking:

Initial weights of photocrosslinked gels comprising 15% MeHA:15% SDCC were obtained and then the gels were swollen in PBS for 24 hours. The swollen weights were obtained and then the gels were frozen and lyophilized. The dry weight was recorded after lyophilization and the swelling degree (Q) was calculated as the ratio of swollen weight to dry weight. The swelling ratio was calculated as the total wet mass to dry mass.

Figure 11:
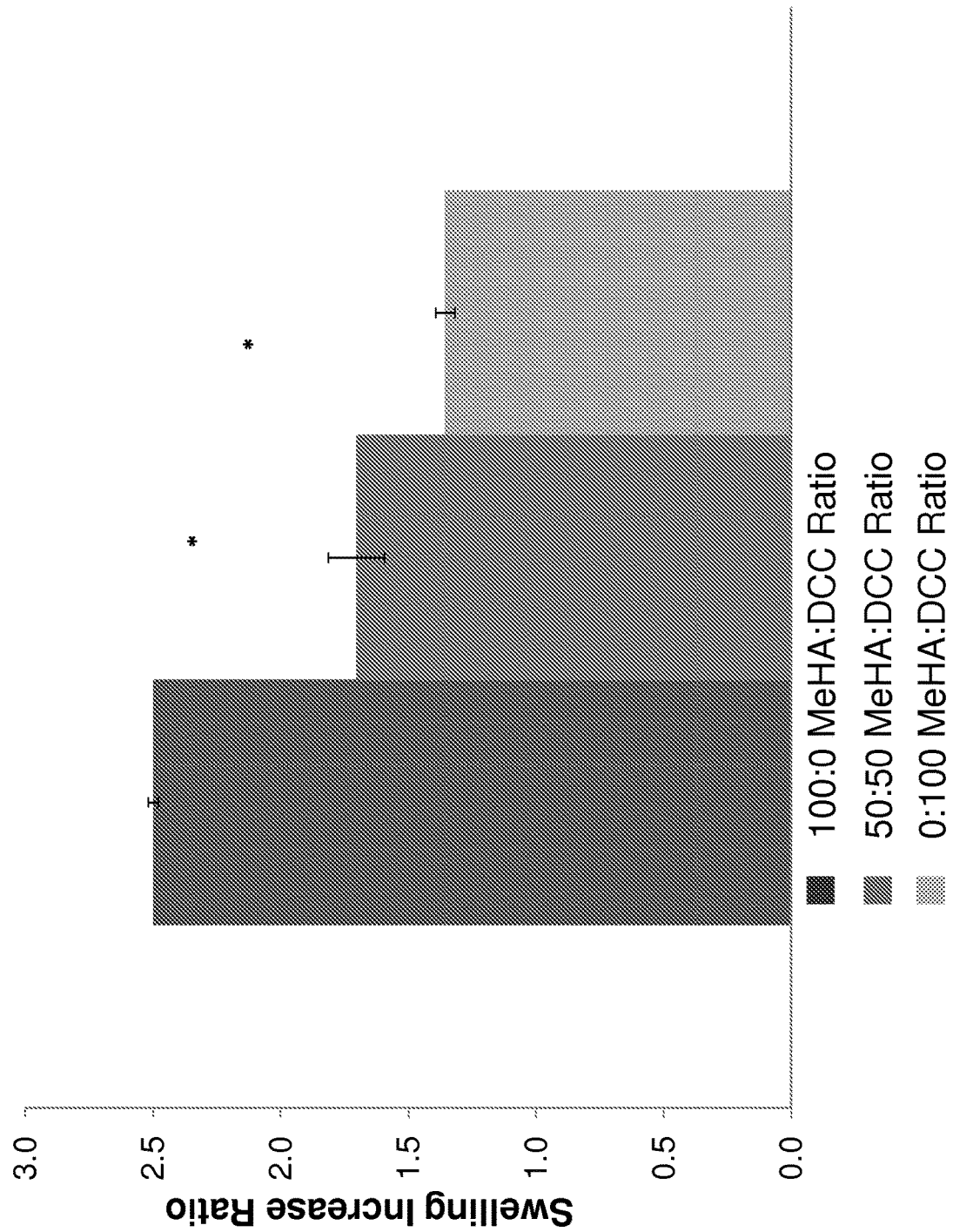
FIG. 11 illustrates the Swelling Increase Ratio comparison among DCC, DCC:MeHA (50:50) gel, and MeHA.

FIG. 11 illustrates the swelling ratios for MeHA:DCC composites: MeHA control (100:0 MeHA: DCC), DCC: MeHA gels (50:50), and DCC (0:100 MeHA: DCC), with all gels being 20% w/v. The swelling ratio is calculated by the ratio of the swollen weight to initial weight, such that a swelling ratio of 1 represents no swelling of the hydrogel. As shown in FIG. 11, MeHA:DCC gels have very limited swelling compared to MeHA control, and the higher the amount of DCC in the gel, the lower the swelling ratio for the DCC:MeHA hydrogel.

Figure 12A:
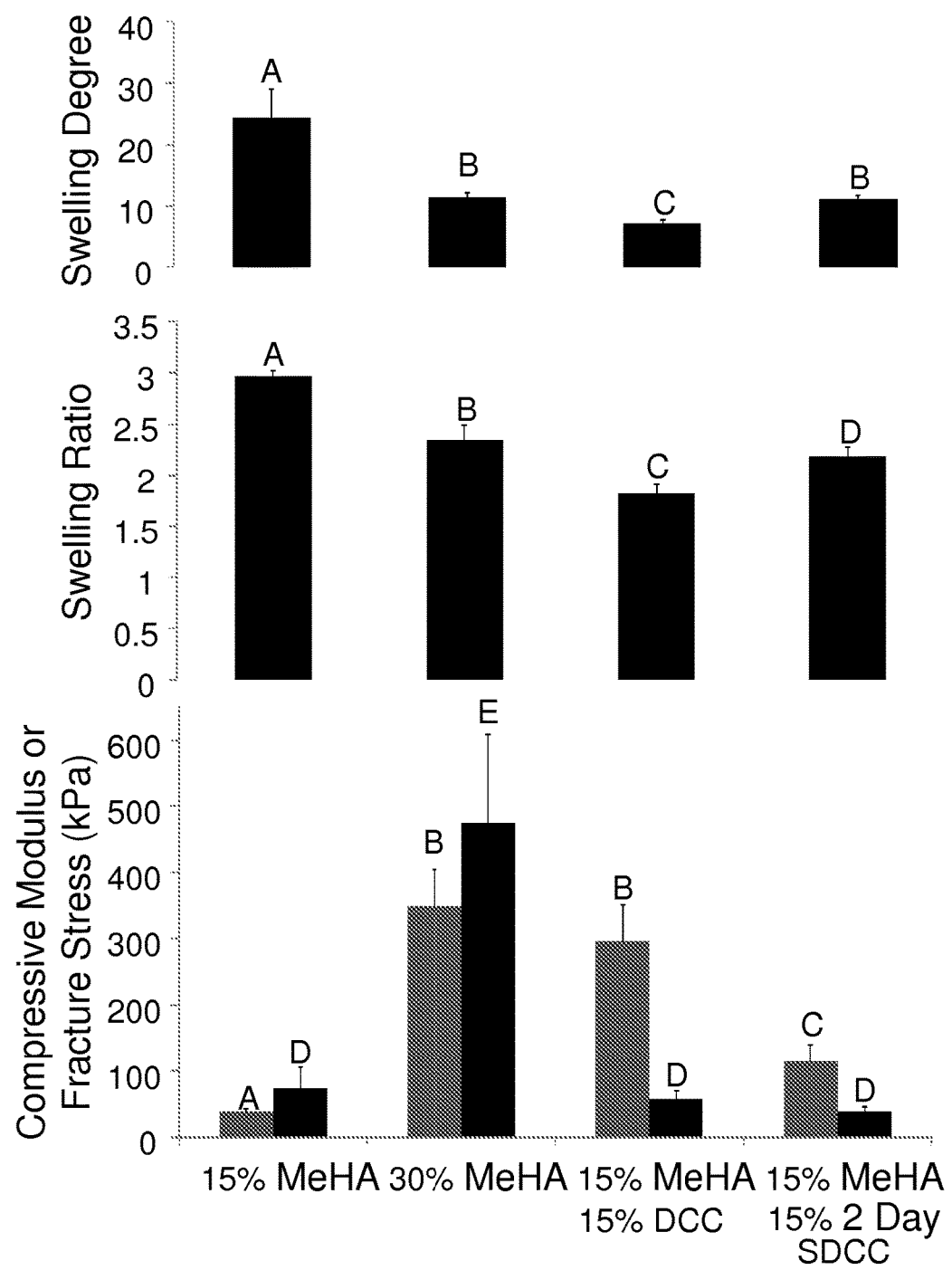
FIG. 12 A illustrates (A) the mechanical features including swelling degree, swelling ratio, compressive modulus, and fracture stress of various gel formulations; and (B) the visual difference in the ability in forming a three dimensional shape of various gel formulations. Letters indicate samples with no statistical significance (i.e., samples with different letters mean the samples are significantly different).
Figure 12B:
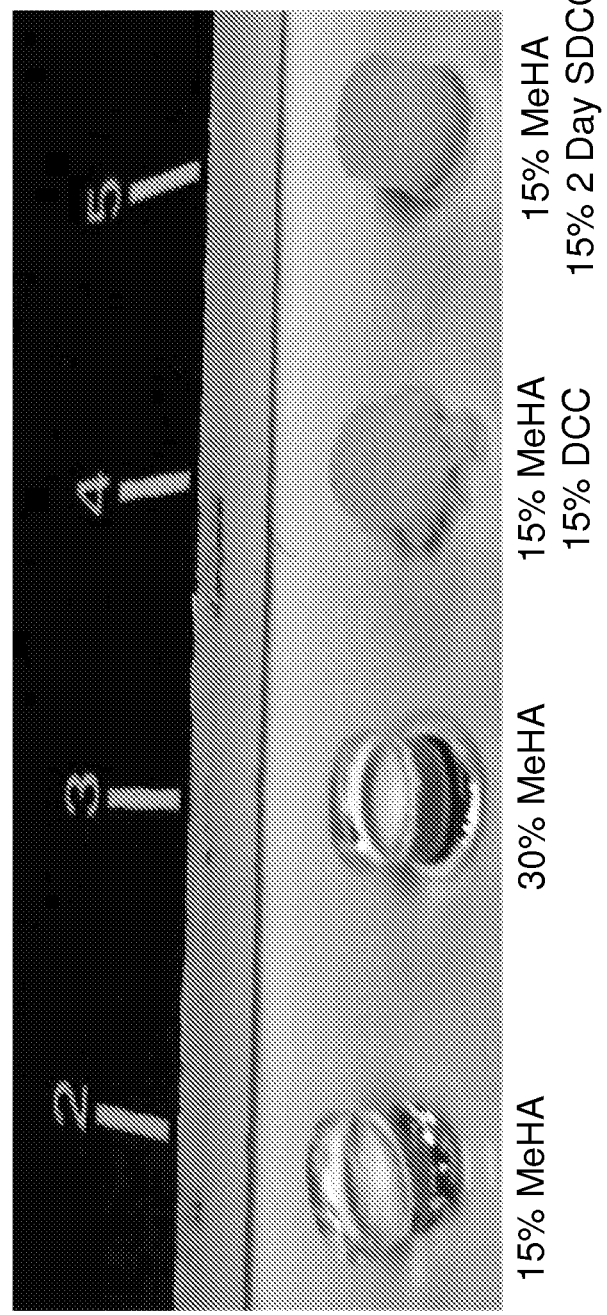

Further, FIG. 12A illustrates swelling degree, swelling ratio, compressive modulus, and fracture stress of various gel formulations, including, 15% MeHA, 30% MeHA, 15% MeHA:15% DCC, and 15% MeHA:15% 2 Day SDCC. Swelling degree, swelling ratio, compressive modulus, and fracture stress are parameters describing hydrogel performance. The swelling degree is calculated by the ratio of the swollen weight to the dry weight of the gel. The swelling ratio is calculated as described above. As shown in FIG. 12A, 30% MeHA and 15% MeHA:15% DCC have no statistical difference in compressive modulus; whereas the compressive modulus for 15% MeHA, 15% MeHA:15% DCC (or 30% MeHA) and 15% MeHA: 15% 2 Day SDCC are significantly different. The compressive modulus of the 15% MeHA: 15% 2 Day SDCC gels are less than that of 15% MeHA:15% DCC (or 30% MeHA), but higher than that of 15% MeHA. As further shown in FIG. 12, the swelling degree of the 30% MeHA gel is the same as the 2 Day SDCC particulate gel, even though the 30% MeHA gel contains more crosslinks. Also, the swelling degree and ratio of the 2 day SDCC particulate gels are less than that of 15% MeHA. The comparison in various parameters suggests that the SDCC gel as provided herein has the mechanical properties required in the native environment of cartilage tissue. Certainly different applications of the SDCC gels may require different characteristics, and these characteristics can be achieved by altering the amount of SDCC in the gel composition, and/or the amount of MeHA, and/or the ratio between the two components. The visual difference in the ability in forming a designed shape of these gel formulations is shown in FIG. 12B, and the observation that 15% MeHA: 15% 2 Day SDCC performs much better in forming shapes than 15% MeHA:15% DCC is consistent with the measurements of the various parameters described above.

MeSDCC Hydrogels Made from the Solubilized Portion of SDCC

After solubilizing and centrifuging the powderized DCC solution, the solubilized portion (supernatant) of the SDCC was isolated.

Figure 13:
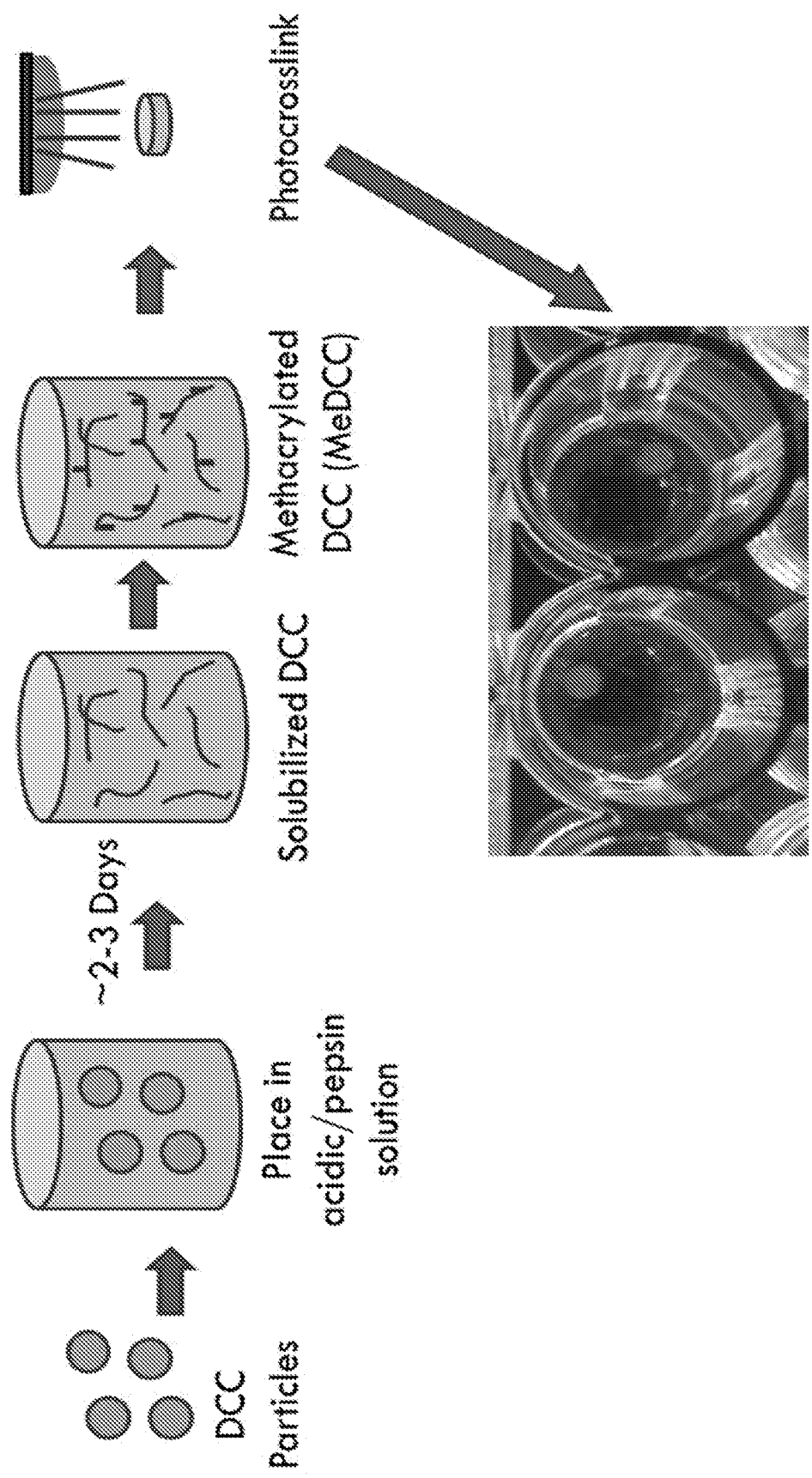
FIG. 13 illustrates the process of forming cartilage hydrogels by methacrylating and photocrosslinking solubilized DCC.

The supernatant portion of the SDCC was stirred at 200 rpm. The amount (mg) of DCC material in this supernatant portion was calculated based on the initial concentration of the SDCC solution, and the weight of the "slightly solubilized" particles at the bottom of the centrifuge tube that was removed. As such, the concentration of the supernatant portion of the SDCC was suggested to be about ¼ of the total concentration of the original digesting solution. The volume of the stirring SDCC solution was doubled with acetone. Then 20 fold molar excess glycidyl methacrylate, triethylamine, and tetrabutyl ammonium bromide were added to the solution for a reaction. The molar excess was calculated based on an assumption that one glycidyl methacrylate group reacts to one monomer that is present in the solution and that all monomers are hyaluronic acid. The reaction continued with stirring for 5 days, resulting in a methacrylated decellularized cartilage solution (MeSDCC). The MeSDCC solution is then precipitated in excess acetone, dialyzed for 2 days in DI water, and then lyophilized into a dry powder. To make a gel, a desired amount of the powder was weighed and then mixed with 1×PBS solution containing 0.05% (w/v) Irgacure photoinitiator. To provide an example, 15% w/v MeSDCC was used herein, although alternate concentrations may applicable as well. The MeSDCC solution was placed in a 2 mm thick mold between glass slides and exposed to 312 nm UV light (Spectrolinker XL-1000; Spectronics Corp.) for 15 min on each side for crosslinking. The gels formed were cut using a 3 mm biopsy punch. FIG. 13 illustrates the processes of forming Methacrylated SDCC hydrogels.

Characterization of MeSDCC Hydrogels

The MeSDCC hydrogels have high stiffness and low swelling, which are ideal material properties for cartilage hydrogels.

1. Mechanical Testing of MeSDCC Gels after Photocrosslinking:

The MeSDCC hydrogels were compressed using a RSA-III dynamic mechanical analyzer (TA Instruments) at a rate of 0.005 mm/s until mechanical failure and the elastic modulus was calculated as the slope under the linear portion of the stress-strain curve. The elastic modulus was on average 725 kPa, which is close in magnitude to native cartilage matrix.

SDCC Particle Based Cartilage Paste/Gel/Hydrogels and Cell Attachment

Rat bone marrow stem cells (P2) were seeded on top of gels comprising 12.5% MeHA:12.5% DCC. 25% MeHA was used as a control. The DCC was cryoground, mixed with the MeHA, and photocrosslinked prior to cell seeding. The rBMSCs were seeded at a density of 100,000 cells/cm$^2$ in a 96 well plate and fed with α-MEM. One day after seeding, gel samples were removed from the well and cell attachment was observed on 12.5% MeHA:12.5% DCC gel with scanning electron microscopy (SEM) or with PlasDIC.

Figure 14A:
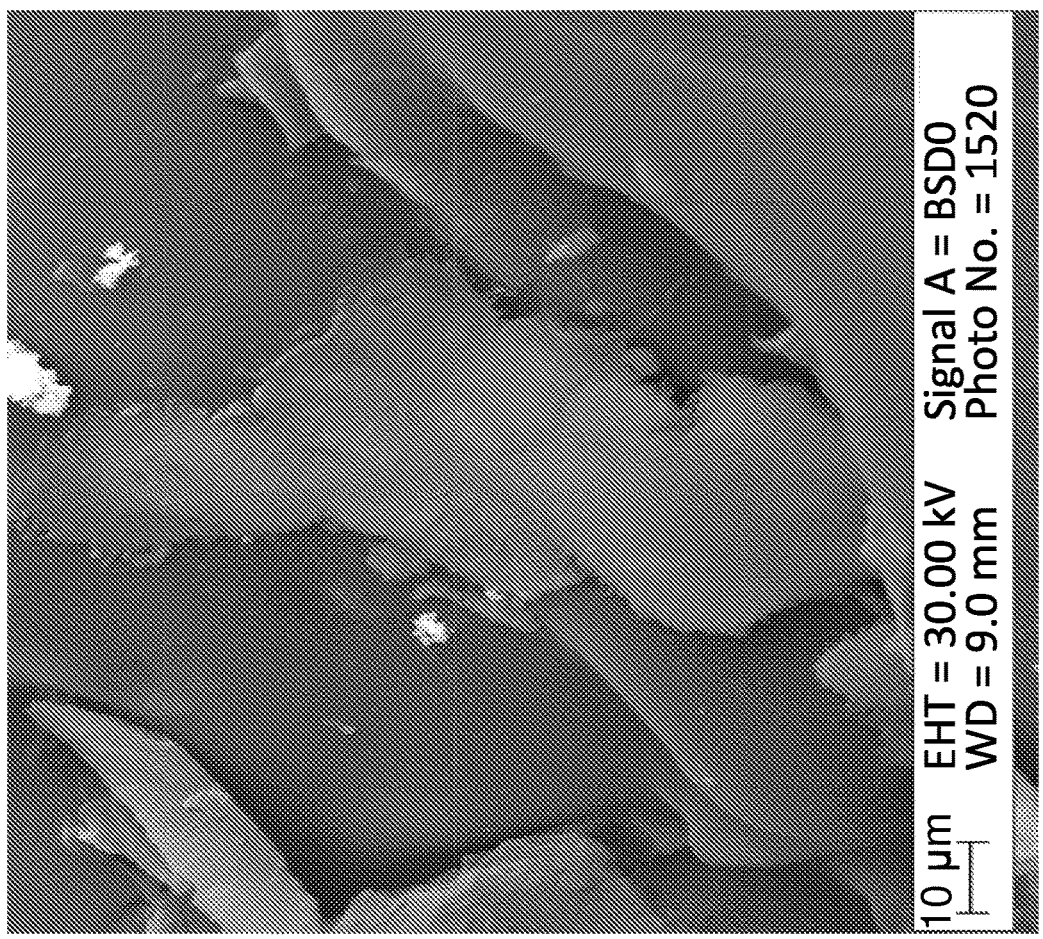
FIGS. 14 A, B, and C are photographs illustrating magnified images of cartilage hydro gels.
Figure 14B:
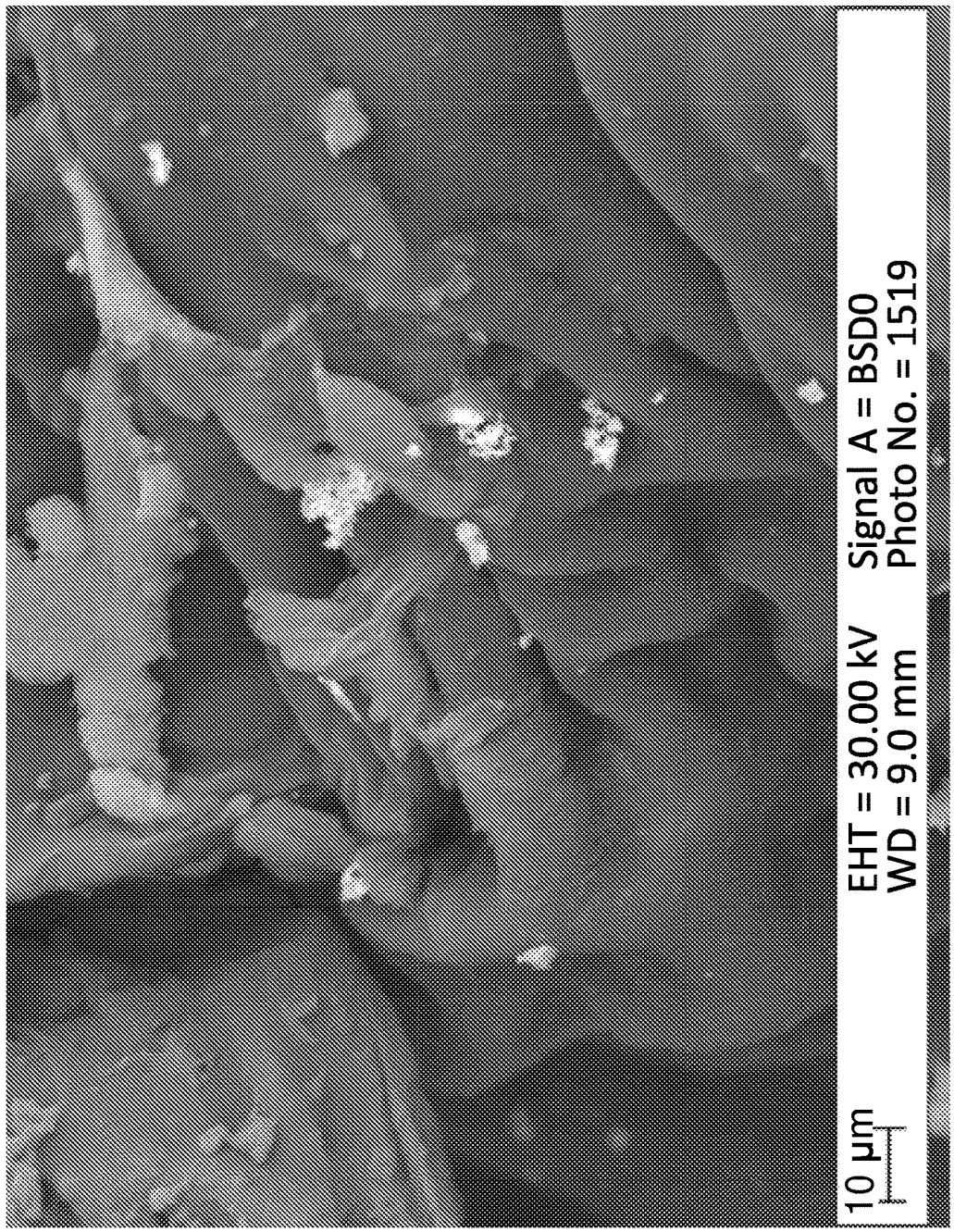
Figure 14C:
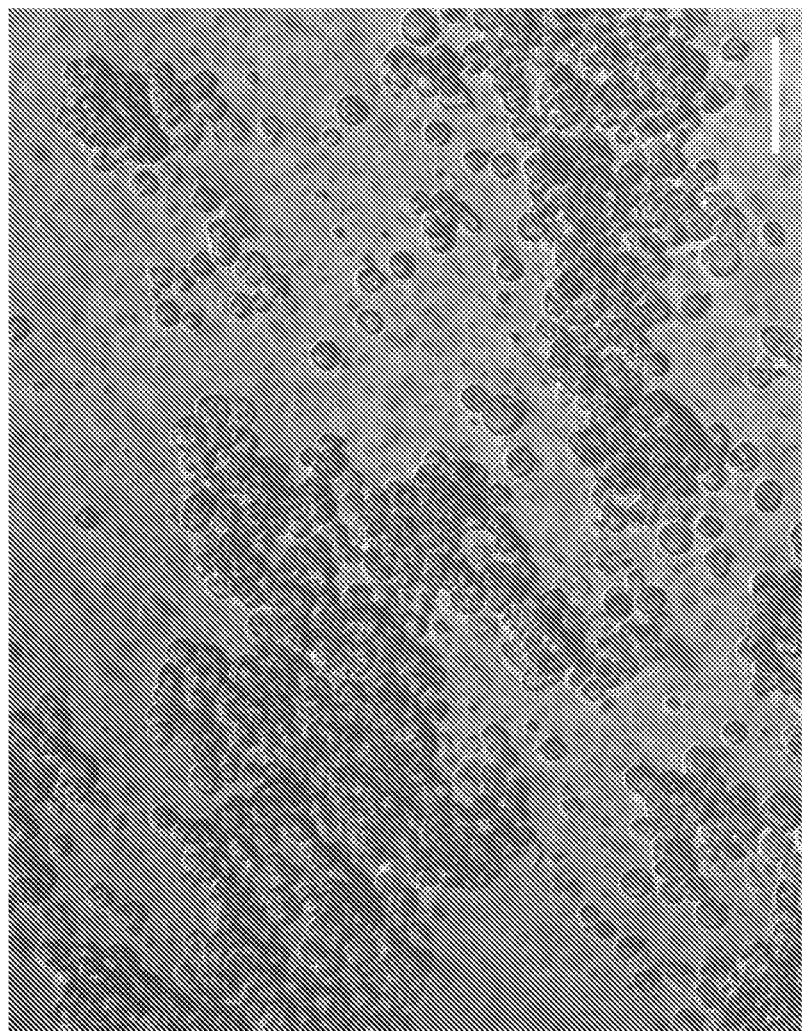

FIG. 14A illustrates the SEM images of rBMSCs seeded on 12.5% MeHA:12.5% DCC gel after one day of culture. The cells, as pointed out by the arrows in FIG. 14A, are shown to have a flattened and spread out morphology and are attaching to the gel matrix. In contrast, in FIG. 14B, a PlasDIC image of rBMSCs seeded on c after one day of culture, shows that the seeded cells have retained a rounded shape and are not spreading out and attaching to the gel. It was surprising to observe that the addition of the DCC powder to the 12.5% MeHA hydrogel facilitated cell attachment even though the hydrogel contained no added cell adhesive peptides, whereas the 25% MeHA gel did not demonstrate cell attachment as expected. This cell attachment is an essential step leading to subsequent events, such as cell migration, and eventually tissue regeneration.

EXAMPLE 4

This example illustrates the microsphere scaffolds in contacting with the decellularized cartilage tissue powder and the methods of making such scaffolds.

DCC Coated Microsphere Scaffolds

To create homogenous PLGA (poly(lactic-co-glycolic acid) microsphere based scaffolds, 20% w/v PLGA was weighted. Uniform microspheres were produced using the Precision Particle Fabrication technique. The PLGA solution was transferred to a syringe and loaded into a syringe pump for microsphere fabrication. The polymer stream was acoustically excited using an ultrasonic transducer (Branson Ultrasonics, Danbury, Conn.) controlled by a waveform generator (model 33220A; Agilent Technologies, Santa Clara, Calif.), resulting in regular jet instabilities that produced uniform polymer droplets. An annular carrier stream (~0.5% PVA w/v in distilled water) surrounding the droplets was produced using a nozzle coaxial to the needle. The emanated polymer/carrier streams flowed into a beaker containing a collection solution of 0.5% PVA. The acoustic excitation, polymer flow rate, and carrier solution flow rate are all adjustable as desired. To extract the solvent, incipient polymer droplets were stirred for 3-4 h. Subsequently, the hardened microspheres were filtered and rinsed with distilled water to remove residual PVA. Finally, microspheres were lyophilized (Freezone; Labconco benchtop model, Kansas City, Mo.).

Scaffolds were assembled by flowing rinsed and lyophilized microsphere suspensions into a cylindrical mold. Then microspheres were physically attached to form a continuous scaffold using ethanol treatment. The microspheres were rinsed with ethanol: acetone (95%:5%) solution, and then soaked in the ethanol: acetone (95%:5%) solution for a time determined by PLGA molecular weight. Generally, the larger the molecular weight of PLGA, the longer the sintering time to improve the mechanical characteristics of the scaffolds. In one example, the scaffolds in the molds were lyophilized for approximately 48 hours. Then the scaffolds were removed from the molds.

To make Decellularized cartilage powder (DCC) coated microsphere scaffolds, the sintered PLGA scaffolds were placed in solubilized DCC solution (SDCC). In one example, the SDCC was 20% w/v, i.e., 20 mg DCC per 1 ml HCl. 1 mg pepsin/ml HCl was also added to the solution. The sintered PLGA scaffolds were allowed to soak in solubilized DCC solution for approximately 5 minutes, which time period can be adjusted for PLGA molecular weight and scaffold size. While the scaffolds were in the solution, 1 M NaOH and 10×PBS was added to raise pH above 7. After further soaking the scaffolds for about another 5 minutes (time period can be adjusted accordingly), the scaffolds removed from the solubilized DCC solution were lyophilized for approximately 48 hours.

Morphological and physical characterization of the scaffolds revealed that microsphere matrices were porous and well connected, and with desired compressive stiffness.

DCC Encapsulated Microsphere Scaffolds

To create DCC encapsulated microsphere scaffolds, microspheres encapsulating DCC were first made. In one example, a 20 w/v % PLGA solution was prepared by mixing 2 g PLGA per 10 mL dimethylenecholoride. At the same time, a 20 w/v % solubilized DCC solution was made by mixing 20 mg DCC/1 mL 0.1 M HCl with the presence of 1 mg pepsin/mL 0.1 M HCl. The SDCC solution was incubated with slow rocking at room temperature for approximately 24 hours. At the end of the 24 hours, an adjusted amount of 1M NaOH and 10×PBS were added to raise pH in the solution to approximately 7.4 (physiological pH). The amount of above ingredients or concentrations can all be adjusted depending on a particular use and the targeted amount of DCC.

In one example, the SDCC solution was combined with PLGA solution at a 50:50 volume ratio. The mixed DCC/PLGA solution was used to fabricate microspheres using a precision particle fabrication technique as described above. The mixed solution was transferred to a syringe and loaded into a syringe pump. The polymer stream was acoustically excited using an ultrasonic transducer (Branson Ultrasonics, Danbury, Conn.) controlled by a waveform generator (model 33220A; Agilent Technologies, Santa Clara, Calif.), resulting in regular jet instabilities that produced uniform polymer droplets. An annular carrier stream (~2% w/v PVA in distilled water, preferably cold) surrounding the droplets was produced using a nozzle coaxial to the needle. The emanated polymer/carrier streams flowed into a beaker containing a collection solution of 5% PVA. The acoustic excitation, polymer flow rate, carrier solution flow rate, and carrier and collection solution concentration are all adjustable as desired. The acoustic excitation and adjustable carrier flow rate are related to the creation of homogeneous sized particles. To adjust the size of the microspheres, the acoustic excitation and flow rates of both the polymer solution and carrier solution can be adjusted. Subsequently, the hardened microspheres were filtered and rinsed with distilled water to remove residual PVA. Finally, microspheres were lyophilized (Freezone; Labconco benchtop model, Kansas City, Mo.). The microspheres obtained using the above process have encapsulated DCC.

Scaffolds were assembled by flowing rinsed and lyophilized microsphere suspensions into a cylindrical mold. Then microspheres were physically attached to form a continuous scaffold using ethanol treatment. The microspheres were rinsed with an ethanol: acetone (95%:5%) solution, and then soaked in the ethanol: acetone (95%:5%) solution for about 90 minutes. Generally, the larger the molecular weight of PLGA, the longer the sintering time to improve the mechanical characteristics of the scaffolds. In one example, the scaffolds in the molds were lyophilized for approximately 48 hours. Then the scaffolds were removed from the molds.

Morphological and physical characterization of the scaffolds revealed that microsphere matrices were porous and well connected, with desired compressive stiffness.

EXAMPLE 5

Materials and Methods

Figure 15:
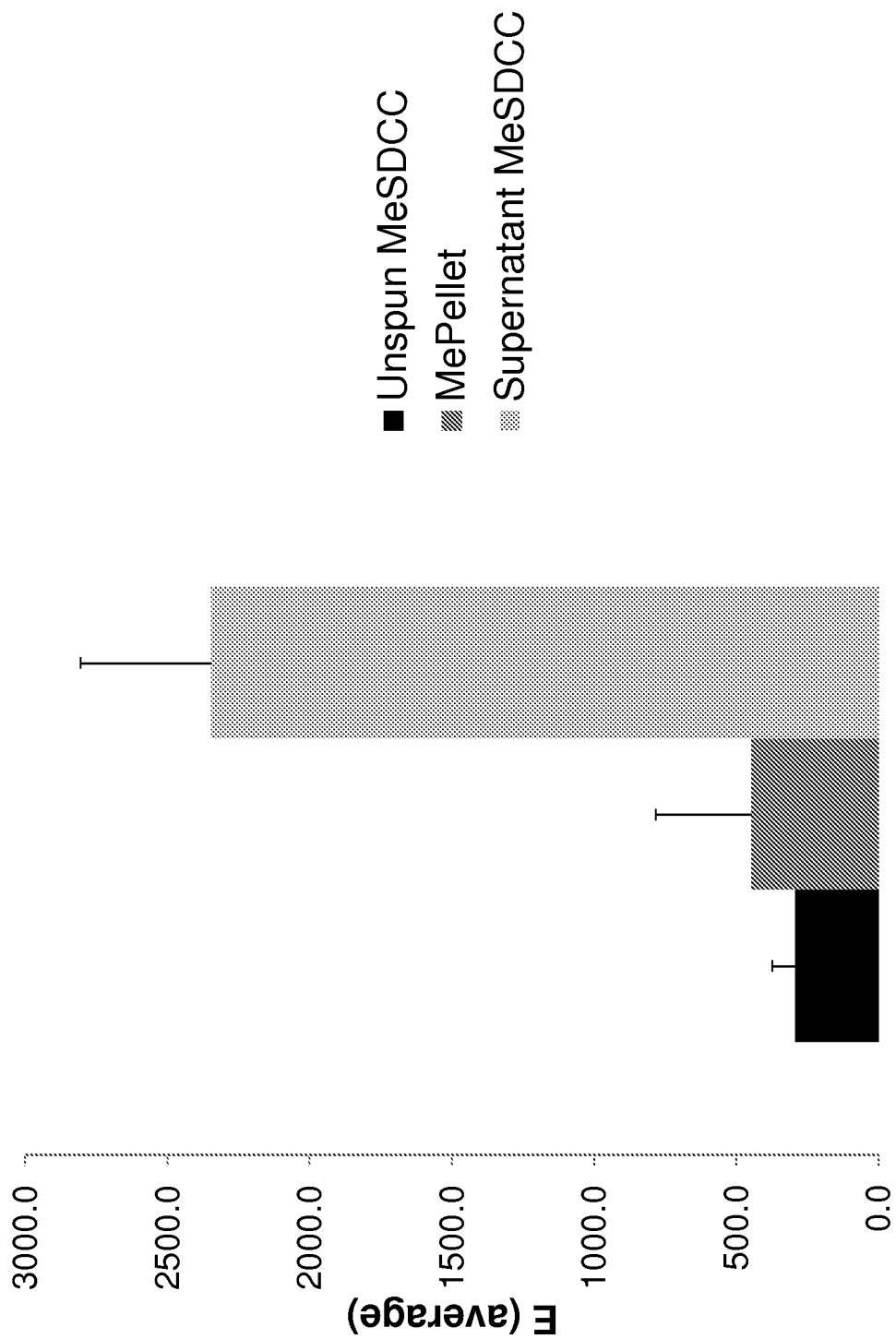
FIG. 15 illustrates the difference in mechanical properties between unspun MeSDCC, Me Pellet, and Supernatant Me SDCC.
Figure 16:
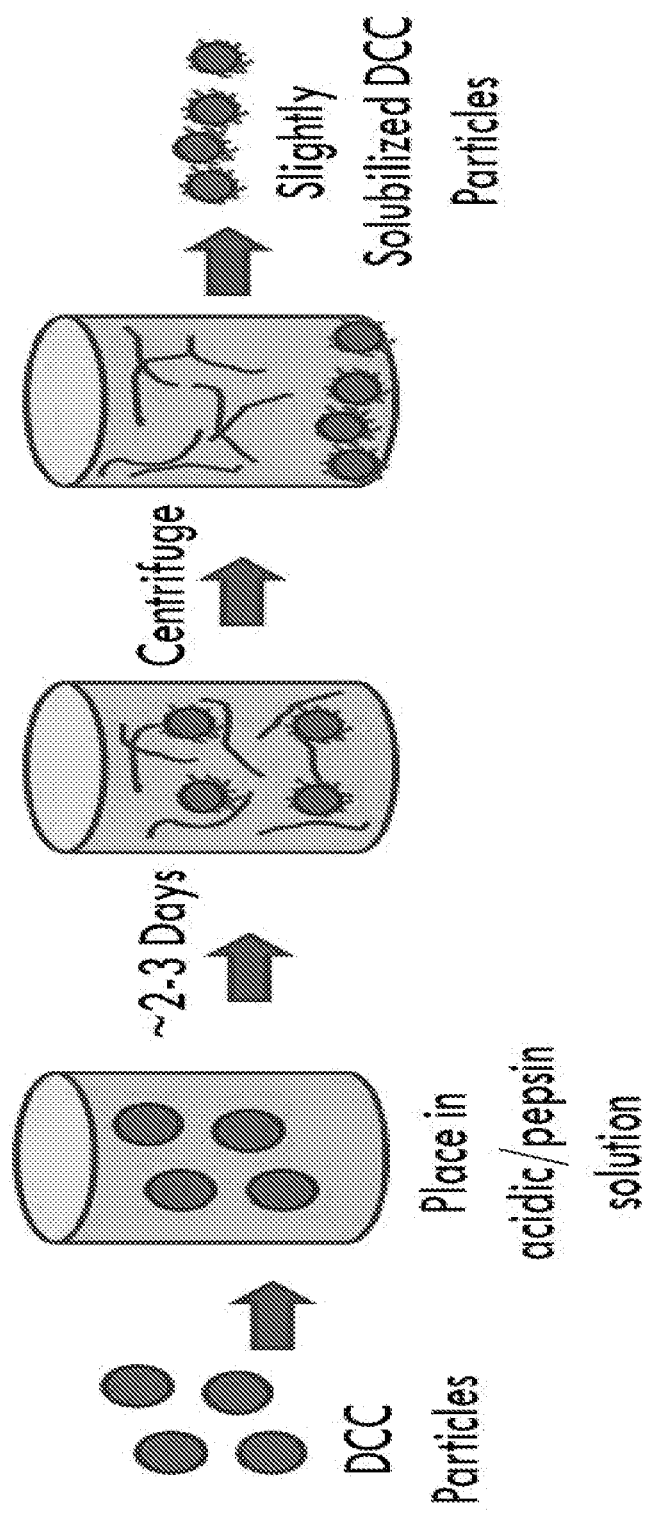
FIG. 16 illustrates one embodiment of making Me SDCC particles.

This experiment was used to determine the best way to process MeSDCC. As noted below (FIG. 13), the DCC particles are first solubilized for 2-3 days. After 2-3 days, they can either be methacrylated right away (unspun MeSDCC in FIG. 15) or the solubilized DCC solution can be centrifuged to remove particulates (as with the processing of the SDCC pellet (FIG. 16).

Results and Conclusions

If the particles from the solubilized solution (i.e., the particles at the end of the process in FIG. 16), are methacrylated, a Young's modulus similar to that of unspun MeSDCC (FIG. 15) is obtained. However, if the supernatant from the centrifuged material in FIG. 16 is methacrylated, the Young's modulus of the gel increases from the unspun or methacrylated SDCCpellet gels (FIG. 15). Currently only the supernatant of the centrifuged solution is being used to make MeSDCC.

EXAMPLE 6

Figure 17:
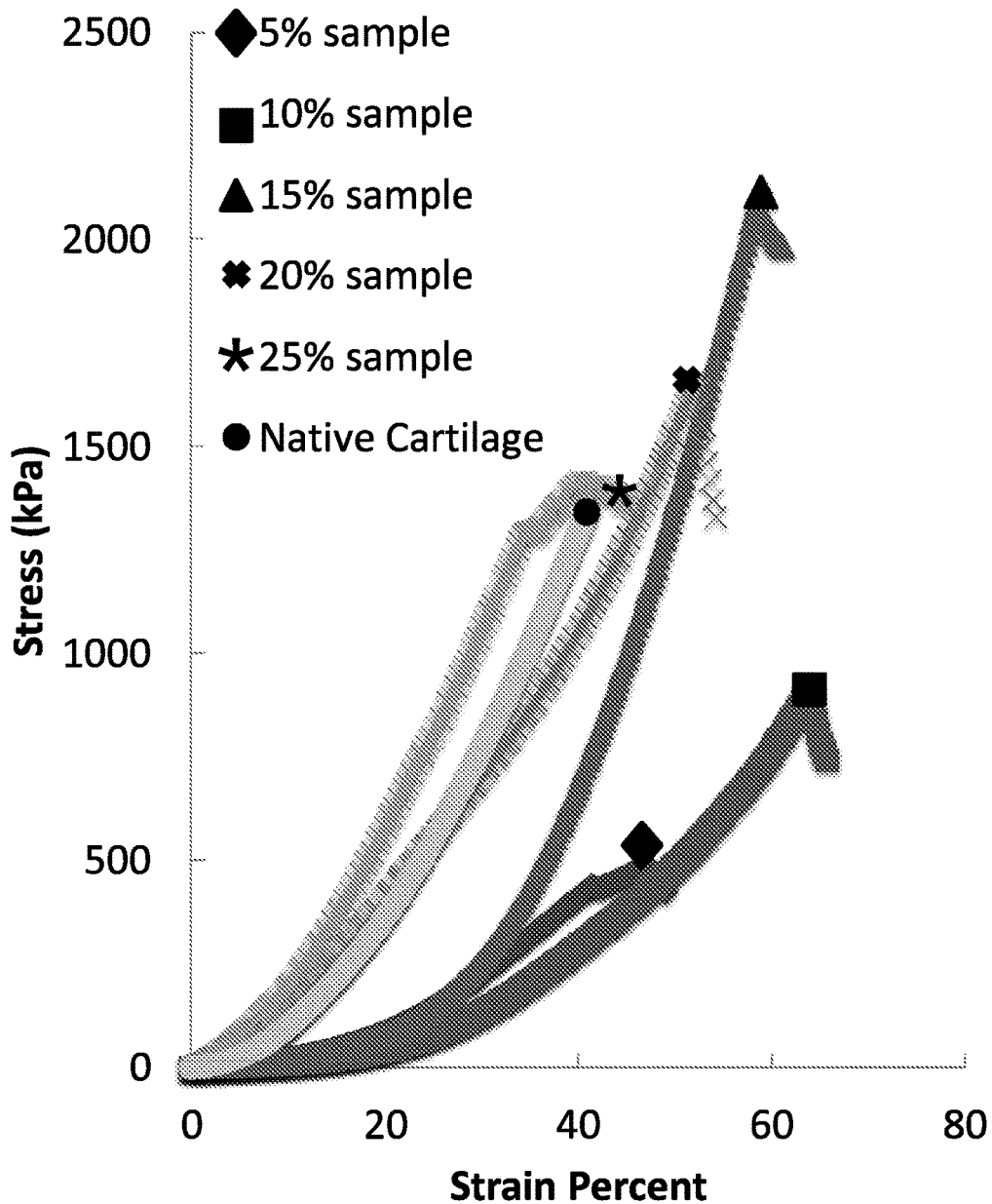
FIG. 17 illustrates adjusting the mechanical properties based on concentration of MeSDCC.

This experiment, examined how changing the concentration of MeSDCC affected the mechanical properties of the UV crosslinked gels. These properties were also compared to native cartilage. In general, increasing the concentration of MeSDCC increased the slope of the stress strain curve of MeSDCC (i.e. producing more stiff gels and thus, producing a higher Young's modulus) (FIG. 17). Additionally, the stress strain profile of 20% MeSDCC was the closest to native cartilage (and interestingly, native cartilage has an approximate dry content of 20%) (FIG. 17).

EXAMPLE 7

Figure 18:
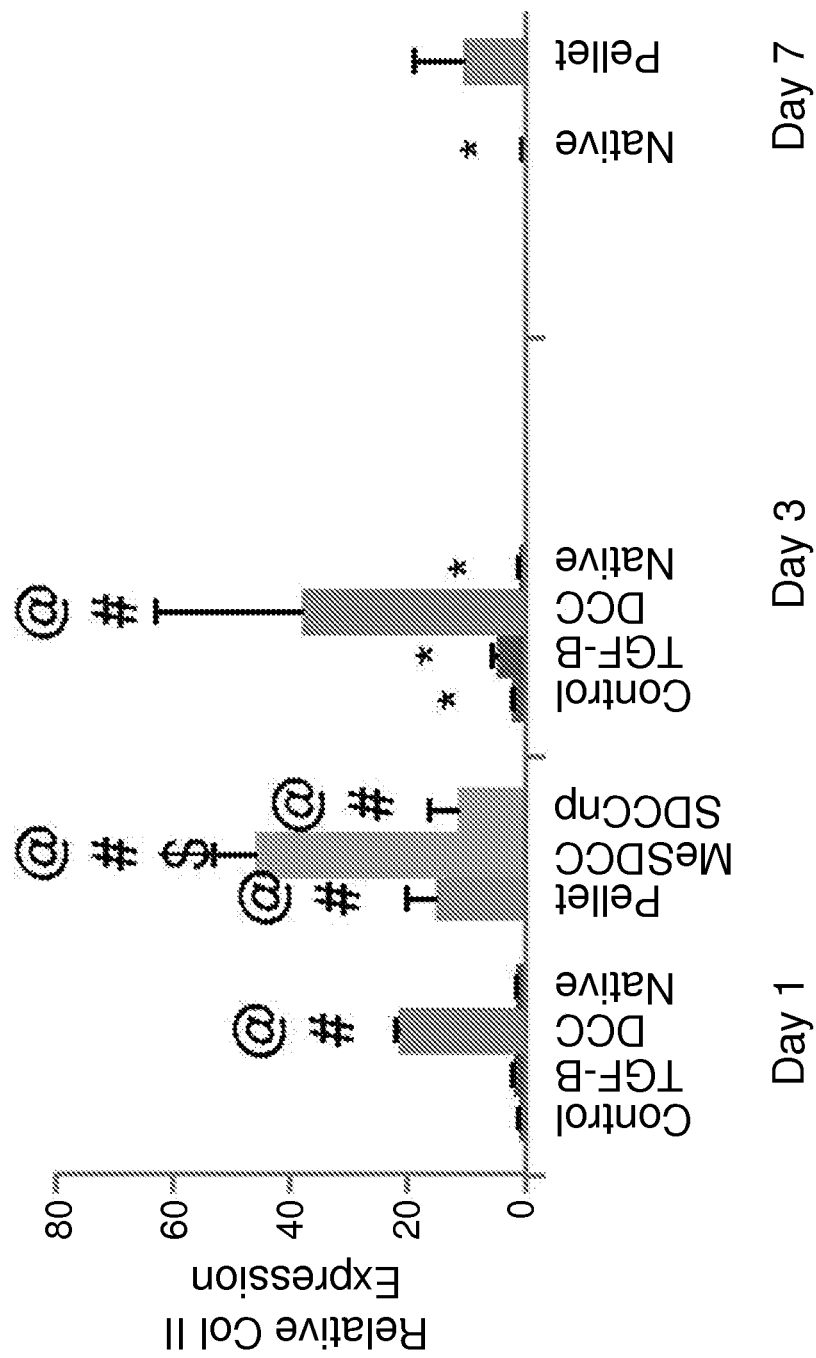
FIG. 18 illustrates the relative expression of Col II in the groups of control, TGF-B, DCC, Native, SDCC, Pellet, Me SDCC, and SDCCnp.
Figure 19:
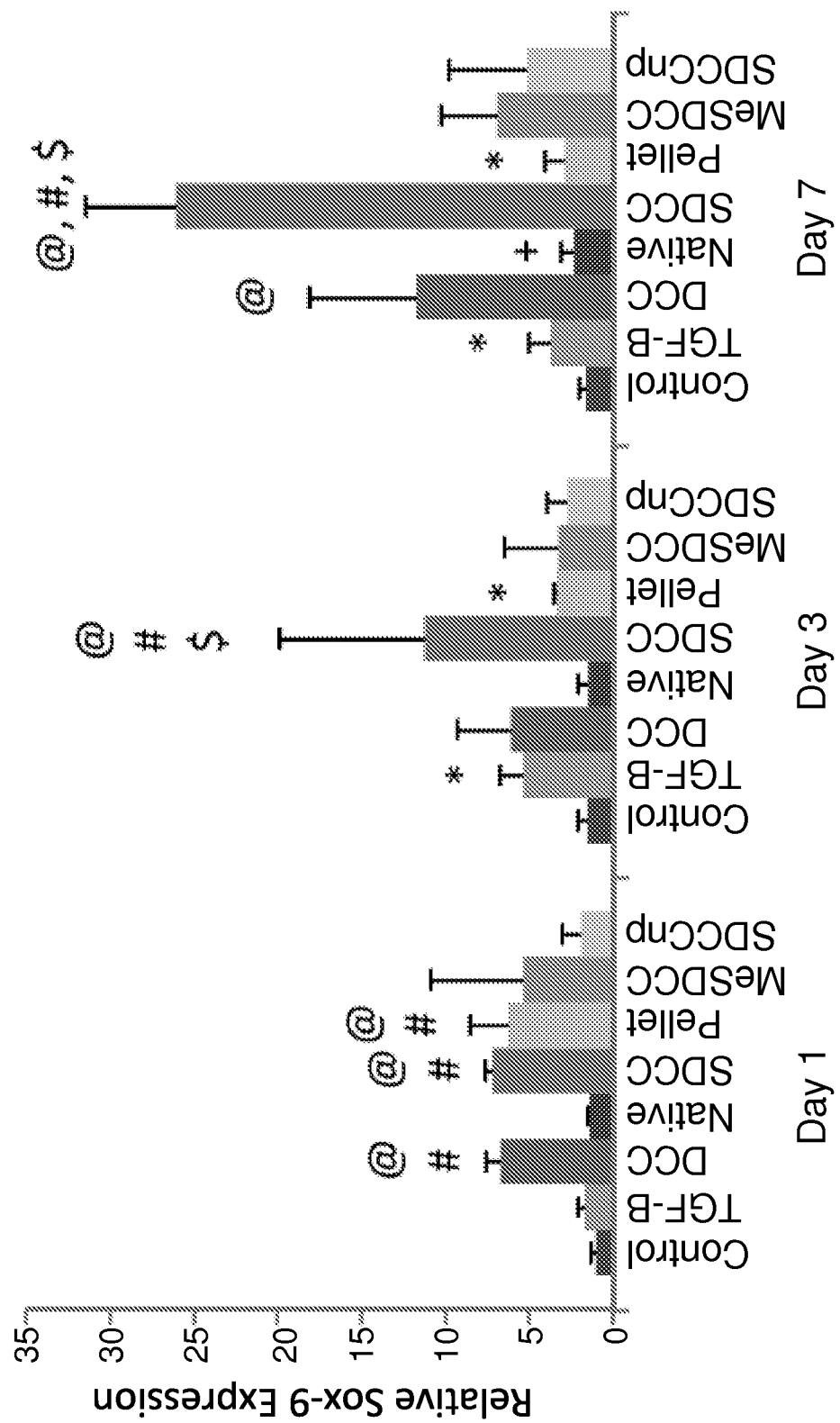
FIG. 19 illustrates the relative expression of Sox-9 in the groups of control, TGF-B, DCC, Native, SDCC, Pellet, Me SDCC, and SDCCnp.
Figure 20:
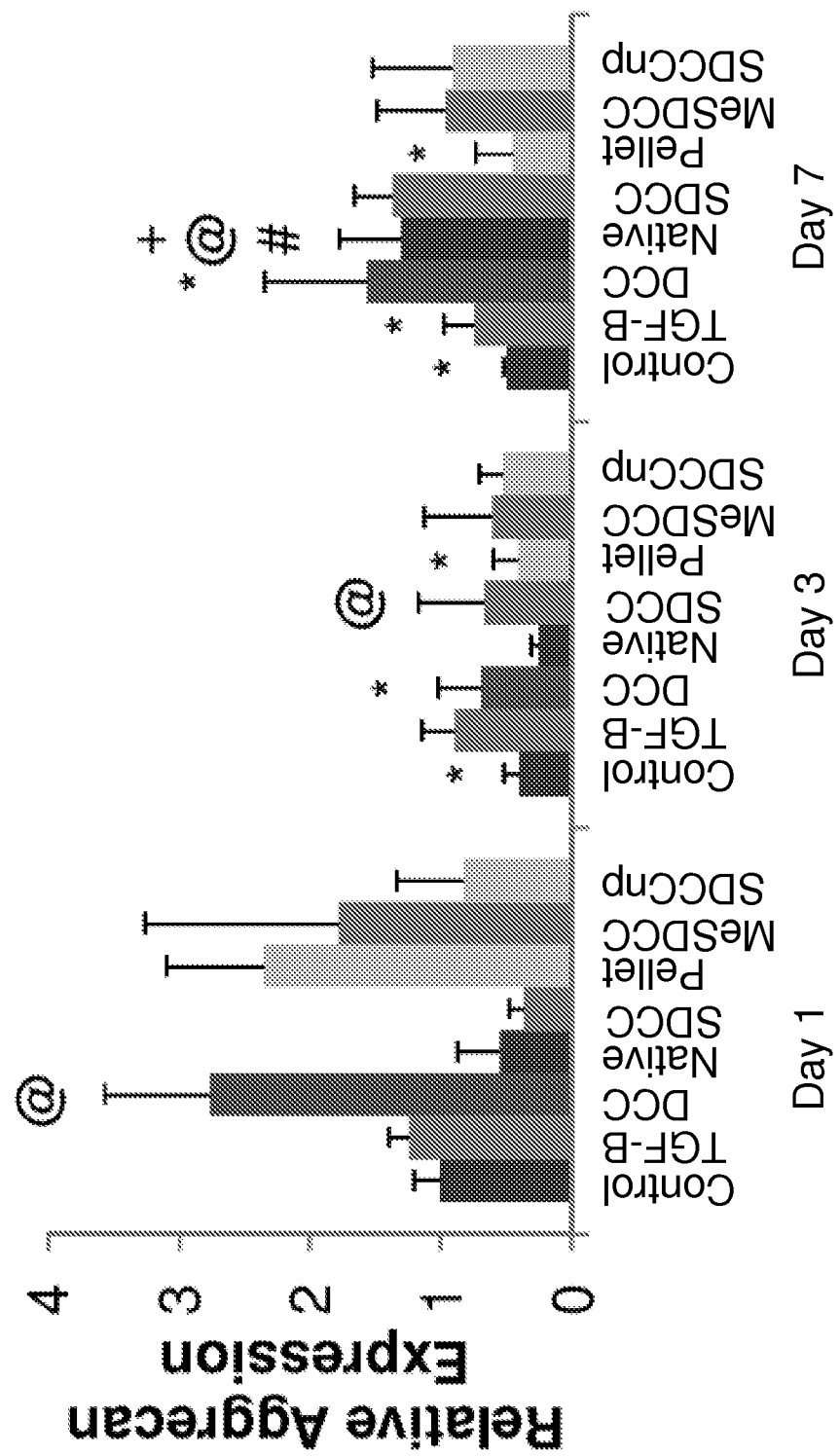
FIG. 20 illustrates the relative Agrecan expression in the groups of control, TGF-B, DCC, Native, SDCC, Pellet, Me SDCC, and SDCCnp.

In this experiment, a pellet study was performed where cells were exposed to DCC materials and cultured for 1, 3, and 7 days. However, the data on exposure to SDCC, SDCCpellet, MeSDCC, and SDCCnp showed that each of these DCC materials caused some significant upregulation of a chondrogenic marker (FIG. 18 Collagen II; FIG. 19 Sox-9; and, FIG. 20 Aggrecan).

EXAMPLE 8

This example illustrates the applications of microsphere scaffolds in contacting with the decellularized cartilage tissue powder. Extracellular matrix (ECM)-based materials are attractive for regenerative medicine in their ability to potentially aid in stem cell recruitment, infiltration, and differentiation without added biological factors. In musculoskeletal tissue engineering, demineralized bone matrix is widely used, but recently cartilage matrix has been attracting attention as a potentially chondroinductive material. The aim of this study was thus to establish a chemical decellularization method for use with articular cartilage to quantify removal of cells and analyze the cartilage biochemical content at various stages during the decellularization process, which included a physically devitalization step.

Materials and Methods

Porcine articular cartilage was devitalized and decellularized and samples from each stage of decellularization were analyzed for biochemical content. To study the cellular response to the cartilage matrix, rat bone marrow-derived mesenchymal stem cells (rBMSCs) were cultured in cell pellets containing cells only (control), chondrogenic differentiation medium (TGF-β), chemically decellularized cartilage particles (DCC), or physically devitalized cartilage particles (DVC), and the DNA content and gene expression were analyzed over a one week period.

Tissue Retrieval, Decellularization, and Devitalization

Figure 21:
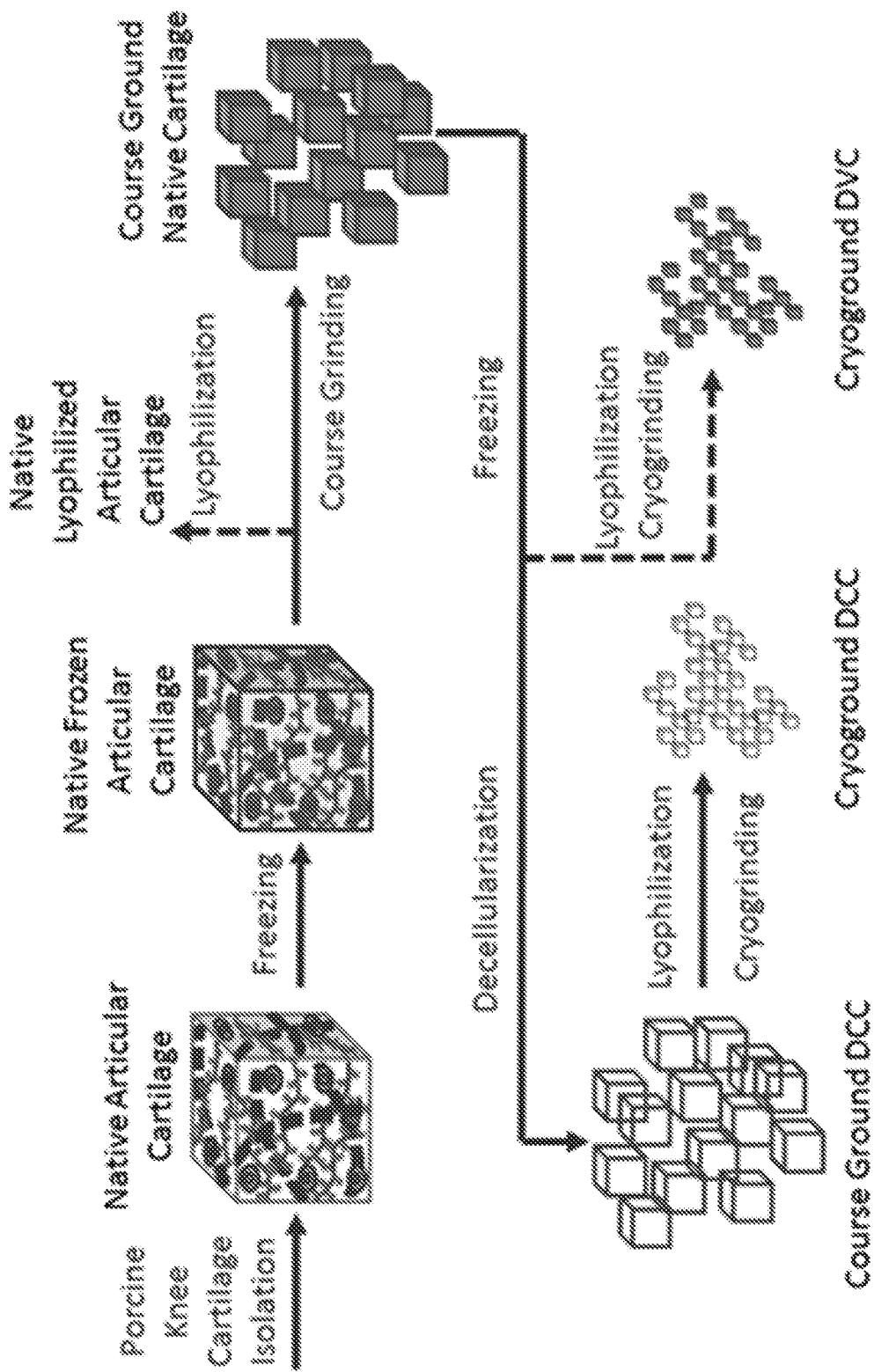
FIG. 21 illustrates the process between porcine knee cartilage isolation and preparing cryground DVC.

Ten porcine knee and hip joints were purchased following sacrifice (120 kg, mixed breed, mixed gender) (Bichelmeyer Meats, Kansas City, Kans.) and processed according to the schematic in FIG. 21 Articular cartilage from both the knee and hip joints was carefully removed and collected using scalpels. The cartilage was rinsed in phosphate buffered saline (PBS) and stored at −20° C. Following freezing, the cartilage was coarsely ground using a cryogenic tissue grinder (BioSpec Products, Bartlesville, Okla.). The coarsely ground tissue was packaged into dialysis tubing (3500 MWCO) packets for decellularization.

Cartilage was devitalized (i.e., forming DVC) following tissue harvest by immediately freezing at −20° C. and then lyophililzing the tissue. The lyophilized tissue was then processed in a freezer-mill and frozen again at −20° C.

The cartilage was decellularized (i.e., forming DCC) using an adapted version of our previously established method using reciprocating osmotic shock, detergent, and enzymatic washes. 23 Reagents were purchased from Sigma-Aldrich (St. Louis, Mo.) unless otherwise noted. All steps of decellularization were carried out under agitation (200 rpm) at 21° C. unless otherwise noted. First, the cartilage packets were placed in hypertonic salt solution (HSS) overnight to disrupt membranes and lyse the cells. Following HSS treatment, the tissue was subjected to 2 cycles of reciprocating triton-X 100 (0.05% v/v) and HSS treatments to further break down cellular membranes. The tissue was then treated with benzonase (0.0625 KU ml-1) overnight at 37° C. to fragment nucleic acids. Sodium-lauroyl sarcosine (NLS, 1% v/v) was then used overnight to further solubilize and remove cells. Next, the tissue was washed with 40% ethanol, followed with organic exchange resins to remove all organic solvents. Lastly, the tissue was removed from the dialysis tubing packages and rinsed with deionized water before freezing.

After decellularization, the tissue was lyophilized for 48 hours and cryo-ground into a fine powder with a freezer-mill (SPEX SamplePrep, Metuchen, N.J.).

Scanning Electron Microscopy

The size and morphology of DCC particles were observed using LEO 1550 field emission scanning electron microscopy (SEM). Prior to imaging, DCC particles were lyophilized and sputter-coated with gold.

BMSC Harvest and Pellet Formation

Rat bone marrow mesenchymal stem cells (rBMSC) were harvested from the femurs of 4 male Sprague-Dawley rats (200-250 g) following an approved IACUC protocol. The BMSCs were cultured in minimum essential medium (MEM) a culture medium with 10% fetal bovine serum (FBS) and 1% antibiotic-antimycotic (anti-anti) during expansion. At passage 4, the cells were suspended in MEM α culture media at $1 \times 10^6$ cells/mL. 1 mL of cell suspension was added to 25 mg of both DCC and DVC and centrifuged for 5 minutes to form a pellet (n=5). The TGF-β and negative control groups contained $10^6$ cells without additional material. Experimental and negative control groups were cultured in 1 mL of the medium used during expansion. The TGF-β control group was cultured in chondrogenic differentiation medium containing 10 ng/mL human recombinant TGF-β3 (PeproTech, Rocky Hill, N.J.), 50 μg/mL ascorbic acid, 1% Penicillin Streptomycin, 40 μg/mL L-proline, 100 μmol sodium pyruvate, 0.1 μm dexamethasone, 1% insulin-transferrin-selenium 100× (ITS), and 1% non-essential amino acids (NEAA). The medium was changed every 48 hours.

Biochemical Analysis

The biochemical content of the cartilage was assessed after each processing step: native hydrated, native frozen, native lyophilized, native cryo-ground (DVC), decellularized coarse ground, and decellularized cryo-ground cartilage (DCC). The DNA content was also assessed at day 1 and 7 of pellet culture (n=5). Prior to biochemical analysis, all tissue samples were digested in a papain solution for 24-48 hours.

Biochemical content was measured using known procedures. Briefly, glycosaminoglycan (GAG) content was measured with a dimethylmethylene blue (DMMB) assay kit (Blyscan, Westbury, N.Y.). Total hydroxyproline content was measured using a commercially available hydroxyproline detection kit (Sigma, St. Louis, Mo.). Double-stranded DNA was detected using a high sensitivity PicoGreen assay kit (Molecular Probes, Eugene, Oreg.). All assay kits were used in accordance with each manufacturer's guidelines.

Gene Expression

RNA was isolated and purified from cells using the Qiagen RNeasy mini kit (Valencia, Calif.). All RNA samples were reverse transcribed using a high capacity cDNA reverse transcription kit (Invitrogen, Carlsbad, Calif.). Real-time quantitative polymerase chain reaction (qPCR) was performed using a RealPlex MasterCycler (Eppendorf, Hauppauge, N.Y.) and TaqMan gene expression assays using equal concentrations of DNA for each sample. Rat specific Col2A1, Col1A1, Runx2, Sox9, Col10A1, Acan, and GAPDH commercially available primers were used (Invitrogen, Carlsbad, Calif.). The 2-ΔΔCt method was used to determine the relative expression of each gene with GAPDH used as an endogenous control.27, 28

Statistical Analysis

Results are reported as a mean±standard deviation. SPSS statistical software was used to construct boxplots to remove outliers prior to performing statistical analyses. All statistical analyses were performed using a one way analysis of variance (ANOVA) and Tukey's post-hoc tests. Significance was determined for $p<0.05$.

Results and Conclusions

Tissue Decellularization and Processing

Figure 22:
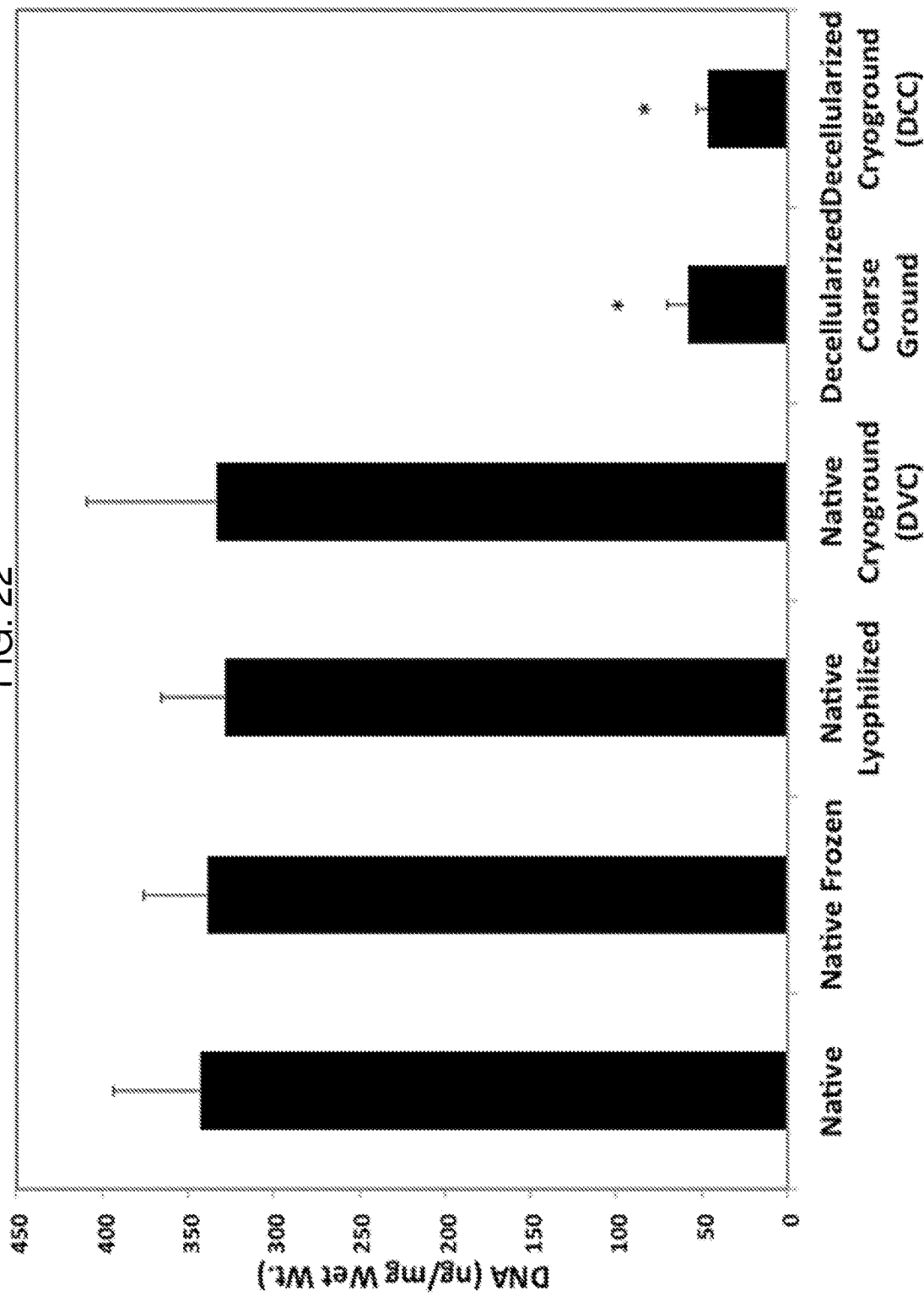
FIG. 22 illustrates the amount of DNA present in several tissues compared with decellularized coarse ground and decellularized cryground tissue, wherein * denotes p<0.01 (n=6) with all results reported as mean±standard deviation.
Figure 23:
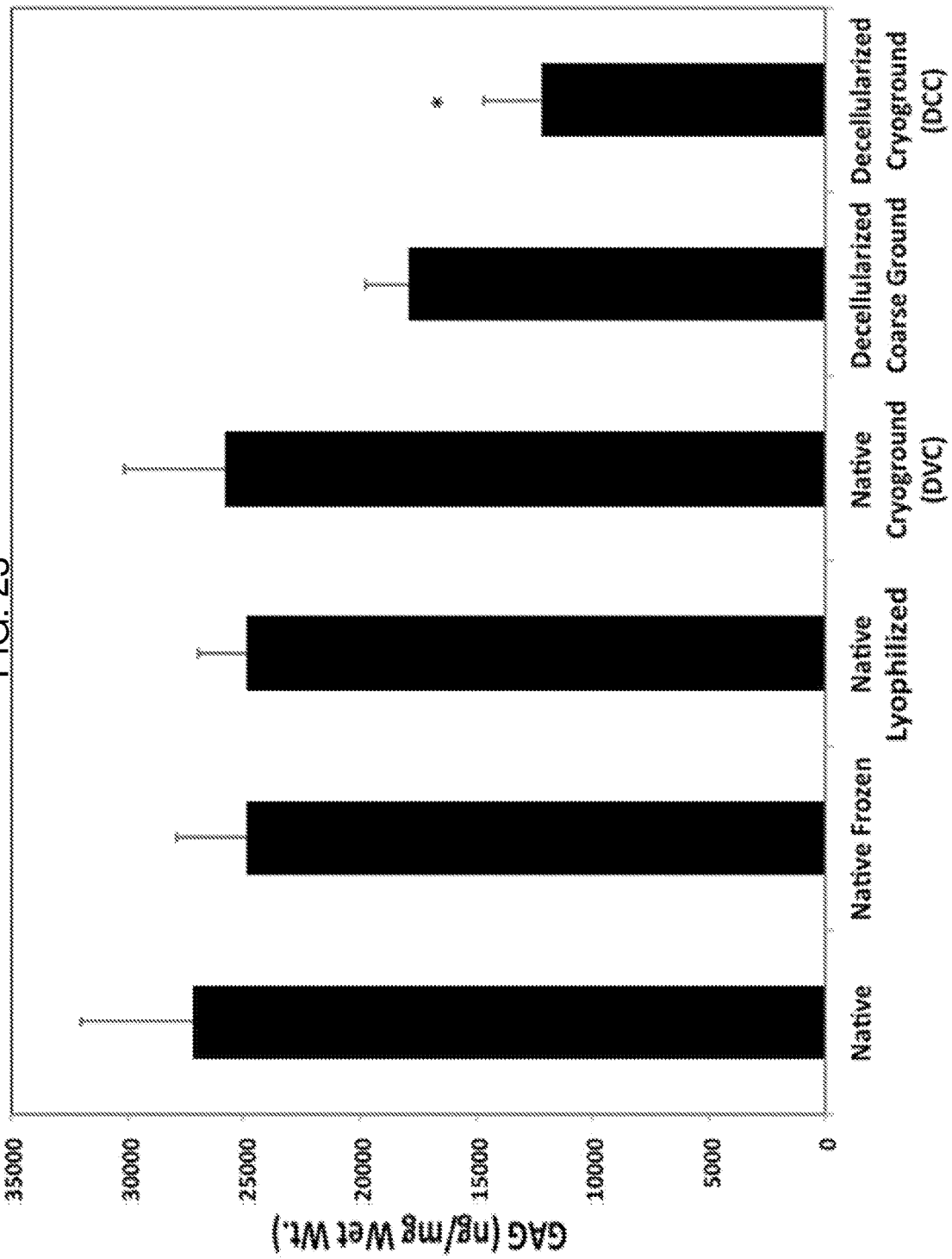
FIG. 23 illustrates the amount of GAG present in several tissues compared with decellularized coarse ground and decellularized cryground tissue, wherein * denotes p<0.01 (n=6) with all results reported as mean±standard deviation.
Figure 24:
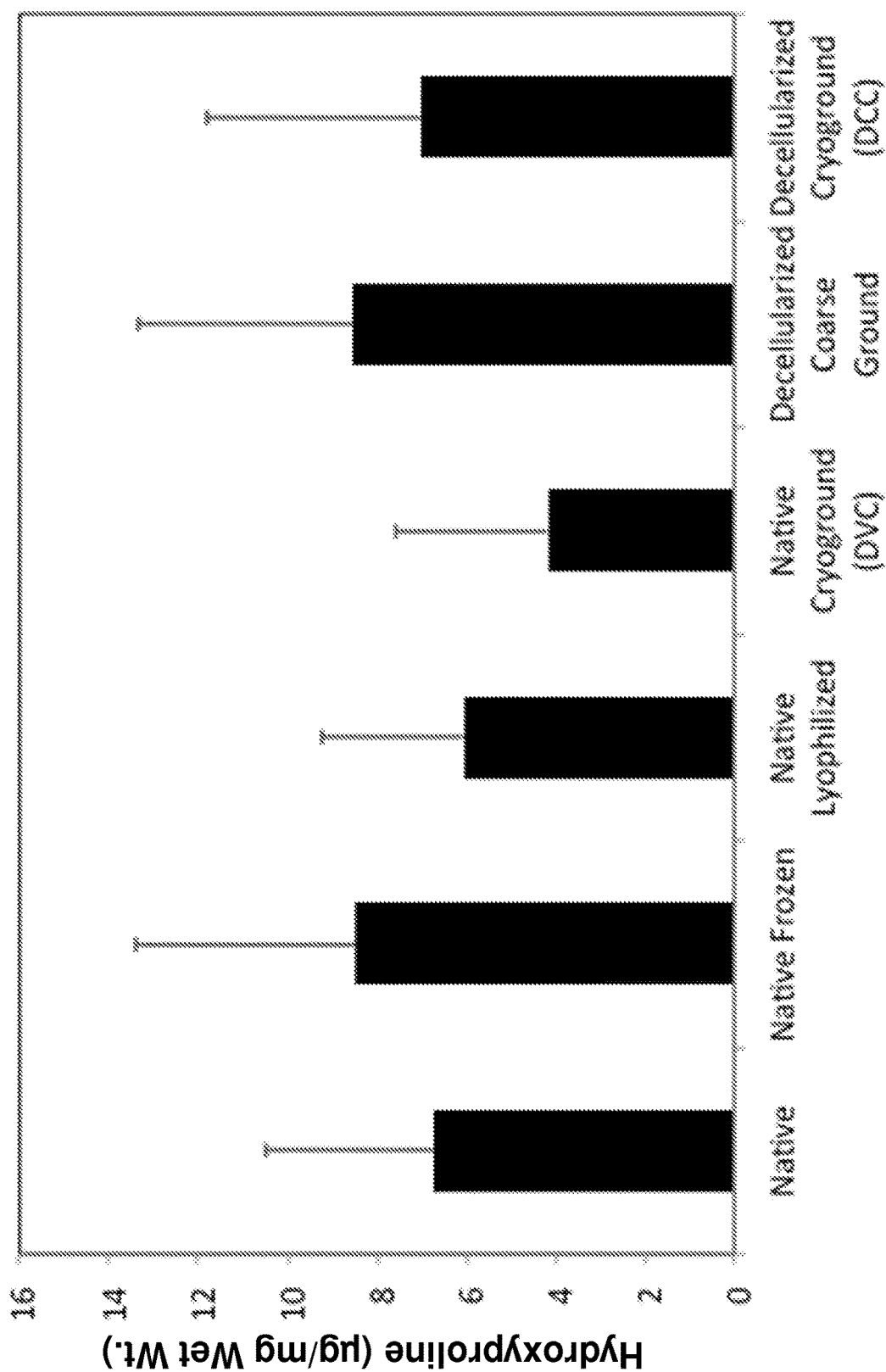
FIG. 24 illustrates the amount of hydroxyproline present in several tissues compared with decellularized coarse ground and decellularized cryground tissue.

Following coarse grinding, chemical decellularization, and cryo-grinding there was an 86% reduction in DNA content ($p<0.01$) (FIG. 22) and a 55% reduction in GAG content ($p<0.01$) (FIG. 23). However, there was no significant difference in hydroxyproline content during any steps of the tissue processing (FIG. 24). Freezing, lyophilization, and cryo-grinding had no significant effect on DNA or GAG content in the tissue.

SEM Imaging

Figure 26:
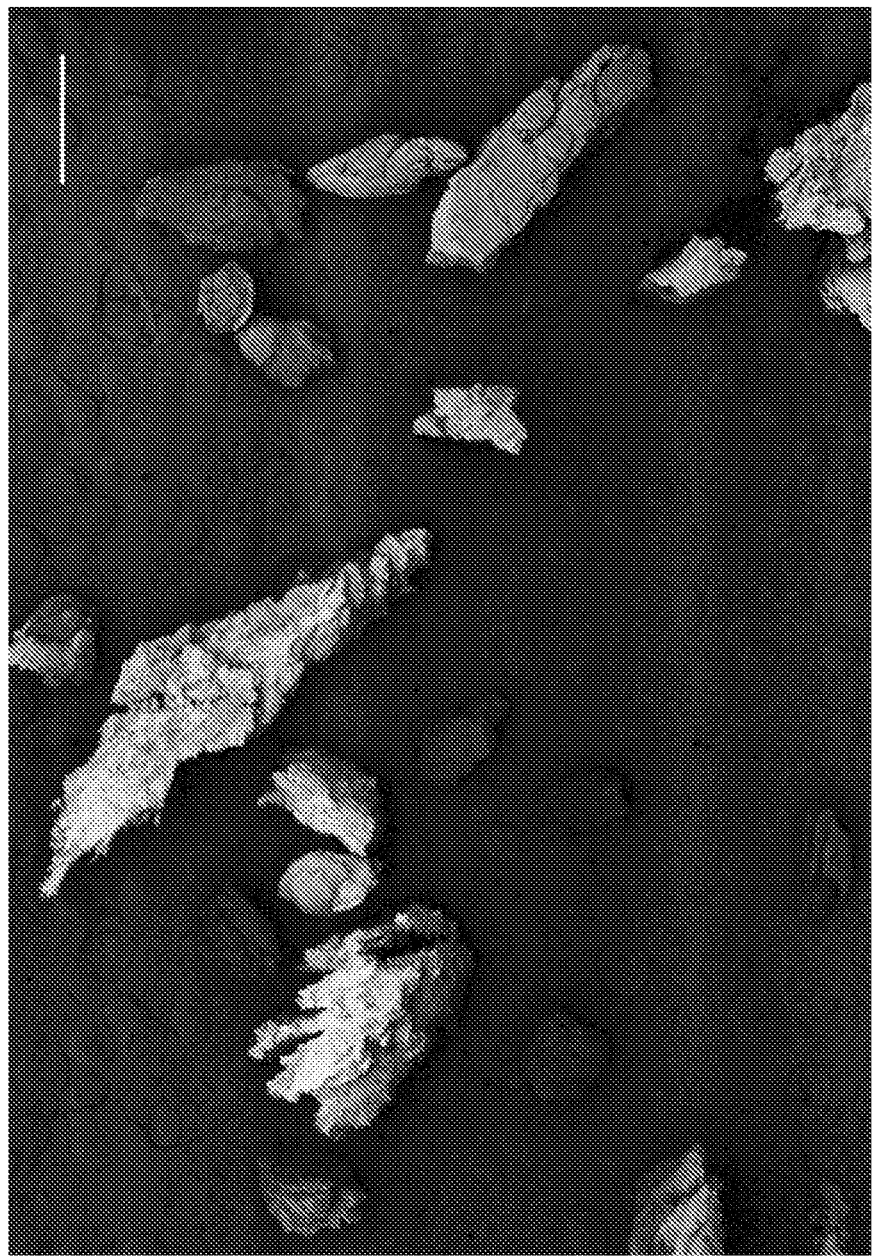
FIG. 26 is a photograph of magnified decellularized cryground tissue.

SEM imaging revealed that DCC particles are heterogeneous in morphology and size (FIG. 26).

Cell Viability

Figure 25:
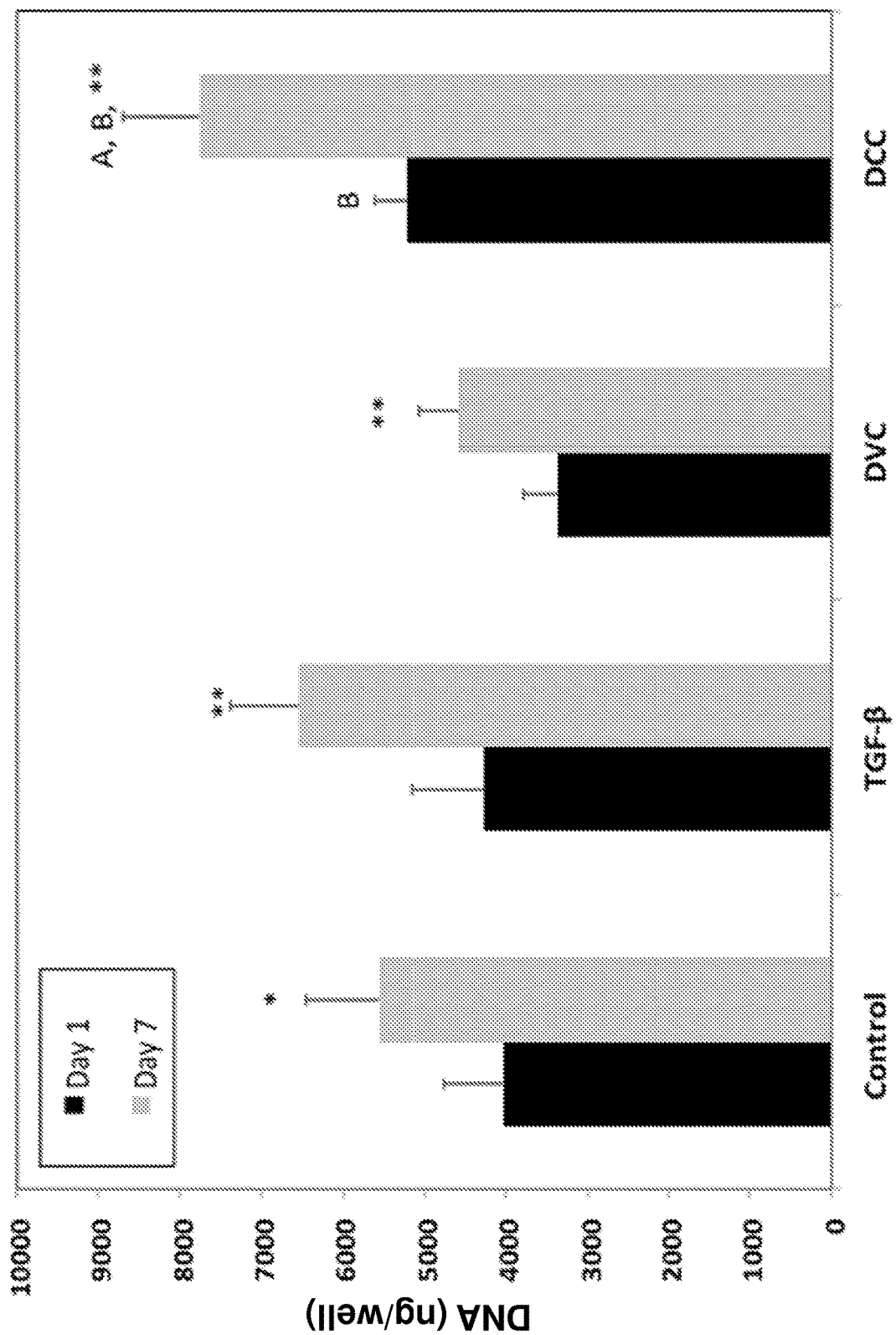
FIG. 25 illustrates the amount of DNA located in tissue when comparing the control, TGF-B, DVC, and DCC wherein *=p<0.05 between day 1 and 7, **=p<0.01 between day 1 and 7, A=p<0.05 between DCC and control, and B=p<0.01 between DCC and DVC, with all results reported as mean±standard deviation.

DNA was quantified in cell pellets at 0 and 7 days to determine cell proliferation on devitalized and decellularized cartilage. All cell pellets showed a significant increase in DNA amount over 7 days ($p<0.05$) (FIG. 25). At 7 days, cell pellets with DCC had approximately 40% more DNA than the DVC cell pellets at the same time ($p<0.01$) (FIG. 25). DCC pellets also had approximately 30% more DNA than the negative control group ($p<0.01$) (FIG. 25).

Figure 27A:
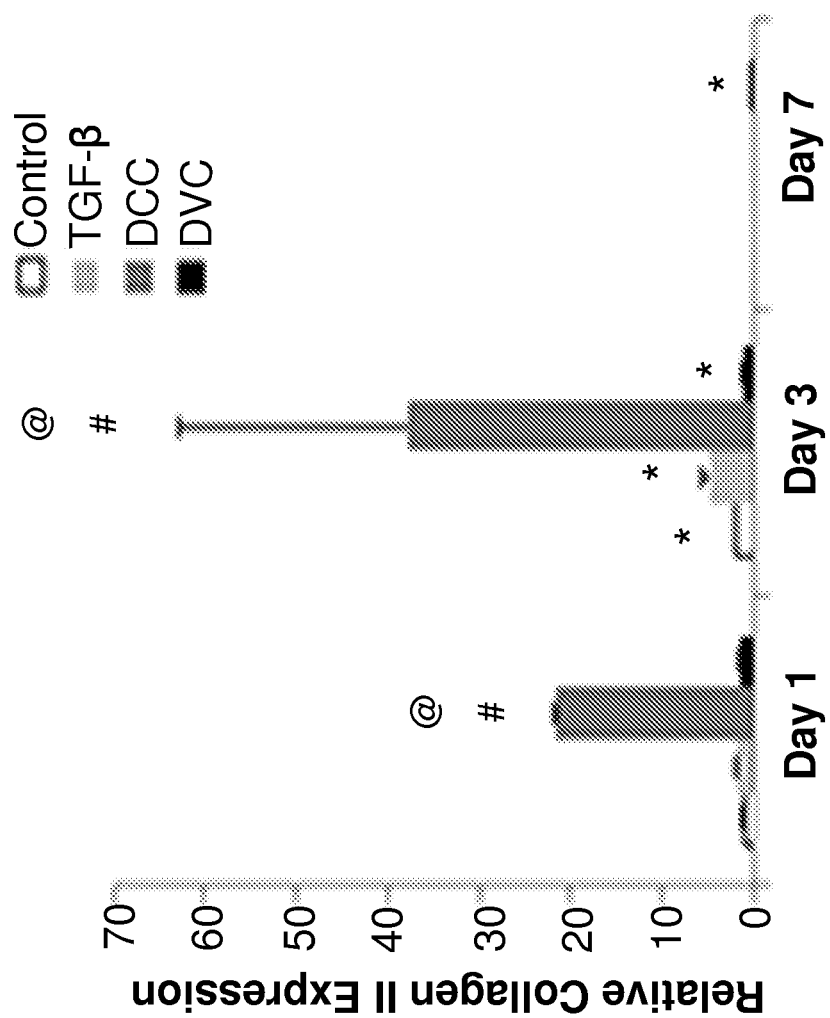
FIGS. 27 A, B, C, D, E, and F show the expression of Collagen II, Sox-9, Aggrecan, Collagen X, Runx-2, and Collagen I expression, respectively. In these figures, @ denotes significant difference from control group at same time point, # denotes significant difference from TGF-β group at same time point, * denotes significant difference between day 1 value, + denotes significant difference from previous time point, and $ denotes significant difference from DCC group at same time point.
Figure 27B:
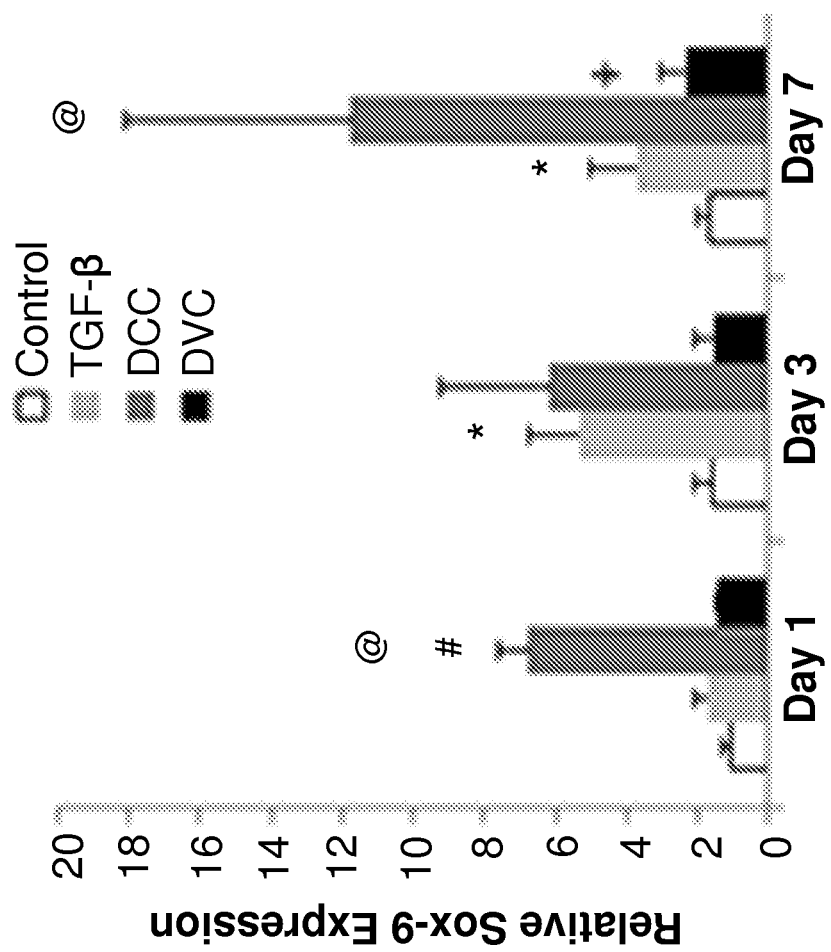
Figure 27C:
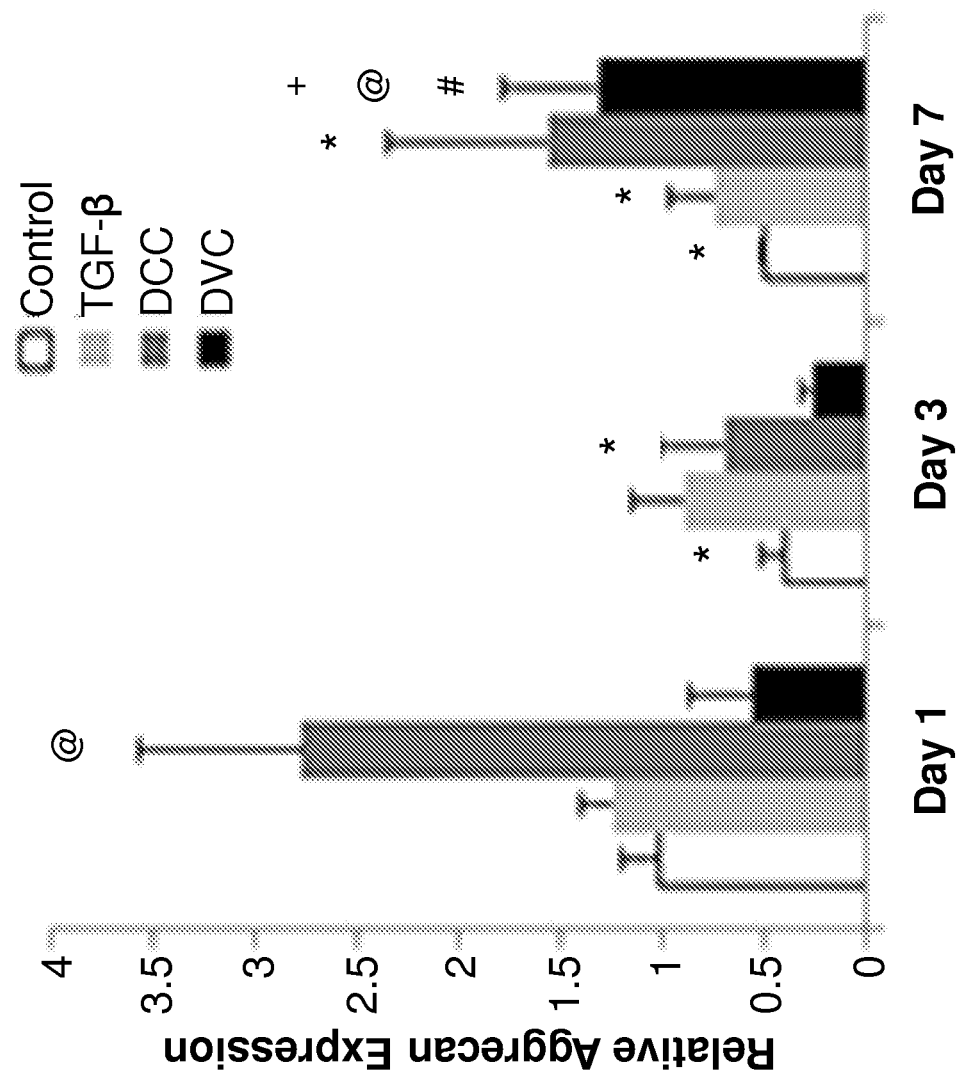
Figure 27D:
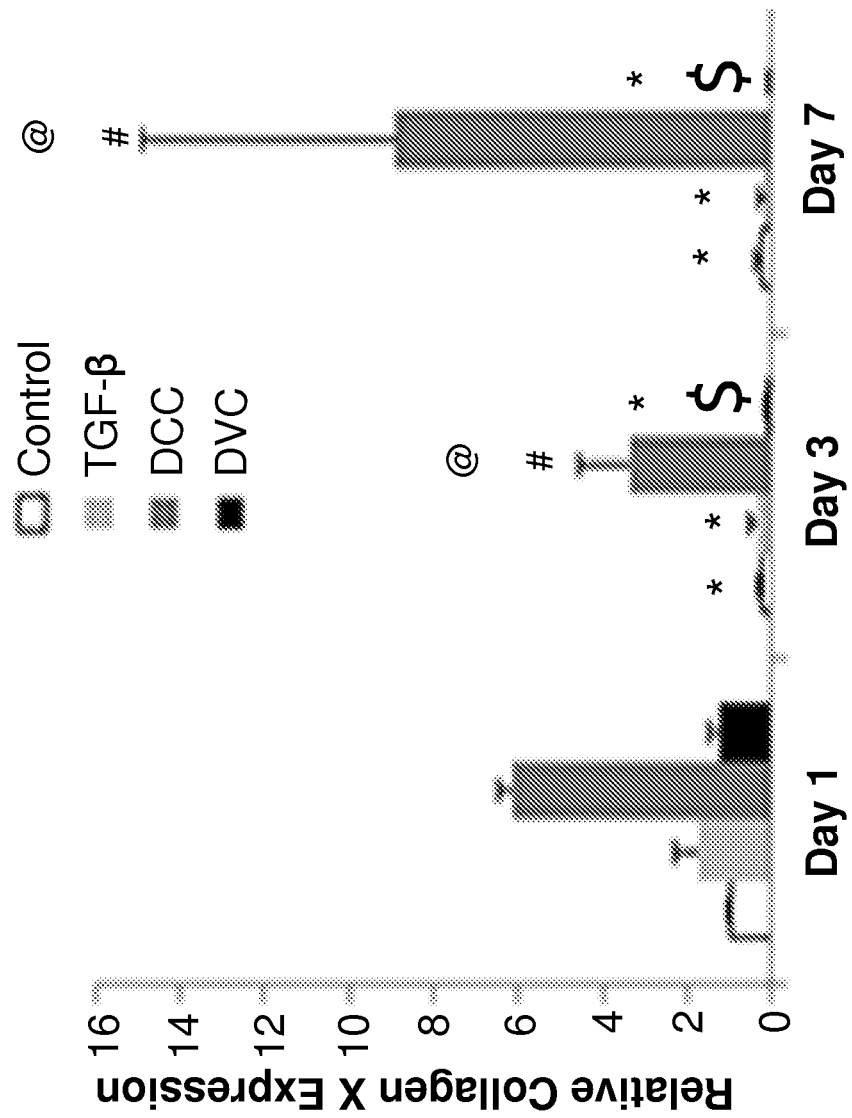
Figure 27E:
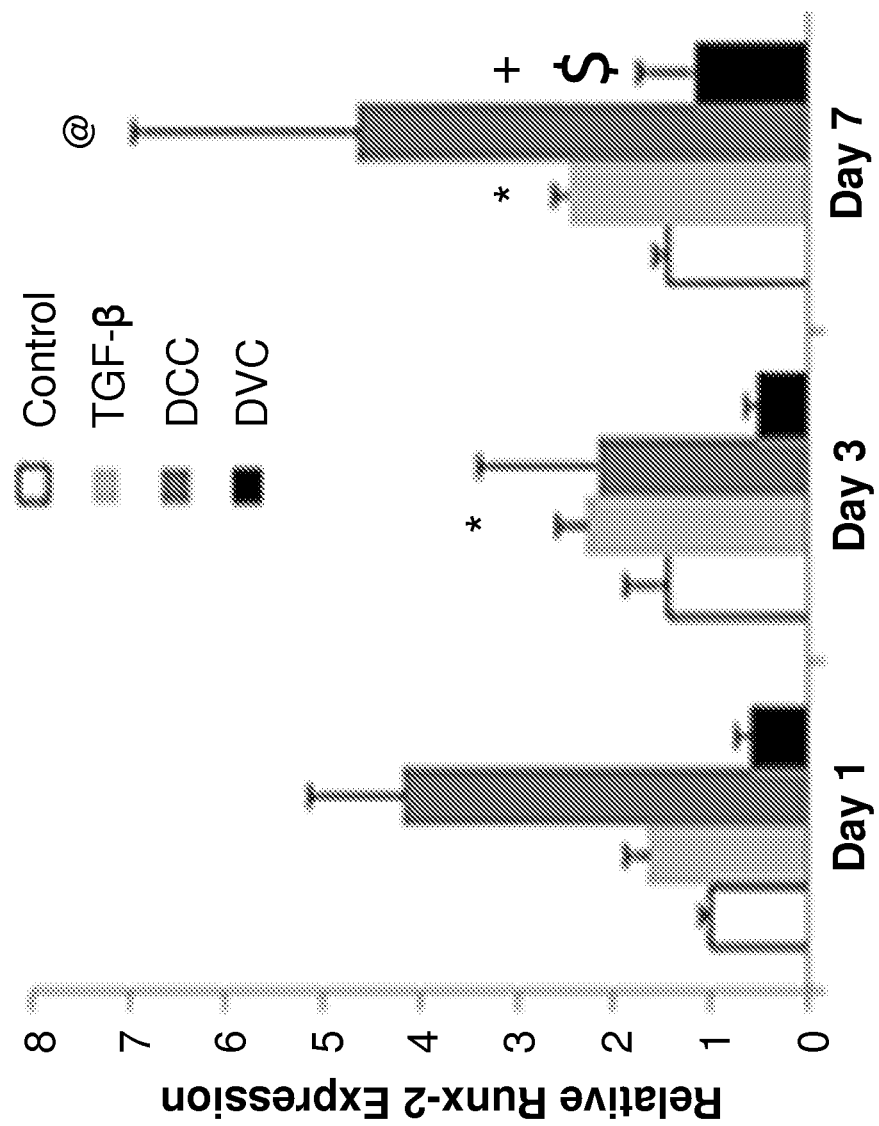
Figure 27F:
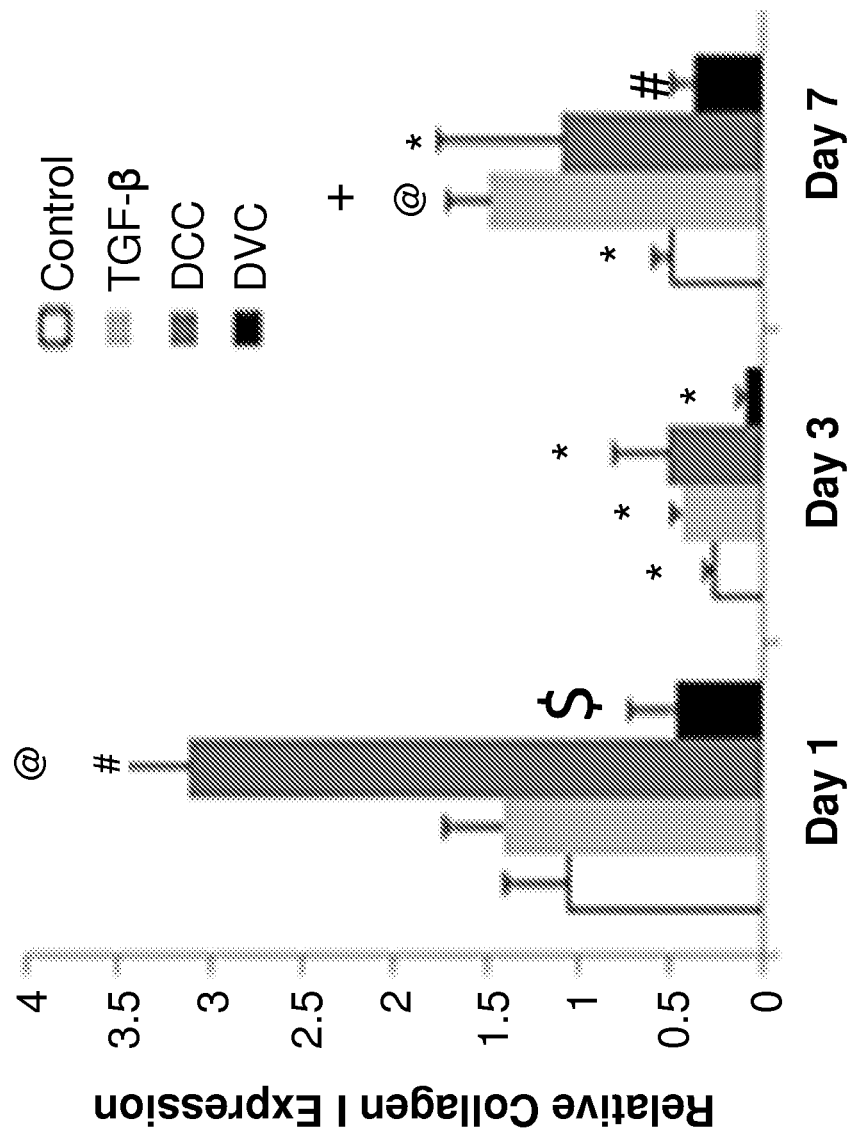

Gene Expression qPCR was used to determine the expression of both chondrogenic and osteogenic genes. DCC pellet group gene expression showed over a 90% increase in collagen II expression compared to both the TGF-β and negative control groups at day 1 ($p<0.01$) (FIG. 27A). Collagen II expression remained greater than both the TGF-β and negative control groups at day 3 ($p<0.01$). The DCC pellet group also showed 75% greater upregulation of Sox9 compared to the TGF-β group at day 1 ($p<0.01$) (FIG. 27B). A 60% increase in aggrecan expression was observed in the DCC group compared to the negative control at day 1 ($p<0.01$) (FIG. 27C). The osteogenic marker collagen X was expressed 5 times greater in the DCC group compared to the negative control group at day 7 ($p<0.01$) (FIG. 27D). Collagen X was also expressed 45 times greater in DCC than in the TGF-β group ($p<0.01$). Runx2 expression in the DCC group was also upregulated compared to the negative control group by 75% at day 7 ($p<0.05$) (FIG. 27E). Collagen I expression in the DCC group was also over 50% greater than both the negative control and TGF-β groups at day 1 ($p<0.01$), but significantly decreased at both days 3 and 7 compared to day 1 ($p<0.05$) (FIG. 27F).

The DVC group saw no significant difference in collagen II expression from both the negative control and TGF-β groups at days 1 and 3 (FIG. 27A). Aggrecan expression in the DVC group was over 40% greater than both the TGF-β and negative control groups at day 7 ($p<0.05$), however, it was not statistically significant from the DCC group at the same time (FIG. 27C). The DVC group Sox9 expression increased approximately 30% between days 3 and 7 ($p<0.05$) but was not significantly greater than either control group or the DCC group (FIG. 27B). Expression of osteogenic marker collagen X was 100% less in the DVC group compared to the DCC group at day 7 ($p<0.01$) (FIG. 27D). Runx2 expression was also 30% less in the DVC group compared to the DCC group at day 7 ($p<0.01$) (FIG. 27E). Collagen I expression in the DVC group was 60% less than the DCC group at day 1 ($p<0.01$) and 3 times less than the TGF-β group at day 7 ($p<0.05$) (FIG. 27F).

Discussion

Synthetic biomaterials have achieved clinically relevant mechanical performance for osteochondral implantation; however, they have not been successful at fully regenerating functional articular cartilage. The use of ECM-based materials for osteochondral tissue engineering is a promising avenue because of the ECM materials' ability to mimic the native cartilage environment by providing cells with adhesion sites and biochemical signals that aid in recruiting and differentiating stem cells for tissue regeneration. ECM-based materials may be able to provide these signals to cells without manipulation of the material with added biological factors (e.g., growth factors or adhesion peptides).

Successful decellularization of articular cartilage has previously been accomplished using different methods with differing results with respect to the remaining biochemical content, cell removal, and mechanical performance. Cartilage ECM has also been used as a scaffolding material that has only been physically devitalized as opposed to being decellularized. The different effects that devitalization vs. decellularization have on the cartilage matrix until now have not been fully characterized throughout each respective process. Moreover, DVC and DCC have not been directly compared in vitro or to a positive control such as TGF-β. The current study has shown that DCC may outperform both DVC and TGF-β at inducing chondrogensis in BMSCs in vitro. However, a limitation of this study is the inclusion of FBS in all of the experimental groups except the TGF-β supplemented group.

The current combined physical and chemical decellularization method was successful at reducing the amount of detectable dsDNA within the cartilage matrix by 86% (p<0.01). Freezing, lyophilization, and cryogrinding, all common devitalization techniques, as expected were not effective at removing any dsDNA from the matrix. Although the DNA content of the DCC was significantly reduced, the GAG content was also significantly reduced by 55% (FIG. 3). Retaining GAG content in cryo-ground DCC is crucial as the size of cryo-ground DCC versus coarse ground DCC is more ideal to incorporate into 3D scaffolds, such as pastes, hydrogels, and microspheres.

Currently, little is understood about the mechanism by which cartilage matrix materials induce chondrogenesis in vitro. Retention of GAG within the matrix may be beneficial for chondroinduction based on previous studies citing that GAGs, such as chondroitin sulfate and aggrecan, may have chondroinductive effects in vitro. Although GAG retention may be beneficial for cell signaling, a partial reduction in GAG content may be beneficial to create a less dense matrix that allows for cell infiltration and migration.

In the current study, BMSCs cultured with DCC showed increased expression of both chondrogenic and osteogenic gene markers compared to the negative control group. Even though some evidence of osteogenesis was observed alongside chondrogenesis in this in vitro experiment, it is also hypothesized that in future work where this material is implanted in an osteochondral defect, for example, that the complex environment of mechanical and chemical signaling in vivo may possibly lead to regional differentiation, from chondrogenesis at the surface to possibly endochondral ossification below. Overall, the DVC group showed lower expression of the osteogenic markers collagen X and Runx2 than the DCC group. Although the DVC seemed to limit osteoinduction in the BMSCs, the chondrogenic gene markers collagen II, aggrecan, and Sox9 were significantly upregulated in the DCC group compared to the DVC group. This suggests that chondroinduction by DCC is not affected by the decellularization method. Additionally, comparison between chondroinduction via TGF-β and DCC showed that DCC chondroinduction was not statistically significant with respect to expression of aggrecan and Runx2 at all time points. Chondroinductive markers including collagen II and Sox9 were expressed 20 and 4 times higher respectively in the DCC group compared to the TGF-β group at day 1. Similar expression of collagen I between the DCC group and the TGF-β group was also seen at 3 and 7 days. These results suggest that DCC may outperform TGF-β at inducing chondrogenesis but does not confirm that latent TGF-β within the DCC matrix is responsible for the observed chondrogenesis.

It is still unclear whether full decellularization of articular cartilage is necessary when delivering cartilage matrix materials to osteochondral defects in vivo. Decellularization may reduce the antigenicity of the matrix by removing cellular materials that have been previously shown to elicit immune responses such as human leukocyte antigens (HLA) and the alpha-Gal epitope. Previous studies have shown successful removal of the alpha-Gal epitope through chemical decellularization but not physical devitalization alone. Further investigations are needed to evaluate immunogenicity and successful removal of the alpha-Gal epitope.

Although not specifically explored in the current study, a delivery method of this material must also be considered to create a tissue engineering scaffold with that contains both the benefits of cartilage matrix materials with enhanced mechanical performance. The development of an acellular, non-biologically modified biomaterial that has the ability to induce chondrogenesis is of particular importance to the tissue engineering field because of it may have the ability to replace current surgical techniques with more positive outcomes. The ECM material approach is also highly attractive from both a regulatory and commercialization standpoint because of the cost of materials and no added biologic factors.

This is the first study to fully characterize both DCC and DVC through the respective decellularization and devitalization processes. Additionally, this is the first study to directly compare the bioactivity of non-crosslinked DCC, DVC, and TGF-β in vitro. DCC was found to have superior effects compared to both DVC and TGF-β at inducing chondrogensis and supporting cell proliferation. The ability to influence cell differentiation without additional biological manipulation makes DCC a promising biomaterial for use in future cartilage tissue engineering applications.

Tissue engineering techniques classically involve the use of scaffolds that serve as physical templates for the matrix-forming cells to attach and orient, guided by molecular cues that dictate their phenotypic characteristics. The basic tissue engineering principles also apply for tissues such as meniscus, ligament, and tendon.

What is claimed is:

1. A composition comprising:
    decellularized cartilage (DCC) particles ranging in size from about 1 nanometer to about 500 micrometers and have about 85% or more glycosaminoglycan content retained in comparison to fresh cartilage tissue from which the DCC particles were prepared.

2. The composition of claim 1, wherein the DCC particles have no more than about 20% of dsDNA retained in comparison to fresh cartilage tissue from which the DCC particles were prepared.

3. The composition of claim 1, the composition formed as a hyaline cartilage tissue hydrogel, comprising:
    the DCC particles having a majority of the particles ranging in size between about 1 nanometer and about 500 micrometers, and
    at least one hydrogel.

4. The composition of claim 3, wherein said hydrogel is Methacrylated Hyaluronic Acid (MeHA) and wherein said cartilage tissue hydrogel has a yield stress between about 0 Pa to about 400 Pa.

5. The composition of claim 1, comprising:
    polymeric microspheres in contact with the DCC particles, the DCC particles ranging in size from between about 7 nanometers and about 200 micrometers.

6. The composition of claim 5, wherein the DCC particles are coated onto said microspheres.

7. The composition of claim 5, wherein the DCC particles encapsulated in said microspheres.

8. The composition of claim 5, wherein said composition is in a form of a tissue engineering scaffold.

9. The composition of claim 8, wherein the tissue engineering scaffold includes the polymer microspheres coated with the DCC particles, the particles ranging in size from about 10 nanometers to about 50 micrometers.

10. The composition of claim 8, wherein the tissue engineering scaffold includes the polymer microspheres encapsulated with the DCC particles, the particles ranging in size from about 10 nanometers to about 50 micrometers.

11. The composition of claim 1, wherein the DCC particles range in size between about 8 nanometers to about 150 microns.

12. The composition of claim 1, wherein the DCC particles range in size between about 10 nanometers to about 50 microns.

13. The composition of claim 1, wherein the DCC particles are solubilized with an acid.

14. The composition of claim 1, further comprising a solution having the DCC particles soluble in the solution.

15. The composition of claim 1, wherein the DCC particles are methacylated.

16. The composition of claim 15, further comprising a solution having the methacrylated DCC particles soluble in the solution.

17. The composition of claim 1, further comprising a solution having the DCC particles, wherein a first portion of the DCC particles are soluble in the solution and a second portion of the DCC particles are precipitates at a bottom of the solution.

18. The composition of claim 15, wherein the methacrylated DCC particles are a dry powder.

19. The composition of claim 15, wherein the methacrylated DCC particles are crosslinked methacrylated soluble DCC particles.

20. The composition of claim 19, wherein the methacrylated DCC particles are a dry powder.

21. The composition of claim 1, wherein the DCC particles range in size between 20 nanometers to 50 microns with a majority of the DCC particles being less than 20 microns.

22. The composition of claim 1, wherein the glycosaminoglycan content is between 2.066+/−0.099 µg glycosaminoglycan/mg hydrated tissue to 2.353 +/−0.088 µg glycosaminoglycan/mg hydrated tissue.

23. The composition of claim 14, wherein the solution is an acidic solution having the DCC particles and pepsin.

24. The composition of claim 14, wherein the solution has the DCC particles and glycidyl methacrylate.

25. The composition of claim 3, wherein the DCC particles range in size between about 8 nanometers to about 150 microns.

26. The composition of claim 6, wherein the DCC particles range in size between about 10 nanometers to about 50 microns.

27. The composition of claim 7, wherein the DCC particles range in size between about 10 nanometers to about 50 microns.

28. The composition of claim 19, wherein composition being a gel of the crosslinked methacrylated DCC particles.

29. A hyaline cartilage tissue paste comprising:
10-90% w/v of the DCC particles of claim 1; and
10-90% w/v of a hydrogel.

30. The hyaline cartilage tissue paste of claim 29, wherein said hydrogel is Methacrylated hyaluronic acid (MeHA).

31. The hyaline cartilage tissue paste of claim 29, further comprising one or more additives selected from the group consisting of carriers, one or more therapeutic agents, one or more biomaterials for tissue engineering scaffolds, and combinations thereof.

32. The composition of claim 29, wherein the DCC particles range in size between about 8 nanometers to about 150 microns.

* * * * *